(12) United States Patent
Aizenman et al.

(10) Patent No.: US 11,673,916 B2
(45) Date of Patent: Jun. 13, 2023

(54) NEUROPROTECTIVE PEPTIDES AND METHODS OF THEIR USE

(71) Applicant: University of Pittsburgh—Of the Commonwealth System of Higher Education, Pittsburgh, PA (US)

(72) Inventors: Elias Aizenman, Pittsburgh, PA (US); Jason Arnold Justice, Plymouth, MN (US); Anthony John Schulien, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 17/494,605

(22) Filed: Oct. 5, 2021

(65) Prior Publication Data

US 2022/0106360 A1    Apr. 7, 2022

Related U.S. Application Data

(60) Provisional application No. 63/088,074, filed on Oct. 6, 2020.

(51) Int. Cl.
| | | |
|---|---|---|
| *C07K 7/06* | (2006.01) | |
| *A61P 25/00* | (2006.01) | |
| *A61K 38/00* | (2006.01) | |

(52) U.S. Cl.
CPC ............... *C07K 7/06* (2013.01); *A61P 25/00* (2018.01); *A61K 38/00* (2013.01); *C07K 2319/10* (2013.01)

(58) Field of Classification Search
CPC ............ C07K 7/06; A61P 25/00; A61K 38/00
See application file for complete search history.

(56) References Cited

U.S. PATENT DOCUMENTS 9,932,382 B2    4/2018   Aizenman et al.

OTHER PUBLICATIONS

Aizenman et al., "From Clusters to Stroke Busters: The Cellular, Molecular and Translational Biology of Kv2.1/Neuregulin Complexes," Winter Conference on Brain Research, Big Sky, Montana, Jan. 25-30, 2020, Abstract (2 pages).

Justice et al., "Disruption of Kv2.1 somato-dendritic clusters prevents the apoptogenic increase of potassium currents," *Neuroscience* 354:158-167, 2017.

Schulien et al., "Targeted disruption of Kv2.1-VAPA association provides neuroprotection against ischemic stroke in mice by declustering Kv2.1 channels," *Sci Adv.* 6:eaaz8110, 2020 (14 pages).

*Primary Examiner* — Amber D Steele
(74) *Attorney, Agent, or Firm* — Klarquist Sprakman, LLP

(57) ABSTRACT

Neuroprotective peptides derived from the voltage-gated potassium channel Kv2.2 are described. The peptides promote dispersal of the cognate channel Kv2.1 in neurons, thereby blocking pro-apoptotic potassium efflux, and preserving cell viability after apoptotic injury. Methods of preventing and treating neuronal damage, such as neuronal damage following ischemic stroke, by administering the neuroprotective peptides are described. Fusion of the neuroprotective peptides to a cell-penetrating peptide to promote cellular uptake is also described.

20 Claims, 22 Drawing Sheets

Specification includes a Sequence Listing.

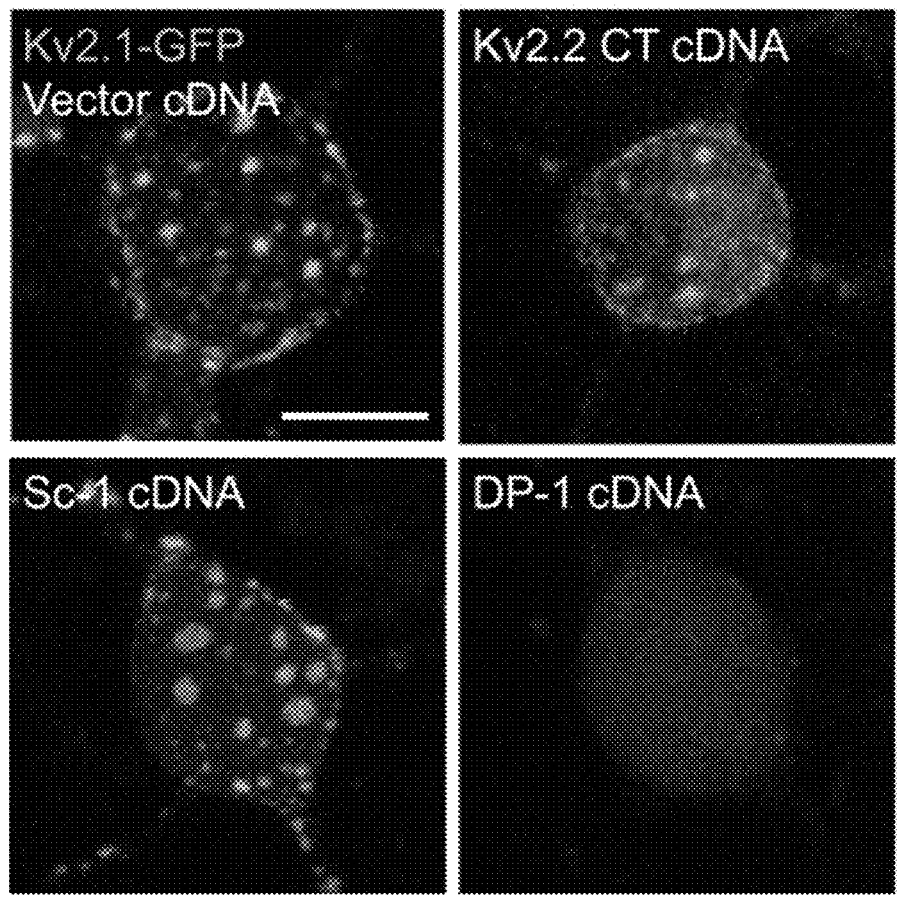

Kv2.2 PRC

E V I V D M K S T S S I D S T T S C A T D F T E T E
592                  602           608              617

Kv2.1 PRC

E G V I D M R S M S S I D S T I S C A T D F P E A T
577                    587    │    593                602
                              P
                             590

Critical Clustering Residues = ●    Known Serine Phosphorylation Sites = ●
VAP-interacting Domain = ▓

Inferred Minimum Clustering Sequence:

Cell-Permeant Declustering Peptide-2 (TAT-DP-2)

602 (Kv2.2)     608 (Kv2.2)

Cell-Permeant Scramble Control Peptide-2 (TAT-Sc-2)

Plasmid-expressed Peptide Sequence:

Declustering Peptide-1 (DP-1)

Scramble Control Peptide-1 (Sc-1)

FIG. 8A
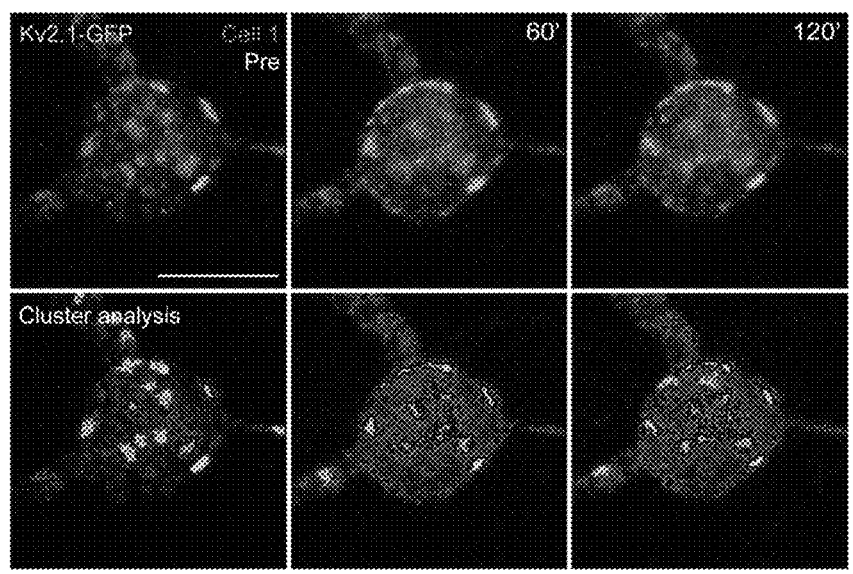
FIG. 8B
FIG. 8C
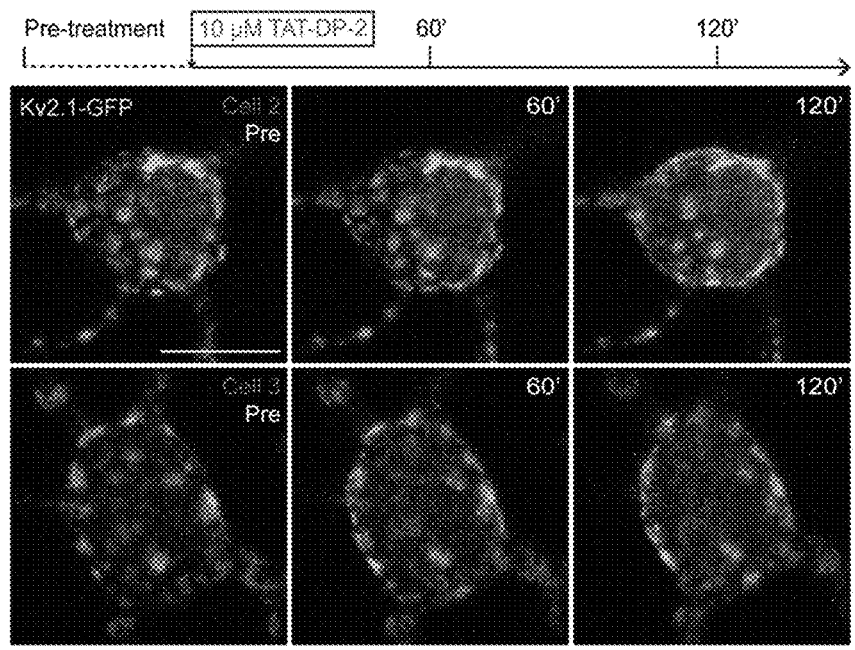
FIG. 8D
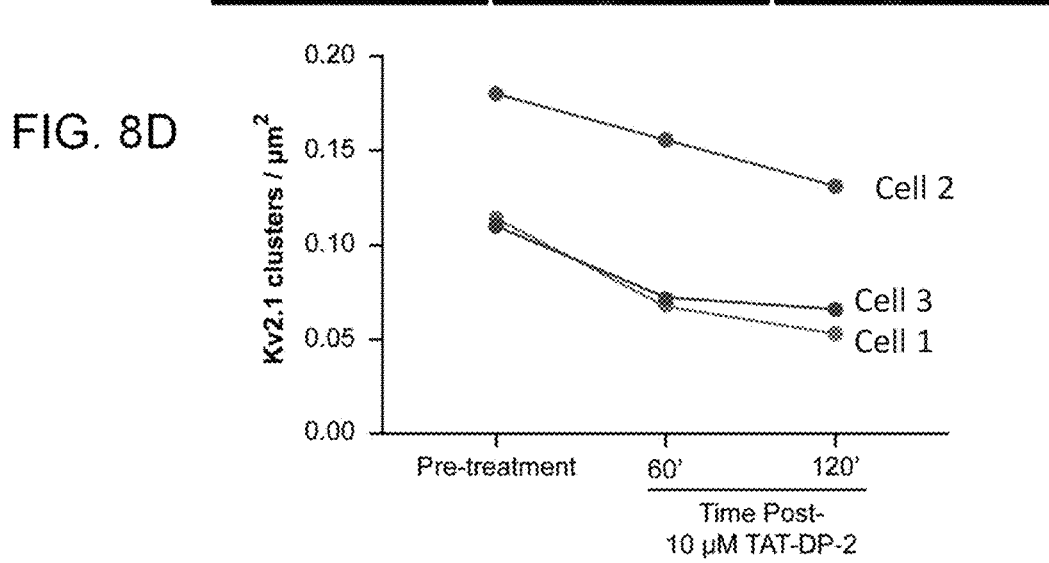

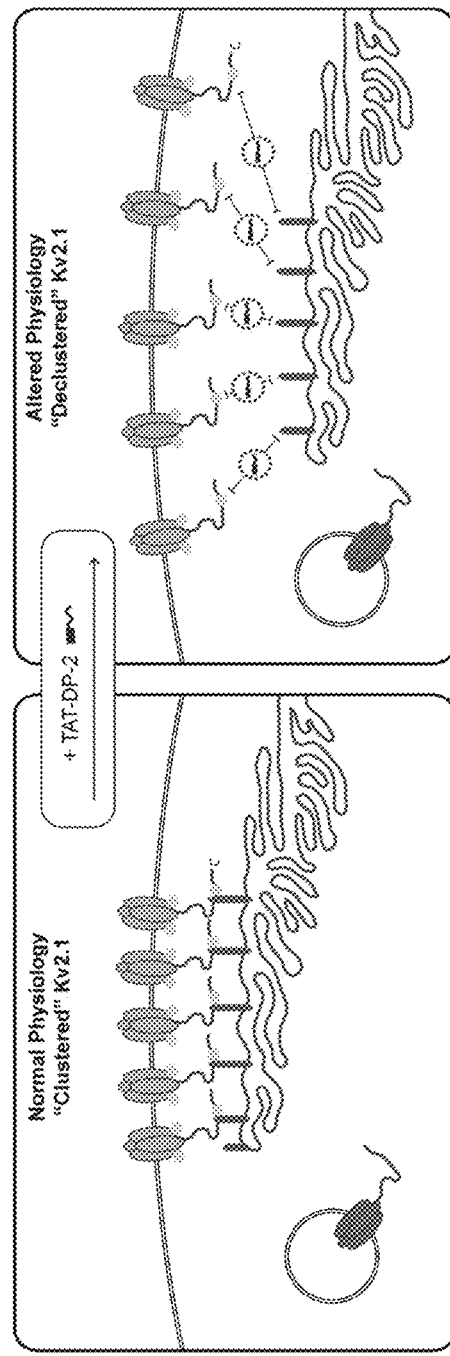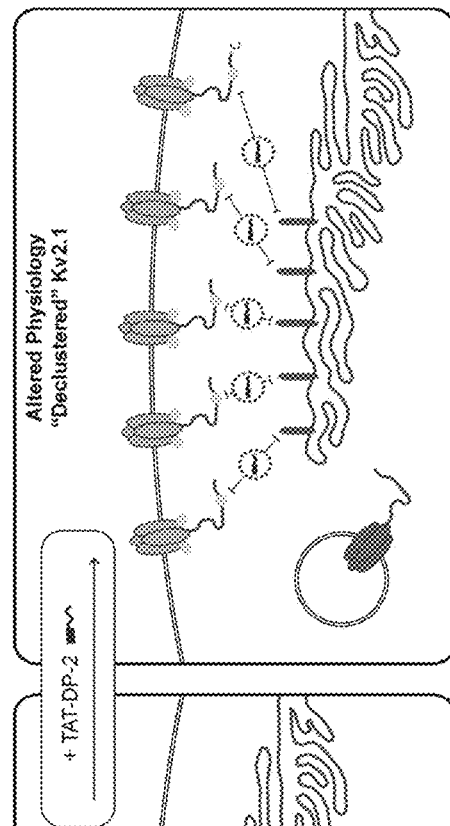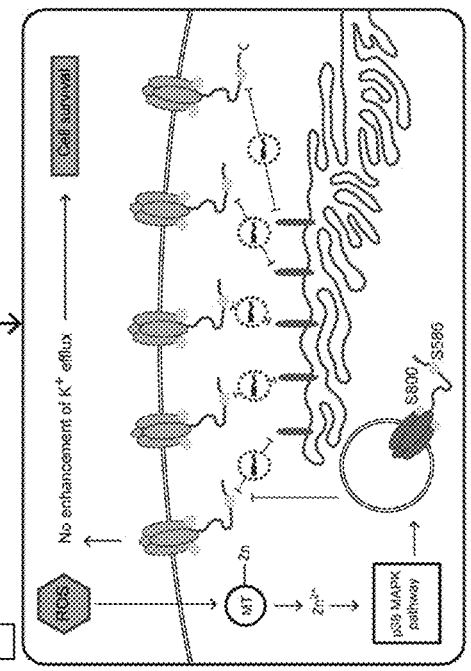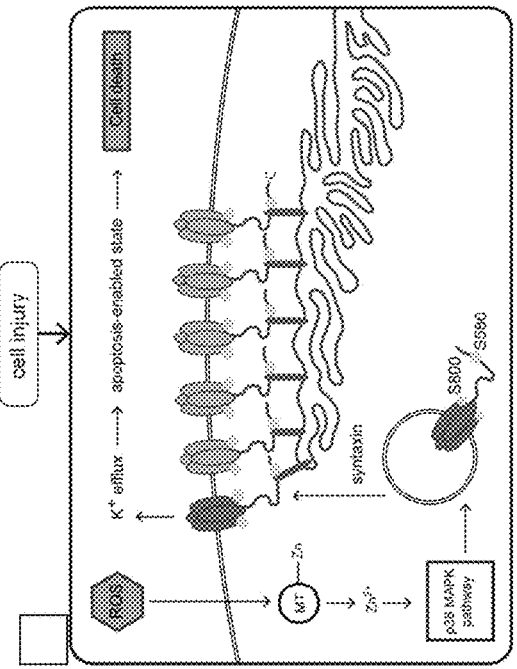

NEUROPROTECTIVE PEPTIDES AND METHODS OF THEIR USE

CROSS REFERENCE TO RELATED APPLICATIONS

This application claims the benefit of U.S. Provisional Application No. 63/088,074, filed Oct. 6, 2020, which is herein incorporated by reference in its entirety.

ACKNOWLEDGMENT OF GOVERNMENT SUPPORT

This invention was made with government support under grant number NS043277 awarded by National Institutes of Health. The government has certain rights in the invention.

FIELD

This disclosure concerns peptides derived from the potassium channel Kv2.2 that promote neuroprotection by blocking pro-apoptotic channel membrane insertion of cognate channel Kv2.1. This disclosure further concerns use of the neuroprotective peptides for inhibiting or treating neuronal damage.

BACKGROUND

Stroke is the primary cause of serious long-term disability in the U.S. (George et al., *MMWR Morb Mortal Wkly Rep.* 66: 479-481, 2017). Ischemic stroke is the most common form—accounting for approximately 80% of all cases—and results in focal cerebral ischemia secondary to thromboembolic arterial occlusion. While thrombolytic therapy (e.g., rt-PA) and surgical endovascular interventions may allow for brain reperfusion following ischemia, no FDA-approved neuroprotective drugs are available with the capability to mitigate the irreversible neuronal cell loss commonly associated with this neurological disorder.

A hallmark of neuronal tissue damage following brain ischemia is the advent of excitotoxic injury and delayed apoptosis in the ischemic penumbra, a peri-infarct zone of collaterally perfused tissue surrounding the central necrotic core (Broughton et al., *Stroke.* 40: e331-9, 2009). A known key regulator of neuronal apoptosis is the delayed-rectifying voltage-gated potassium channel Kv2.1 (Pal et al., *J Neurosci.* 23: 4798-4802, 2003). Although this channel normally functions to modulate cell excitability (Murakoshi et al., *J Neurosci.* 19: 1728-1735, 1999; Guan et al., *J Physiol (Lond).* 591: 4807-4825, 2013), it also plays a key role in neuronal demise by allowing a loss of cytoplasmic potassium, optimizing intracellular conditions for programmed cell death (Pal et al., *J Neurosci.* 23: 4798-4802, 2003; Hughes et al., *J Biol Chem.* 272: 30567-30576, 1997; Yu et al., *Science.* 278: 114-117, 1997). Indeed, neurons with decreased functional expression of Kv2.1 are highly resistant to apoptotic stimuli (Pal et al., *J Neurosci.* 23: 4798-4802, 2003). Kv2.1-mediated pro-apoptotic potassium efflux arises solely from the de novo, syntaxin-dependent insertion of a reserve pool of channels into the plasma membrane three to five hours following insult (Pal et al., *J Neurosci.* 23: 4798-4802, 2003; Pal et al., *Cell Death Differ.* 13: 661-667, 2006; Yeh et al., *J Neurosci.* 37: 5648-5658, 2017; McCord et al., *J Physiol (Lond).* 592: 3511-3521, 2014; Yeh et al., *Proc Natl Acad Sci USA.* 116: 15696-15607, 2019), such that enhanced apoptosis-enabling potassium efflux is mediated always and solely by new Kv2.1 channels reaching the membrane (Pal et al., *J Neurosci.* 23: 4798-4802, 2003; Pal et al., *Cell Death Differ.* 13: 661-667, 2006). As a result, delayed pro-apoptotic Kv2.1 channel membrane-insertion likely facilitates incorporation of viable penumbral tissue into the expanding infarct core. Exploration of neuroprotective strategies that mitigate delayed apoptotic cell death by inhibiting pro-apoptotic Kv2.1 channel membrane insertion following cerebral ischemia are likely to address a critical clinical need to combat stroke-mediated neuronal damage.

Two separate membrane-bound populations of Kv2.1 exist in neurons: i. freely dispersed, conducting channels, which mediate canonical delayed-rectifier potassium currents that regulate neuronal excitability (Murakoshi et al., *J Neurosci.* 19: 1728-1735, 1999; Guan et al., *J Physiol (Lond).* 591: 4807-4825, 2013; O'Connell et al., *Proc Natl Acad Sci USA.* 107: 12351-12356, 2010), and ii. electrically-silent, micron-sized somatodendritic channel clusters (O'Connell et al., *Proc Natl Acad Sci USA.* 107: 12351-12356, 2010). This second, much larger population of clustered Kv2.1 channels forms plasma membrane-endoplasmic reticulum (ER-PM) junctions that function as scaffolding sites for ion channel trafficking to the membrane (Fox et al., *J Cell Sci.* 128: 2096-2105, 2015), facilitating surface delivery of new pro-apoptotic Kv2.1 channels (Justice et al., *Neuroscience.* 354: 158-167, 2017; Deutsch et al., *Mol Biol Cell.* 23: 2917-2929, 2012). Overexpression of the C-terminus of the cognate channel Kv2.2 (Kv2.2 CT) can disrupt Kv2.1 clusters without altering the biophysical properties of existing, active channels (Justice et al., *Neuroscience.* 354: 158-167, 2017; Bayer et al., *Neuroscience.* 217: 56-66, 2012), and block pro-apoptotic potassium channel membrane insertion, resulting in neuroprotection following oxidative insult (Justice et al., *Neuroscience.* 354: 158-167, 2017).

SUMMARY

Described herein is the identification of a peptide derived from the C-terminal region of the voltage-gated potassium channel Kv2.2 that induces declustering of the cognate potassium channel Kv2.1. Disruption of Kv2.1 clusters blocks pro-apoptotic de novo Kv2.1 potassium channel membrane insertion, prevents cytoplasmic ion loss, and preserves neuronal cell viability after apoptotic injury. Use of the peptides, such as cell-permeable forms of the peptides, for treating or inhibiting neuronal damage, such as neuronal damage cause by cerebral ischemia, is described.

Provided herein are isolated or recombinant neuroprotective peptides. In some embodiments, the amino acid sequence of the peptide includes at least seven amino acids from a C-terminal region of Kv2.2. In some examples, the amino acid sequence of the peptide possesses the native sequence of Kv2.2. In other examples, at least one serine residue of the peptide is phosphorylated or is a phosphomimetic (e.g., by substitution of a serine residue with aspartic acid or glutamic acid).

Also provided are fusion proteins that include a neuroprotective peptide disclosed herein and a cell-penetrating peptide (CPP). In some embodiments, the CPP is the trans-activator of transcription (TAT) peptide from HIV-1.

Further provided are nucleic acid molecules and vectors that encode a neuroprotective peptide or fusion protein disclosed herein. Also provided is an isolated host cell that includes a nucleic acid or vector disclosed herein, for example a cell that can be used for the production of recombinant peptides or fusion proteins.

Also provided are compositions that include a pharmaceutically acceptable carrier and a neuroprotective peptide, fusion protein, nucleic acid or vector disclosed herein.

A method of declustering Kv2.1 in a cell, such as a neuron, is further provided. In some embodiments, the method includes contacting the cell with a neuroprotective peptide or fusion protein disclosed herein.

Further provided are methods of treating or inhibiting neuronal damage in a subject. In some embodiments, the method includes administering to the subject a therapeutically effective amount of a neuroprotective peptide, fusion protein, nucleic acid molecule, vector or composition disclosed herein.

Methods of treating ischemic stroke in a subject are also provided. In some embodiments, the method includes administering to the subject a therapeutically effective amount of a neuroprotective peptide, fusion protein, nucleic acid molecule, vector or composition disclosed herein.

The foregoing and other objects and features of the disclosure will become more apparent from the following detailed description, which proceeds with reference to the accompanying figures.

BRIEF DESCRIPTION OF THE DRAWINGS

FIGS. 1A-1C: Plasmid-driven expression of DP-1 in cortical neurons induces Kv2.1 declustering. (FIG. 1A) Schematic indicating the promoter and active peptide for plasmids utilized in this study (Sc-1, SEQ ID NO: 28; DP-1, SEQ ID NO: 27). (FIG. 1B) Raw maximum-intensity projection (MAX-IP) confocal images of live cortical neurons co-transfected with GFP-tagged Kv2.1 (Kv2.1-GFP) and either pcDNA3-Vector, pCMV-Kv2.2CT, pCMV-Sc-1, and pCMV-DP-1 are displayed. Well-defined Kv2.1 surface clusters are visible in the vector-expressing neuron and dispersal of Kv2.1 to diffuse localization in neuron expressing DP-1. Scale bar=10 μm. (FIG. 1C) Histograms represent mean Kv2.1 surface cluster density (#Kv2.1 clusters/$\mu m^2$ of neuronal soma), displayed as mean+/−SEM (Vec, 0.16±0.03, n=7; Kv2.2 CT, 0.07±0.01, n=11; Sc-1, 0.14±0.03, n=7; DP-1, 0.04±0.01, n=11). Analyzed via one-way ANOVA with Bonferroni's MCT (Vec vs. Kv2.2 CT, p=0.0035; Sc-1 vs. DP-1, p=0.0014; Vec vs. DP-1, ***p=0.0001).

(FIG. 2A) Raw confocal images of live cortical neurons transfected with GFP-tagged Kv2.1 (Kv2.1-GFP) are displayed, following two-hour treatment with vehicle, TAT-Sc-2, or TAT-DP-2. TAT-linked peptide sequences are highlighted below each image (TAT-Sc-2, SEQ ID NO: 24; TAT-DP-2, SEQ ID NO: 23). Key residues for cluster formation are indicated by shading. Well-defined Kv2.1 surface clusters are present in the vehicle and TAT-Sc-2-treated neurons, and Kv2.1 is dispersed to diffuse localization in TAT-DP-2-treated neurons. Scale bar=10 μm. (FIG. 2B) Histograms represent mean Kv2.1 surface cluster density (#Kv2.1 clusters/$\mu m^2$ of neuronal soma), displayed as mean±SEM (Veh, 0.18±0.01, n=29; TAT-Sc-2 [3 μM], 0.15±0.01, n=13; TAT-DP-2 [3 μM], 0.07±0.02, n=14, TAT-Sc-2 [10 μM], 0.16±0.02, n=11, TAT-DP-2 [10 μM], 0.08±0.01, n=20). Analyzed via one-way ANOVA with Bonferroni's MCT (Veh vs. TAT-DP-2 [3 μM], *p=0.0004; Veh vs. TAT-DP-2 [10 μM], p<0.0001; TAT-Sc-2 [3 μM] vs. TAT-DP-2 [3 μM], ns p=0.1365; TAT-Sc-2 [10 μM] vs. TAT-DP-2 [10 μM], p=0.0052).

(FIG. 3A) Depiction of a proximity ligation assay (PLA) is shown, indicating that PLA probes detect association between two target proteins of interest within 40 nm of each other. (FIG. 3B) Raw confocal images (60×) of immunolabeled cortical neurons are displayed, following 2-hour treatment with either TAT-Sc-2 or TAT-DP-2. PLA puncta-TRITC fluorescence indicates areas of Kv2.1-VAPA interaction. Robust reduction in density of PLA puncta occurs following TAT-DP-2 treatment. Scale bar=10 μm. (FIG. 3C) Histograms represent PLA puncta per square micron of neuronal soma (#PLA puncta/sq. micron of cell soma) across four separate experiments. Data are displayed as means+/−SEM [Veh, 0.13+/−0.01 (n=22 neurons); TAT-Sc-2, 0.10+/−0.06 (n=15 neurons); TAT-DP-2 0.06+/−0.01 (n=30 neurons)]. Analyzed via Kruskal-Wallis with Dunn's MCT [Veh versus TAT-Sc-2, ns (P=0.48); Veh versus TAT-DP-2 (***P<0.0001); TAT-Sc-2 versus TAT-DP-2 (*P=0.019)].

(FIG. 4A) Histograms represent mean Kv2.1-mediated potassium current densities following a voltage step from −80 mV to 30 mV, measured by whole-cell voltage clamp. Current density measurements were performed 3-5 hours following two-hour treatment with vehicle (dH$_2$O), vehicle (dH$_2$O)+TBOA (60 μM), TAT-Sc-2 (10 μM), TAT-Sc-2 (10 μM)+TBOA (60 μM), TAT-DP-2 (10 μM), or TAT-DP-2 (10 μM)+TBOA (60 μM). Data are displayed as mean±SEM (vehicle (dH$_2$O), 86.53±14.01, n=17; vehicle (dH$_2$O)+TBOA (60 μM), 162.50±18.61, n=14; TAT-Sc-2 (10 μM), 71.42±10.27, n=16; TAT-Sc-2 (10 μM)+TBOA (60 μM), 130.80±9.43, n=14; TAT-DP-2 (10 μM), 66.86±4.76, n=14; TAT-DP-2 (10 μM)+TBOA (60 μM), 65.68±12.07, n=13). Analyzed via Kruskall-Wallis with Dunn's MCT (Veh vs. Veh+TBOA, p=0.0057; TAT-Sc-2 vs. TAT-Sc-2+TBOA, p=0.0032; TAT-DP-2 vs. TAT-DP-2+TBOA, ns p>0.9999). Representative current density traces are depicted above the bar graphs for each treatment condition. Scale bars=50 pA/pF, 50 ms. (FIG. 4B) Current density-voltage curves are displayed for all the treatment groups noted above; voltage steps were in 10 mV increments from a potential of −80 mV. (FIG. 4C) Experimental schematic is shown, indicating key experimental time-points for TAT-linked peptide treatment, excitotoxic TBOA treatment, and measurement of extracellular lactate dehydrogenase concentration (LDH assay) or confocal imaging. (FIG. 4D) Histograms represent mean relative toxicity values ([LDH]$_{TBOA}$/[LDH]$_{Veh}$) over five separate experiments, each performed in triplicate. Relative toxicity ratio is indirectly proportional to cell viability. A significant reduction in TBOA-mediated toxicity was observed following co-treatment with TAT-DP-2. Data are presented as mean±SEM (Veh, 1.84±0.19, n=7; TAT-Sc-2, 1.57±0.15, n=7; TAT-DP-2, 1.01±0.15, n=7). Analyzed via one-way ANOVA with Holm-Sidak's MCT (Veh vs. TAT-DP-2, **p=0.0047; TAT-Sc-2 vs. TAT-DP-2, *p=0.0276).

(FIG. 5A) Confocal images (60×) of 30 μm coronal mouse brain sections of superficial cortex are shown, following intraperitoneal injection of live mice with either TAT-Sc-2 (6 nmol/g; n=3 animals) or TAT-DP-2 (6 nmol/g; n=3 animals), sacrificed 2 hours post-injection. FITC fluorescence indicates immunolabeled endogenous Kv2.1 channels. Highly localized Kv2.1 surface clusters were preserved in brain tissue from animals injected with TAT-Sc-2 and Kv2.1 surface clusters were robustly dispersed following TAT-DP-2 injection. Scale bar=10 µm. (FIG. 5B) Identical, paired images to those in FIG. 5A are displayed, highlighting automated Kv2.1 cluster analysis. Areas of fluorescence intensity indicate cluster domains. (FIG. 5C) Zoomed images of single neurons from each treatment group are displayed, correlating with the boxes from the FIG. 5A. Scale bar=10 µm. (FIG. 5D) Histograms represent mean number Kv2.1 cluster density (#Kv2.1 clusters/image field) across three separate experiments, utilizing three separate mice per treatment group. Six separate brain slices were obtained and imaged from each mouse to yield 51-54 image fields per treatment group. Data are displayed as mean±SEM (TAT-Sc-2, 565.70±50.72, n=51 fields; TAT-DP-2, 301.10±39.60, n=54 fields). Analyzed via Mann-Whitney test (****$p<0.0001$).

(FIG. 6A) Experimental schematic is displayed, indicating key time-points for middle cerebral artery occlusion (MCAo) and peptide injection. (FIG. 6B) Depiction of infarct analysis is shown, showing anatomical location of 2 mm brain sections analyzed following MCAo and description of infarct ratio calculation. (FIG. 6C) Top panel: paired coronal brain sections from mice treated with either IP TAT-Sc-2 or IP TAT-DP-2 are displayed following 50 minutes left MCAo, TAT-linked peptide injection, and tetrazolium chloride staining. Red areas indicate viable tissue actively undergoing oxidation-reduction reactions; pale areas represent infarcted brain tissue. Bottom panel: Single sections (slice 2) are displayed from different mice following the same protocol to present an additional example of more robust infarct reduction. A significant reduction in infarct area was observed following treatment with IP TAT-DP-2. (FIG. 6D) Histograms represent mean total infarct ratio of animals following 50 minutes MCAo and injection with either IP TAT-Sc-2 or IP TAT-DP-2. Data are displayed as mean±SEM (IP TAT-Sc-2, 0.121±0.009, n=9 animals; IP TAT-DP-2, 0.071±0.020, n=8 animals). Analyzed via unpaired t-test (*$p=0.0335$). (FIG. 6E) Plots of objective murine neurological score (MNS) vs. time (days post-MCAo) are displayed for cohorts injected with either IP TAT-Sc-2 (blue; n=5 mice) or IP-TAT-DP-2 (green; n=8 mice) following 50 minutes left MCAo. MNS indicates blinded assessment of neurological function, where 0=no neurological deficit and 8=stroke-related death (Table 3). Analyzed via two-way ANOVA for peptide-treatment effect between groups (****$p=0.0007$).

(FIG. 7A) Schematic of Kv2.2 organization is displayed, highlighting the location of the proximal restriction and clustering (PRC) domain within the C-terminus. (FIG. 7B) Kv2.2 and Kv2.1 PRC domains (SEQ ID NO: 29 and SEQ ID NO: 30, respectively) are displayed demonstrating sequence homology. Key residues for Kv2.1 cluster formation and analogous residues within Kv2.2 are indicated by shading. Boxes indicate proposed VAP-interacting non-canonical FFAT motifs involved in Kv2.1 recruitment to endoplasmic reticulum-plasma membrane (ER-PM) domains. (FIG. 7C) Amino acid sequences for transactivator of transcription (TAT)-linked declustering peptide 2 (TAT-DP-2; SEQ ID NO: 23) and scramble control peptide (TAT-Sc-2; SEQ ID NO: 24) are displayed. (FIG. 7D) Expanded declustering peptide (DP-1) and scramble control (Sc-1) sequences (SEQ ID NO: 27 and SEQ ID NO: 28, respectively) are shown that include the first naturally occurring methionine, facilitating their insertion into plasmid vectors.

FIGS. 8A-8D: Time-course of Kv2.1 cluster dispersal in vitro. (FIG. 8A) Raw confocal images of a live cortical neuron in vitro are shown, previously transfected with a GFP-tagged Kv2.1 construct (Kv2.1-GFP). Paired images are displayed demonstrating Kv2.1 channel cluster distribution before, 60 minutes, and 120 minutes post-TAT-DP-2 (10 µM) treatment. Scale bar=10 µm. (FIG. 8B) Top: Automated cluster analysis is displayed. Areas of fluorescence intensity indicate Kv2.1 cluster domains. Bottom: experimental timeline is illustrated. (FIG. 8C) Two additional examples of paired images are displayed, before and after TAT-DP-2 treatment as in FIG. 8A. (FIG. 8D) Plots of Kv2.1 cluster density (#Kv2.1 clusters/µm$^2$ of soma) are displayed for each cell.

(FIG. 10A) Raw confocal images of fixed cortical neurons are displayed, immunostained with an anti-Kv2.1 antibody and fluorescent secondary antibody (Alexa Fluor 568), following three-hour treatment with either TAT-Sc-2 (10 µM) or TAT-DP-2 (10 µM), in order to visualize the distribution of endogenous Kv2.1 channels. The data was collected from 4 replicate experiments; the representative images are from the same replicate. Scale bar=10 µm. (FIG. 10B) Histograms represent mean Kv2.1 surface cluster density (#Kv2.1 clusters/µm$^2$ of neuronal soma), displayed as mean±SEM (TAT-Sc-2 [10 µM], 0.056±0.005, n=32; TAT-DP-2 [10 µM], 0.030±0.003, n=33). Analyzed via unpaired t-test, two-tailed (****$p<0.0001$).

(FIG. 11A) Results of peptide-spot far western assay are displayed. Histograms represent average binding intensity of various peptides to plated VAPA proteins. The peptides shown in FIG. 11A are (left to right on x-axis) SEQ ID NOs: 1, 35, 44, 45, 46, 47, 48, 49, 50, 51, 52, 2, 3, 4, 5, 6, 7, 8, 9, 10, 11, 12, 13, 14, 15, 16, 17, 18, 19, 20, 21, 22, 53, 54, 55, 56, 57, 58, 59, 60, 61, 62, 34, 63, 64, 65, 66, 67, 68, 69, 70, 71, 72, 73, 74, 75, 76, 77, 78, 79, 80, 81, 82, 83, 84, 85, 86, 36, 87, 88, 89, 90, 91, 92, 93, 94, 95, 96, 97, 98, 99, 100, 101. Membrane inlays show co-localization binding signal for peptide variants that showed interaction with VAPA. (FIG. 11B) Histograms represent mean Kv2.1 surface cluster density (#Kv2.1 clusters/µm$^2$ of neuronal soma), measured following 2 hour treatment of cortical neurons with vehicle (dH$_2$O), TAT-FFATSc, or TAT-FFAT. Data are displayed as mean±SEM (Veh, 0.17±0.01, n=8; TAT-FFATSc [10 µM], 0.14±0.02, n=10; TAT-FFAT [10 µM], 0.15±0.03, n=10). Analyzed via one-way ANOVA with Bonferroni's MCT (Veh vs. TAT-FFAT [10 µM], ns $p=0.9757$; TAT-FFATSc [10 µM] vs. TAT-FFAT [10 µM], ns $p>0.9999$). (FIG. 11C) Histograms represent mean Kv2.1 surface cluster density (#Kv2.1 clusters/µm$^2$ of neuronal soma), measured following 24 hour treatment of cortical neurons with vehicle (dH$_2$O), TAT-FFATSc, or TAT-FFAT.

Data are displayed as mean±SEM (Veh, 0.20±0.02, n=10; TAT-FFATSc [10 μM], 0.20±0.01, n=10; TAT-FFAT [10 μM], 0.19±0.02, n=10). Analyzed via one-way ANOVA with Bonferroni's MCT (Veh vs. TAT-FFAT [10 μM], ns p=0.7859; TAT-FFATSc [10 μM] vs. TAT-FFAT [10 μM], ns p>0.9999).

Figure 12A:
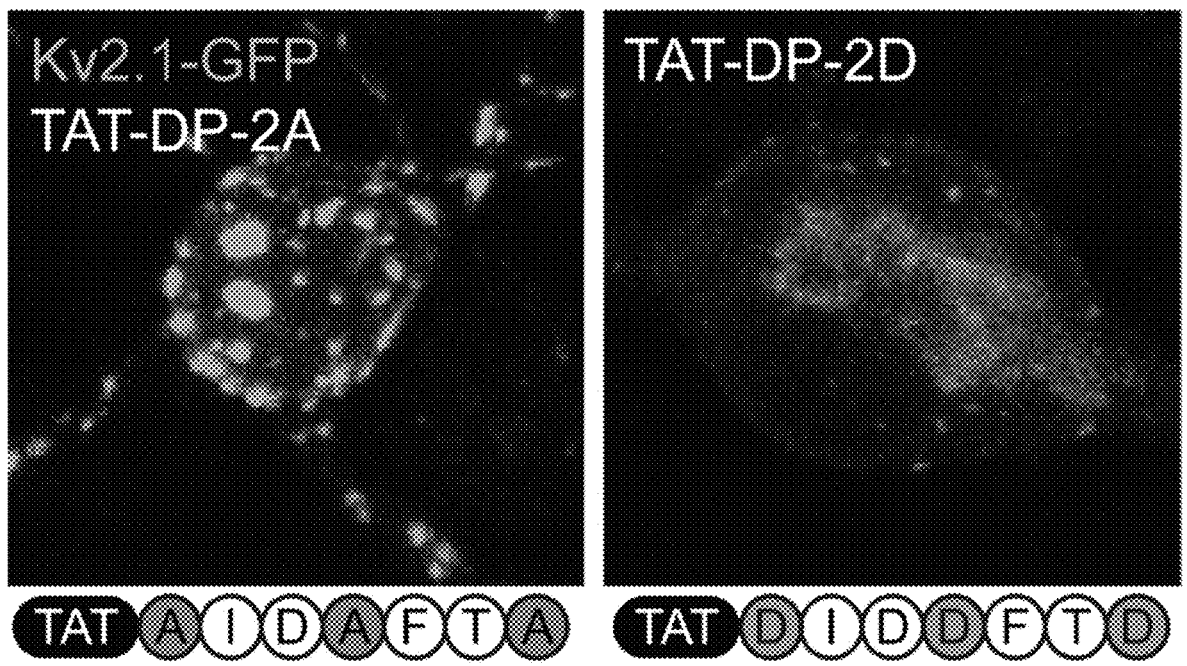
Figure 12B:
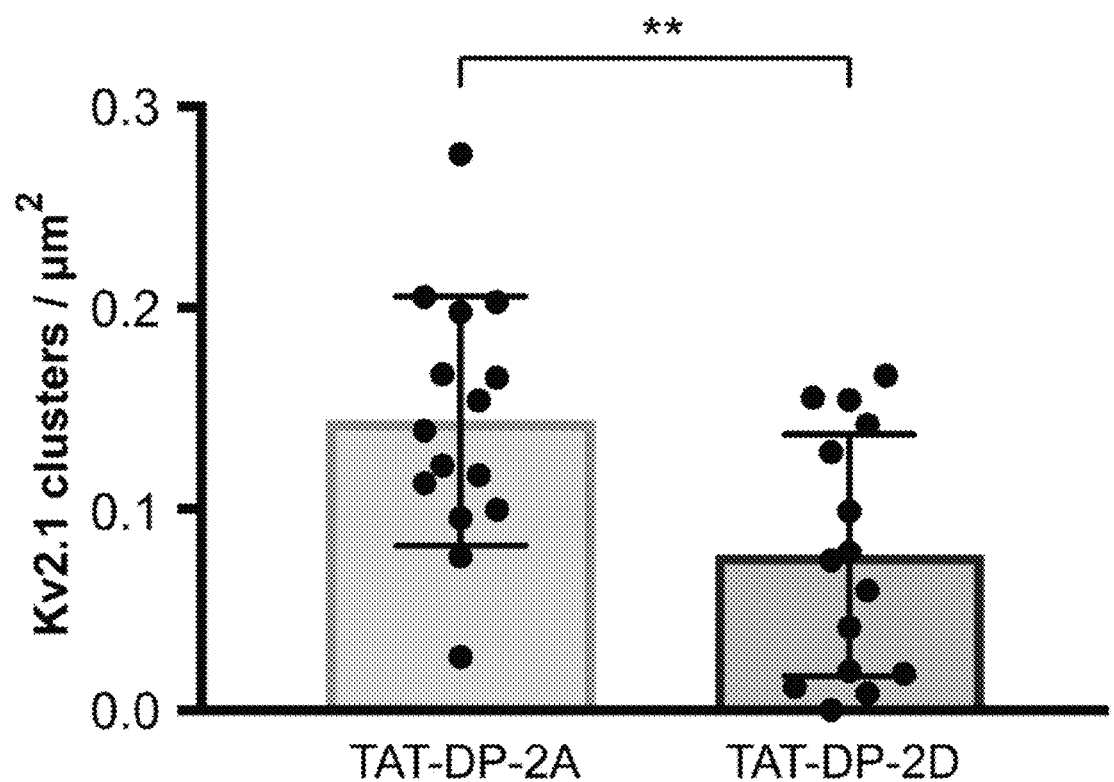

FIGS. 12A-12B: Serine phosphorylation is critical for TAT-DP-2-mediated Kv2.1 declustering in cortical neurons. (FIG. 12A) Raw maximum-intensity projection (MAX-IP) images of live neurons transfected with GFP-tagged Kv2.1 are displayed, following two-hour treatment with TAT-DP-2A or TAT-DP-2D (10 μM). TAT-linked peptide sequences are detailed below each image (TAT-DP-2A, SEQ ID NO: 25; TAT-DP-2D, SEQ ID NO: 26). Well-defined Kv2.1 surface clusters are observed in the TAT-DP-2A group and robust dispersal of Kv2.1 to diffuse localization is observed in TAT-DP-2D-treated neurons. Scale bar=10 μm. (FIG. 12B) Histograms represent mean Kv2.1 surface cluster density (#Kv2.1 clusters/μm$^2$ of neuronal soma), displayed as mean±SEM (TAT-DP-2A, 0.14±0.02, n=15 neurons; TAT-DP-2D, 0.08±0.02, n=15 neurons). Analyzed via unpaired t-test, two-tailed (**p=0.0057).

FIGS. 13A-13D: TAT-DP-2 induces rapid Kv2.1 declustering by disruption of Kv2.1-VAPA association at ER-PM junctions in neurons that prevents enhancement of pro-apoptotic Kv2.1 currents. (FIG. 13A) Current graphical model of Kv2.1 subcellular localization is depicted, showing the C-terminus of Kv2.1 potassium channels interacting with VAP proteins to form endoplasmic reticulum-plasma membrane (ER-PM) domains. (FIG. 13B) Cellular responses to injury (apoptotic injury, excitotoxicity, and ischemia) are displayed, showing signaling pathway that results in pro-apoptotic enhancement of Kv2.1 potassium currents and downstream cell death. Reactive oxygen species (ROS) production following injury causes displacement of intracellular zinc (Zn) from metallothionein (MT), leading to transient increases in intracellular free zinc concentrations ($Zn^{2+}$). This leads to activation of a dual p38-MAP-kinase pathway that results in phosphorylation and de novo syntaxin-dependent insertion of a reserve pool of Kv2.1 into the plasma membrane, likely at surface cluster domains, allowing for pro-apoptotic potassium efflux that sets the stage for programmed cell death. Kv2.1 surface cluster domains thus act as insertion platforms for pro-apoptotic Kv2.1 channel trafficking. (FIG. 13C) Proposed mechanism of action of TAT-DP-2 is displayed, showing interruption of Kv2.1-VAPA proteins localized to ER-PM junctions and concomitant disruption of Kv2.1 surface clusters, without direct TAT-DP-2 binding to VAPA proteins. (FIG. 13D) Proposed cellular response to injury in the context of TAT-DP-2 treatment is displayed, showing lack of de novo insertion of pro-apoptotic Kv2.1 potassium channels at the surface cluster domain due to lack of ER-PM association. This prevents enhancement of pro-apoptotic Kv2.1 potassium currents following cellular injury and provides robust neuroprotection.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 29, 2021, 69,932 bytes, which is incorporated by reference herein. In the accompanying sequence listing:

SEQ ID NO: 1 is the amino acid sequence of the DP-2 peptide.

SEQ ID NOs: 2-8 are amino acid sequences of Ser to Asp mutants of DP-2.

SEQ ID NOs: 9-15 are amino acid sequences of Ser to Glu mutants of DP-2.

SEQ ID NOs: 16-22 are amino acid sequences of Ser phosphorylation mutants of DP-2.

SEQ ID NO: 23 is the amino acid sequence of TAT-DP-2.

SEQ ID NO: 24 is the amino acid sequence of TAT-Sc-2.

SEQ ID NO: 25 is the amino acid sequence of TAT-DP-2A.

SEQ ID NO: 26 is the amino acid sequence of TAT-DP-2D.

SEQ ID NO: 27 is the amino acid sequence of plasmid expressed DP-1.

SEQ ID NO: 28 is the amino acid sequence of plasmid expressed Sc-1.

SEQ ID NO: 29 is the amino acid sequence of the PRC domain of Kv2.2.

SEQ ID NO: 30 is the amino acid sequence of the PRC domain of Kv2.1.

SEQ ID NO: 31 is the amino acid sequence of the TAT peptide.

SEQ ID NO: 32 is the amino acid sequence of rat Kv2.1 (Uniprot P15387):

```
MPAGMTKHGSRSTSSLPPEPMEIVRSKACSRRVRLNVGGLAHEVLWRTLD

RLPRTRLGKLRDCNTHDSLLQVCDDYSLEDNEYFFDRHPGAFTSILNFYR

TGRLHMMEEMCALSFSQELDYWGIDEIYLESCCQARYHQKKEQMNEELKR

EAETLREREGEEFDNTCCAEKRKKLWDLLEKPNSSVAAKILAIISIMFIV

LSTIALSLNTLPELQSLDEFGQSTDNPQLAHVEAVCIAWFTMEYLLRFLS

SPKKWKFFKGPLNAIDLLAILPYYVTIFLTESNKSVLQFQNVRRVVQIFR

IMRILRILKLARHSTGLQSLGFTLRRSYNELGLLILFLAMGIMIFSSLVF

FAEKDEDDTKFKSIPASFWWATITMTTVGYGDIYPKTLLGKIVGGLCCIA

GVLVIALPIPIIVNNFSEFYKEQKRQEKAIKRREALERAKRNGSIVSMNM

KDAFARSIEMMDIVVEKNGESIAKKDKVQDNHLSPNKWKWTKRALSETSS

SKSFETKEQGSPEKARSSSSPQHLNVQQLEDMYSKMAKTQSQPILNTKEM

APQSKPPEELEMSSMPSPVAPLPARTEGVIDMRSMSSIDSFISCATDFPE

ATRFSHSPLASLSSKAGSSTAPEVGWRGALGASGGRLTETNPIPETSRSG

FFVESPRSSMKTNNPLKLRALKVNFVEGDPTPLLPSLGLYHDPLRNRGGA

AAAVAGLECASLLDKPVLSPESSIYTTASARTPPRSPEKHTAIAFNFEAG

VHHYIDTDTDDEGQLLYSVDSSPPKSLHGSTSPKFSTGARTEKNHFESSP

LPTSPKFLRPNCVYSSEGLTGKGPGAQEKCKLENHTPPDVHMLPGGGAHG

STRDQSI
```

SEQ ID NOs: 33 and 34 are the amino acid sequences of FFAT motif sequences.

SEQ ID NO: 35 is the amino acid sequence of the Sc-2 peptide.

SEQ ID NO: 36 is the amino acid sequence of a canonical FFAT motif.

SEQ ID NO: 37 is the amino acid sequence of TAT-FFAT.

SEQ ID NO: 38 is the amino acid sequence of scramble control peptide TAT-FFATSc.

SEQ ID NO: 39 is the amino acid sequence of mouse Kv2.1 (Uniprot Q03717):

MPAGMTKHGSRSTSSLPPEPMEIVRSKACSRRVRLNVGGLAHEVLWRTLD

RLPRTRLGKLRDCNTHDSLLQVCDDYSLEDNEYFFDRHPGAFTSILNFYR

TGRLHMMEEMCALSFSQELDYWGIDEIYLESCCQARYHQKKEQMNEELKR

EAETLREREGEEFDNTCCAEKRKKLWDLLEKPNSSVAAKILAIISIMFIV

LSTIALSLNTLPELQSLDEFGQSTDNPQLAHVEAVCIAWFTMEYLLRFLS

SPKKWKFFKGPLNAIDLLAILPYYVTIFLTESNKSVLQFQNVRRVVQIFR

IMRILRILKLARHSTGLQSLGFTLRRSYNELGLLILFLAMGIMIFSSLVF

FAEKDEDDTKFKSIPASFWWATITMTTVGYGDIYPKTLLGKIVGGLCCIA

GVLVIALPIPIIVNNFSEFYKEQKRQEKAIKRREALERAKRNGSIVSMNM

KDAFARSIEMMDIVVEKNGEGVAKKDKVQDNHLSPNKWKWTKRALSETSS

SKSFETKEQGSPEKARSSSSPQHLNVQQLQDMYSKMAKTQSQPILNTKEM

APQSQPQEELEMGSMPSPVAPLPTRTEGVIDMRSMSSIDSFISCATDFPE

ATRFSHSPLASLSGKSGGSTAPEVGWRGALGASGGRLMETNPIPEASRSG

FFVESPRSSMKTHNPMKLRALKVNFLEGDPTPLLPALGLYHDPLRNRGGA

AAAVAGLECASLLDKPVLSPESSIYTTASARTPPRSPEKHTAIAFNFEAG

VHQYIDTDTDDEGQLLYSVDSSPPKSLHGSTSPKFSLGARTEKNHFESSP

LPTSPKFLRPNCVYASEGLPGKGPGAQEKCKLENHTSPDVHMLPGGGAHG

STRDQSI

SEQ ID NO: 40 is the amino acid sequence of mouse Kv2.2 (Uniprot A6H8H5).

SEQ ID NO: 41 is the amino acid sequence of human Kv2.1 (Uniprot Q14721):

MPAGMTKHGSRSTSSLPPEPMEIVRSKACSRRVRLNVGGLAHEVLWRTLD

RLPRTRLGKLRDCNTHDSLLEVCDDYSLDDNEYFFDRHPGAFTSILNFYR

TGRLHMMEEMCALSFSQELDYWGIDEIYLESCCQARYHQKKEQMNEELKR

EAETLREREGEEFDNTCCAEKRKKLWDLLEKPNSSVAAKILAIISIMFIV

LSTIALSLNTLPELQSLDEFGQSTDNPQLAHVEAVCIAWFTMEYLLRFLS

SPKKWKFFKGPLNAIDLLAILPYYVTIFLTESNKSVLQFQNVRRVVQIFR

IMRILRILKLARHSTGLQSLGFTLRRSYNELGLLILFLAMGIMIFSSLVF

FAEKDEDDTKFKSIPASFWWATITMTTVGYGDIYPKTLLGKIVGGLCCIA

GVLVIALPIPIIVNNFSEFYKEQKRQEKAIKRREALERAKRNGSIVSMNM

KDAFARSIEMMDIVVEKNGENMGKKDKVQDNHLSPNKWKWTKRTLSETSS

SKSFETKEQGSPEKARSSSSPQHLNVQQLEDMYNKMAKTQSQPILNTKES

AAQSKPKEELEMESIPSPVAPLPTRTEGVIDMRSMSSIDSFISCATDFPE

ATRFSHSPLTSLPSKTGGSTAPEVGWRGALGASGGRFVEANPSPDASQHS

SFFIESPKSSMKTNNPLKLRALKVNFMEGDPSPLLPVLGMYHDPLRNRGS

AAAAVAGLECATLLDKAVLSPESSIYTTASAKTPPRSPEKHTAIAFNFEA

GVHQYIDADTDDEGQLLYSVDSSPPKSLPGSTSPKFSTGTRSEKNHFESS

-continued

PLPTSPKFLRQNCIYSTEALTGKGPSGQEKCKLENHISPDVRVLPGGGAH

GSTRDQSI

SEQ ID NO: 42 is the amino acid sequence of human Kv2.2 (Uniprot Q92953).

SEQ ID NO: 43 is the amino acid sequence of rat Kv2.2 (Uniprot Q63099).

SEQ ID NO: 44 is the amino acid sequence of the pSc-2 peptide.

SEQ ID NOs: 45-52 are amino acid sequences of Ser to Ala mutants of DP-2.

SEQ ID NOs: 53-62 are amino acid sequences of DP-2 permutations and/or expansions.

SEQ ID NOs: 63-71 are amino acid sequences of VAP BD permutations.

SEQ ID NOs: 72-86 are amino acid sequences of other PRC sequences.

SEQ ID NOs: 87-101 are amino acid sequences of analogous Aplysia Kv2.1 sequences.

DETAILED DESCRIPTION

I. Abbreviations

CT C-terminal
DIV days in vitro
DP declustering peptide
ER-PM endoplasmic reticulum-plasma membrane
FFAT two-phenylalanine in an acidic tract
FITC fluorescein isothiocyanate
GFP green fluorescent protein
IP intraperitoneal
LDH lactate dehydrogenase
MCAo middle cerebral artery occlusion
MCT multiple comparison test
MNS murine neurological score
NGS normal goat serum
PFA paraformaldehyde
PLA proximity ligation assay
PRC proximal restriction and clustering
ROI region of interest
TAT transactivator of transcription
TBOA DL-threo-β-benzyloxyaspartic acid
VAMP vesicle-associated molecular protein
VAP vesicle-associated membrane protein-associated protein
VAPA VAMP-associated protein A II. Terms and Methods Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administer: As used herein, administering a composition (e.g. a polypeptide) to a subject means to give, apply or bring the composition into contact with the subject. Administration can be accomplished by any of a number of routes, such as, for example, intravenous, intrathecal, topical, oral, subcutaneous, intranasal, intraperitoneal, intramuscular or by direct injection into a tissue.

Cell-penetrating peptide (CPP): Peptides that facilitate the cellular uptake of another protein or molecular cargo linked by a covalent bond or non-covalent interaction. CPPs generally deliver cargo into a cell by endocytosis. In many instances, CPPs have an amino acid composition that is rich in charged amino acids, such as lysine or arginine, or have sequences that contain an alternating pattern of polar/charged amino acids and non-polar/hydrophobic amino acids. In some embodiments herein, the CPP is the transactivator of transcription (TAT) peptide from HIV-1 (set forth herein as SEQ ID NO: 31).

Cerebral ischemia or ischemic stroke: A condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes.

Contacting: Placement in direct physical association; includes both in solid and liquid form.

Declustering of Kv2.1: Disruption or dispersal of Kv2.1 channel clusters. In neurons, membrane-bound Kv2.1 exists as two separate populations: (1) freely dispersed, conducting channels, which mediate delayed-rectifier potassium currents that regulate neuronal excitability (Murakoshi et al., *J Neurosci*. 19: 1728-1735, 1999; Guan et al., *J Physiol (Lond)*. 591: 4807-4825, 2013; O'Connell et al., *Proc Natl Acad Sci USA*. 107: 12351-12356, 2010); and (2) electrically-silent, micron-sized somatodendritic channel clusters (O'Connell et al., *Proc Natl Acad Sci USA*. 107: 12351-12356, 2010). "Declustering of Kv2.1" therefore refers to dispersal of the channel clusters of population (2), resulting in the freely dispersed, but still non-conducting channels of population (2).

Fusion protein: A protein containing amino acid sequence from at least two different (heterologous) proteins or peptides. In some examples herein, the fusion protein comprises a portion of a Kv2.2 protein and a cell-penetrating peptide. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species.

Ischemia: A vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply.

Isolated: An "isolated" biological component (such as a nucleic acid molecule, protein, or cell) has been substantially separated or purified away from other biological components in the cell, blood or tissue of the organism, or the organism itself, in which the component occurs. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Kv2.1: A voltage-dependent delayed-rectifier $K^+$ channel belonging to the 6-transmembrane family of potassium channels. In humans, Kv2.1 is encoded by the KCNB1 (potassium voltage-gated channel subfamily B member 1) gene. The pore-forming alpha subunits contain a single pore-forming region and combine to form tetramers. Heterotrimeric channels can be formed within subfamilies (e.g., Kv1.1 with Kv1.2). Kv2.1 is involved in the regulation of high-frequency repetitive firing (Pongs, *FEBS Lett* 452, 31-35, 1999; Du et al., *J Physiol* 522, 19-31, 2000; Guan et al., *J Physiol* 591, 4807-4825, 2013), and acts as the primary conduit for $K^+$ efflux during apoptotic cell death in neocortical and hippocampal neurons (Pal et al., *J Neurosci* 23, 4798-4802, 2003; Shen et al., *J Neurosci Res* 87, 3153-3160, 2009). Mouse, human and rat sequences for Kv2.1 are known and publicly available, such as those deposited under Uniprot Q03717 (mouse; SEQ ID NO: 39), Uniprot Q14721 (human; SEQ ID NO: 41) and Uniprot P15387 (SEQ ID NO: 32).

Kv2.2: A voltage-gated potassium channel belonging to the 6-transmembrane family of potassium channels. In humans, Kv2.2 is encoded by the KCNB2 (potassium voltage-gated channel subfamily B member 2) gene. Kv2.2, along with Kv2.1, is a major constituent of the somatic delayed rectifier potassium current, and is believed to be important in determining the overall excitability of small populations of neurons. Kv2.2, in contrast to Kv2.1, does not facilitate neuronal apoptosis. Human, mouse and rat sequences for Kv2.2 are known and publicly available such as those deposited under Uniprot Q92953 (human; SEQ ID NO: 42), Uniprot A6H8H5 (mouse; SEQ ID NO: 40) and Uniprot Q63099 (rat; SEQ ID NO: 43).

Neurodegenerative disorder or disease: Refers to any type of disorder or disease that is associated with a progressive loss of motor, sensory and/or perceptual functions, and often involves behavioral and cognitive deficits. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

Neuronal damage: Damage to the neurons, such as the neurons of the CNS. In particular embodiments herein, the neuronal damage is in the brain. Neuronal damage can be caused by a variety of conditions and events, such as ischemic stroke, hemorrhagic stroke or brain injury, such as traumatic brain injury. In some examples of the present disclosure, the neuronal damage is caused by an acute condition, such as a stroke.

Neuroprotective: An agent (such as a peptide) that is capable of protecting nerve cells from damage, degeneration or impairment of function.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 22nd Edition, 2013, describes compositions and formulations suitable for pharmaceutical delivery of polypeptides.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Polypeptide or peptide: A polymer in which the monomers are amino acid residues which are joined together through amide bonds. When the amino acids are alpha-amino acids, either the L-optical isomer or the D-optical isomer can be used. The terms "polypeptide," "peptide" or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A region of DNA that directs/initiates transcription of a nucleic acid (e.g. a gene). A promoter includes necessary nucleic acid sequences near the start site of transcription. Typically, promoters are located near the genes they transcribe. A promoter also optionally includes distal enhancer or repressor elements that can be located as much as several thousand base pairs from the start site of transcription.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

Stroke: The sudden death of brain cells due to a lack of oxygen when the blood flow to the brain is impaired by blockage or rupture of an artery to the brain. Ischemic stroke refers to a condition that occurs when an artery to or in the brain is partially or completely blocked such that the oxygen demand of the tissue exceeds the oxygen supplied. Deprived of oxygen and other nutrients following an ischemic stroke, the brain suffers damage as a result of the stroke. Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of ischemic stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Hemorrhagic stroke is another kind of stroke that results from an accumulation of blood in or around the brain, such as from a ruptured blood vessel. Hemorrhages in the brain can be caused by a variety of disorders that affect the blood vessels, such as long-term high blood pressure and cerebral aneurysms (a week or thin spot on a blood vessel wall).

Subject: Living multi-cellular vertebrate organisms, a category that includes both human and veterinary subjects, including human and non-human mammals (including research subjects such as rodents). A subject is also referred to herein as a "patient."

Synthetic: Produced by artificial means in a laboratory, for example a synthetic polypeptide can be chemically synthesized in a laboratory.

Therapeutically effective amount: A quantity of compound or composition, for instance, a neuroprotective peptide, sufficient to achieve a desired effect in a subject being treated. For instance, this can be the amount necessary to reduce the infarct area of a subject who has suffered from a stroke. In one embodiment, a therapeutically effective amount is the amount necessary to reduce the infarct area by at least 10%, at least 20%, at least 50%, at least 75%, at least 80%, at least 90%, at least 95%, or even 100%, for example as compared to prior to treatment. When administered to a subject, a dosage will generally be used that will achieve target tissue concentrations (for example, in the brain) that have been shown to achieve a desired in vitro effect.

Traumatic brain injury (TBI): A form of acquired brain injury that occurs when a sudden trauma causes damage to the brain. TBI can result when the head suddenly and violently hits an object, or when an object pierces the skull and enters brain tissue. Symptoms of a TBI can be mild, moderate, or severe, depending on the extent of the damage to the brain. A person with a mild TBI may remain conscious or may experience a loss of consciousness for a few seconds or minutes. Other symptoms of mild TBI include headache, confusion, lightheadedness, dizziness, blurred vision or tired eyes, ringing in the ears, bad taste in the mouth, fatigue or lethargy, a change in sleep patterns, behavioral or mood changes, and trouble with memory, concentration, attention, or thinking. A person with a moderate or severe TBI may show these same symptoms, but may also have a headache that gets worse or does not go away, repeated vomiting or nausea, convulsions or seizures, an inability to awaken from sleep, dilation of one or both pupils of the eyes, slurred speech, weakness or numbness in the extremities, loss of coordination, and increased confusion, restlessness, or agitation.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

III. Introduction

Kv2.1 channels are critical mediators of the cell death-enabling loss of cytosolic potassium in neurons. Following lethal stimuli, Kv2.1 channels are inserted de novo in the plasma membrane at specialized VAP-associated somatodendritic Kv2.1 surface clusters acting as membrane trafficking sites. In vitro overexpression of the C-terminus (CT) of the cognate channel Kv2.2 disrupts Kv2.1 surface clusters and provides neuroprotective blockade of Kv2.1-mediated increases in potassium currents underlying the cellular loss of the cation. The present disclosure identifies a seven amino acid declustering domain within Kv2.2 CT (DP-2) and demonstrates its neuroprotective efficacy as an injectable therapeutic in a murine model of ischemic stroke. A membrane-permeable derivative of DP-2 (TAT-DP-2) rapidly induces Kv2.1 surface cluster dispersal, preventing pro-apoptotic Kv2.1 potassium channel membrane insertion, and preserving cell viability after apoptotic injury in rat cortical neurons in vitro. A proximity ligation assay was used to show that TAT-DP-2 acts by disrupting the association of Kv2.1 with VAPA. It is also demonstrated that TAT-DP-2 induces rapid cerebrocortical Kv2.1 surface cluster dispersal in vivo following intraperitoneal injection into mice, reduces infarct size and improves long-term neurological function following transient middle cerebral artery occlusion. Together, these data indicate that TAT-DP-2 induces Kv2.1 declustering in neurons by disrupting Kv2.1-VAPA association, leading to the loss of scaffolding sites required for the death-enabling membrane-insertion of Kv2.1 channels following injury. Thus, the present disclosure provides the first evidence of targeted disruption of Kv2.1-VAPA association as a highly effective neuroprotective therapeutic strategy.

IV. Overview of Several Embodiments

Described herein is the identification of a peptide derived from the C-terminal region of the voltage-gated potassium channel Kv2.2 that induces declustering of the cognate potassium channel Kv2.1. Disruption of Kv2.1 clusters blocks pro-apoptotic potassium current enhancement, and preserves neuronal cell viability after apoptotic injury. Use of the peptides, such as cell-permeable forms of the peptides, for treating or inhibiting neuronal damage, such as neuronal damage cause by cerebral ischemia, is described.

Disclosed herein are isolated or recombinant neuroprotective peptides that include a 7-amino acid fragment of the Kv2.2 protein (residues 602-608 of human Kv2.2 set forth as SEQ ID NO: 42), or a modified form thereof. In some embodiments, the peptide is not modified and includes the sequence SIDSFTS (SEQ ID NO: 1). In other embodiments, the peptide is modified to include one or more phosphorylated residues or pseudophosphorylated resides. In some examples, the peptide includes SEQ ID NO: 1, wherein the serine at position 1, 4 and/or 7 is replaced with aspartic acid. In other examples, the peptide includes SEQ ID NO: 1, wherein the serine at position 1, 4 and/or 7 is replaced with glutamic acid. In other examples, the peptide includes SEQ ID NO: 1, wherein the serine at position 1, 4 and/or 7 is phosphorylated. The present disclosure also contemplates a combination of serine to aspartic acid, serine to glutamic acid, and serine phosphorylated residues at positions 1, 4 and/or 7 of SEQ ID NO: 1. Thus, in other other examples, the peptide includes SEQ ID NO: 1, wherein at least one serine is substituted with aspartic acid and at least one serine is substituted with glutamic acid; or at least one serine is substituted with aspartic acid and at least one serine is phosphorylated; or at least one serine is replaced with glutamic acid and at least one serine is phosphorylated.

In some embodiments, the neuroprotective peptide includes at least 8, at least 9, at least 10, at least 11, at least 12, at least 13, at least 14, at least 15, at least 16, at least 17, at least 18, at least 19, or 20 amino acids of the Kv2.2 protein, or a modified form thereof. In some examples, the Kv2.2 protein is the human protein set forth as SEQ ID NO: 42. In other embodiments, the Kv2.2 protein is the mouse protein set forth as SEQ ID NO: 40. In yet other embodiments, the Kv2.2 protein is the rat protein set forth as SEQ ID NO: 43.

In some embodiments, the peptide is no more than 20, no more than 15, no more than 10 or no more than 7 amino acids in length. In some examples, the peptide is 7, 8, 9, 10, 11, 12, 13, 14, 15, 16, 17, 18, 19 or 20 residues in length.

In some embodiments, the neuroprotective peptide is up to 20 amino acids in length and includes the amino acid sequence of any one of SEQ ID NOs: 1-22. In some examples, the peptide is up to 15 amino acids in length and includes the amino acid sequence of any one of SEQ ID NOs: 1-22. In some examples, the peptide is up to 12 amino acids in length and includes the amino acid sequence of any one of SEQ ID NOs: 1-22. In particular examples, the peptide is 7 seven amino acids in length and the sequence of the peptide consists of any one of SEQ ID NOs: 1-22. In another particular example, the peptide is 12 amino acids in length and the sequence of the peptide consists of SEQ ID NO: 27.

Also provided are fusion proteins that include a neuroprotective peptide disclosed herein and a heterologous protein or peptide. In some embodiments, the heterologous peptide is a cell-penetrating peptide (CPP).

CPPs are a family of polypeptides that facilitate transduction of proteins, nucleic acids or other compounds across membranes in a receptor-independent manner (Wadia and Dowdy, Curr. Protein Pept. Sci. 4(2):97-104, 2003; Meloni et al., Front Neurol 11:108, 2020). Typically, CPPs are short polycationic sequences that can facilitate cellular uptake of compounds to which they are linked into endosomes of cells.

The capacity of certain peptides to deliver proteins or nucleic acids into cells was originally described for the HIV-encoded Tat protein, which was shown to cross membranes and initiate transcription. It was then discovered that the portion of the Tat protein that was required for the transduction of the protein was only an 11 amino acid polypeptide, referred to as the Tat peptide (YGRKKRRQRRR; SEQ ID NO: 31). When fused with other proteins, the Tat peptide has been demonstrated to deliver these proteins, varying in size from 15 to 120 kDa, into cells in tissue culture and into brain cells in vivo (Frankel and Pabo, Cell 55(6):1189-93, 1988; Green and Loewenstein, J. Gen. Microbiol. 134(3):849-55, 1988; Vives et al., J. Biol. Chem. 272(25):16010-7, 1997; Yoon et al., J. Microbiol. 42(4):328-35, 2004; Cai et al., Eur. J. Pharm. Sci. 27(4):311-9, 2006).

Other known CPPs include PENETRATIN™, a 16 amino acid peptide derived from the third helix of the Drosophila Antennapedia homeobox gene (U.S. Pat. No. 5,888,762; Derossi et al., J. Biol. Chem. 269:10444-10450, 1994; Schwarze et al., Trends Pharmacol. Sci. 21:45-48, 2000); transportan, a 27 amino acid chimeric peptide comprised of 12 amino acids from the N-terminus of the neuropeptide galanin and the 14-amino acid protein mastoparan, connected via a lysine (U.S. Pat. No. 6,821,948; Pooga, FASEB J. 12:67-77, 1998; Hawiger, Curr. Opin. Chem. Biol. 3:89-94, 1999); peptides from the VP22 protein of herpes simplex virus (HSV) type 1 (Elliott et al., Cell 88:223-233, 1997); the UL-56 protein of HSV-2 (U.S. Patent Application Publication No. 2006/0099677); and the Vpr protein of HIV-1 (U.S. Patent Application Publication No. 2005/0287648). In addition, a number of artificial peptides also are known to function as CPPs, such as poly-arginine, poly-lysine and others (see, for example, U.S. Application Publication Nos. 2006/0106197; 2006/0024331; 2005/0287648; and 2003/0125242; Meloni et al., Front Neurol 11:108, 2020; Zhibao et al., Mol. Ther. 2:339-347, 2000; and Laus et al. Nature Biotechnol. 18:1269-1272, 2000).

In some examples, the CPP is the TAT peptide comprising or consisting of the amino acid sequence of SEQ ID NO: 31. In particular non-limiting examples, the amino acid sequence of the fusion protein comprises or consists of SEQ ID NO: 23 (TAT-DP-2), SEQ ID NO: 25 (TAT-DP-2A) or SEQ ID NO: 26 (TAT-DP-2D).

In some examples, the CPP is rich in charged amino acids, such as lysine or arginine. In other examples, the CPP contains an alternating pattern of polar/charged amino acids and non-polar/hydrophobic amino acids. In particular non-limiting examples, the CPP comprises poly-arginine, such as 6, 7, 8, 9, 10, 11 or 12 arginine residues. In other non-limiting examples, the CPP comprises poly-lysine, such as 6, 7, 8, 9, 10, 11 or 12 lysine residues.

In other embodiments, the heterologous protein or peptide is a protein tag, such as an affinity tag (for example, chitin binding protein, maltose binding protein, glutathione-S-transferase or poly-His), an epitope tag (for example, V5, c-myc, HA or FLAG) or a fluorescent tag (e.g., GFP or another well-known fluorescent protein).

Further provided herein are nucleic acid molecules encoding an isolated or recombinant neuroprotective peptide or fusion protein disclosed herein. In some embodiments, the nucleic acid molecule is operably linked to a heterologous promoter. Vectors that include a nucleic acid molecule disclosed herein are further provided. The vector can be, for example, a viral vector (e.g. a lentiviral vector, an adenovirus vector or an adeno-associated virus vector) or a plasmid expression vector.

Also provided are compositions that include a pharmaceutically acceptable carrier and the neuroprotective peptide, fusion protein, nucleic acid molecule or the vector disclosed herein.

Further provided are methods of declustering Kv2.1 in a cell. In some embodiments, the method includes contacting the cell with an isolated or recombinant neuroprotective peptide, fusion protein, isolated nucleic acid molecule, vector or composition disclosed herein. In some examples, the cell is a neuron. In some examples, the method is an in vitro method. In other examples, the method is an in vivo method and contacting the cell with the peptide, fusion protein, composition, nucleic acid molecule or vector includes administering the peptide, fusion protein, composition, nucleic acid molecule or vector to a subject, such as a subject suffering from cerebral ischemia, stroke, traumatic brain injury or a neurodegenerative disease, cardiac arrest, or epilepsy. In some examples, the neuroprotective peptide, fusion protein, isolated nucleic acid molecule, vector or composition disclosed herein is administered as a prophylactic medication prior to surgical intervention with risk for intraoperative stroke (e.g., carotid endarterectomy, endovascular aneurysm repair, open cerebrovascular aneurysm repair). In some examples, the neuroprotective peptide, fusion protein, isolated nucleic acid molecule, vector or composition disclosed herein is administered to a subject experiencing ischemia secondary to vasospasm after subarachnoid hemorrhage.

Also provided are methods of treating or inhibiting neuronal damage in a subject. In some embodiments, the method includes administering to the subject a therapeutically effective amount of an isolated or recombinant neuroprotective peptide, fusion protein, composition, isolated nucleic acid molecule, or vector disclosed herein, thereby treating or inhibiting neuronal damage in the subject. In some examples, the subject is suffering from or has suffered from cerebral ischemia, stroke, traumatic brain injury or a neurodegenerative disease. In some examples, the subject is administered a neuroprotective peptide or fusion protein intravenously or by intraperitoneal injection. In some examples, the method includes administering one or more additional therapies or therapeutic agents to the subject. In one example, the additional therapeutic agent is nerinetide, a TAT-linked peptide (Hill et al., *Lancet* 395(10227): 878-887, 2020). In another example, the additional therapy is mechanical thrombectomy (Munich et al., *Neurosurgery* 85(1):S60-S67, 2019).

Further provided is a method of treating ischemic stroke in a subject. In some embodiments, the method includes administering to the subject a therapeutically effective amount of an isolated or recombinant neuroprotective peptide, fusion protein, composition, isolated nucleic acid molecule, or vector disclosed herein, thereby treating ischemic stroke in the subject. In some examples, the subject is administered a neuroprotective peptide or fusion protein intravenously or by intraperitoneal injection. In some examples, the method further includes administering on or more additional therapies or therapeutic agents to the subject, such as thrombolytic therapy, nerinetide or mechanical thrombectomy.

V. Kv2.2 Protein and Peptide Sequences

The neuroprotective peptides disclosed herein are derived from a seven amino acid fragment of the C-terminal region of the Kv2.2 protein. In particular, the neuroprotective peptides include the sequence SIDSFTS (SEQ ID NO: 1; corresponding to residues 602-608 of human Kv2.2 of SEQ ID NO: 42), or a modified version thereof. In some examples, the Kv2.2 derived neuroprotective peptide includes at least one phosphorylated residue, such as a phosphorylated serine residue. In other examples, the neuroprotective peptide includes at least one pseudophosphorylated residue, such as a substitution of a serine residue with an aspartic acid or glutamic acid residue. Provided in the table below are exemplary neuroprotective peptides.

| SEQ ID NO: | Sequence | Description |
|---|---|---|
| 1 | SIDSFTS | DP-2 |
| 2 | DIDSFTS | Ser to Asp mutant of DP-2 |
| 3 | SIDDFTS | Ser to Asp mutant of DP-2 |
| 4 | SIDSFTD | Ser to Asp mutant of DP-2 |
| 5 | DIDDFTS | Ser to Asp mutant of DP-2 |
| 6 | SIDDFTD | Ser to Asp mutant of DP-2 |
| 7 | DIDSFTD | Ser to Asp mutant of DP-2 |
| 8 | DIDDFTD | Ser to Asp mutant of DP-2 |
| 9 | EIDSFTS | Ser to Glu mutant of DP-2 |
| 10 | SIDEFTS | Ser to Glu mutant of DP-2 |
| 11 | SIDSFTE | Ser to Glu mutant of DP-2 |
| 12 | EIDEFTS | Ser to Glu mutant of DP-2 |
| 13 | SIDEFTE | Ser to Glu mutant of DP-2 |
| 14 | EIDSFTE | Ser to Glu mutant of DP-2 |
| 15 | EIDEFTE | Ser to Glu mutant of DP-2 |
| 16 | pSIDSFTS | Ser phosphorylation mutant |
| 17 | SIDpSFTS | Ser phosphorylation mutant |
| 18 | SIDSFTpS | Ser phosphorylation mutant |

-continued

| SEQ ID NO: | Sequence | Description |
|---|---|---|
| 19 | pSIDpSFTS | Ser phosphorylation mutant |
| 20 | SIDpSFTpS | Ser phosphorylation mutant |
| 21 | pSIDSFTpS | Ser phosphorylation mutant |
| 22 | pSIDpSFTpS | Ser phosphorylation mutant | pS = phosphorylated serine

In some embodiments, the neuroprotective peptide is 7 amino acids in length and has an amino acid sequence consisting of the sequence of an exemplary peptide set forth as any one of SEQ ID NOs: 1-22. In other embodiments, the peptide is up to 20 amino acids in length and includes the sequence of any one of the exemplary peptides. In some examples, when the peptide is longer than 7 amino acids in length, the remaining sequence corresponds to adjacent residues of the Kv2.2 protein, such as the human, mouse or rat Kv2.2 protein. In specific examples, the peptide, over its complete length, is at least 85%, at least 90%, at least 95%, at least 96%, at least 97%, at least 98%, at least 99% or 100% identical to human Kv2.2 of SEQ ID NO: 42, mouse Kv2.2 of SEQ ID NO: 41, or rat Kv2.2 of SEQ ID NO: 43, which are shown below. The 7-amino acid DP-2 peptide is underlined in each sequence.

Human Kv2.2
(Uniprot Q92953 - SEQ ID NO: 42)
MAEKAPPGLNRKTSRSTLSLPPEPVDIIRSKTCSRRVKINVGGLNHEVLW
RTLDRLPRTRLGKLRDCNTHESLLEVCDDYNLNENEYFFDRHPGAFTSIL
NFYRTGKLHMMEEMCALSFGQELDYWGIDEIYLESCCQARYHQKKEQMNE
ELRREAETMREREGEEFDNTCCPDKRKKLWDLLEKPNSSVAAKILAIVSI
LFIVLSTIALSLNTLPELQETDEFGQLNDNRQLAHVEAVCIAWFTMEYLL
RFLSSPNKWKFFKGPLNVIDLLAILPYYVTIFLTESNKSVLQFQNVRRVV
QIFRIMRILRILKLARHSTGLQSLGFTLRRSYNELGLLILFLAMGIMIFS
SLVFFAEKDEDATKFTSIPASFWWATITMTTVGYGDIYPKTLLGKIVGGL
CCIAGVLVIALPIPIIVNNFSEFYKEQKRQEKAIKRREALERAKRNGSIV
SMNLKDAFARSMELIDVAVEKAGESANTKDSADDNHLSPSRWKWARKALS
ETSSNKSFENKYQEVSQKDSHEQLNNTSSSPQHLSAQKLEMLYNEITKT
QPHSHPNPDCQEKPERPSAYEEEIEMEEVVCPQEQLAVAQTEVIVDMKST
SSIDSFTSCATDFTETERSPLPPPSASHLQMKFPTDLPGTEEHQRARGPP
FLTLSREKGPAARDGTLEYAPVDITVNLDASGSQCGLHSPLQSDNATDSP
KSSLKGSNPLKSRSLKVNFKENRGSAPQTPPSTARPLPVTTADFSLTTPQ
HISTILLEETPSQGDRPLLGTEVSAPCQGPSKGLSPRFPKQKLFPFSSRE
RRSFTEIDTGDDEDFLELPGAREEKQVDSSPNCFADKPSDGRDPLREEGS
VGSSSPQDTGHNCRQDIYHAVSEVKKDSSQEGCKMENHLFAPEIHSNPGD
TGYCPTRETSM Mouse Kv2.2
(Uniprot A6H8H5 - SEQ ID NO: 40)
MAEKAPPGLNRKTSRSTLSLPPEPVDIIRSKTCSRRVKINVGGLNHEVLW
RTLDRLPRTRLGKLRDCNTHESLLEVCDDYNLNENEYFFDRHPGAFTSIL
NFYRTGKLHMMEEMCALSFGQELDYWGIDEIYLESCCQARYHQKKEQMNE
ELRREAETMREREGEEFDNTCCPEKRKKLWDLLEKPNSSVAAKILAIVSI
LFIVLSTIALSLNTLPELQENDEFGQPSDNRKLAHVEAVCIAWFTMEYLL
RFLSSPNKWKFFKGPLNVIDLLAILPYYVTIFLTESNKSVLQFQNVRRVV
QIFRIMRILRILKLARHSTGLQSLGFTLRRSYNELGLLILFLAMGIMIFS
SLVFFAEKDEDATKFTSIPASFWWATITMTTVGYGDIYPKTLLGKIVGGL
CCIAGVLVIALPIPIIVNNFSEFYKEQKRQEKAIKRREALERAKRNGSIV
SMNLKDAFARSMELIDVAVEKAGESANTKDSVDDNHLSPSRWKWARKALS
ETSSNKSYENKYQEVSQNDSHEHLNNTSSSSPQHLSAQKLEMLYNEITKT
QPHSHPNPDCQEQPERPCVYEEEIEMEEVICPQEQLAVAQTEVIVDMKST
SSIDSFTSCATDFTETERSPLPPPSASHLQMKFPTDLPGTDEHQRARAPP
FLTLSRDKGPAAREAAVDYAPIDITVNLDAGASHGPLQPDSASDSPKSSL
KGSNPLKSRSLKVNFQENRASAPQTPPSTARPLPVTTADFPLTTPQHMST
ILLEEALPQGQPPLLEADDSAHCQGPSKGFSPRFPKQKLFPFSSRERRSF
TEIDTGEDEDFLDLQRSRPDKQADPSPNCLADKPGDARDSLREEGCVGSS
SPQNTDHNCRQDIYQAVGEVKKDSSQEGYKMENHLFAPEIHSNPGDTGHC
PTRETSM Rat Kv2.2
(Uniprot Q63099 - SEQ ID NO: 43)
MAEKAPPGLNRKTSRSTLSLPPEPVDIIRSKTCSRRVKINVGGLNHEVLW
RTLDRLPRTRLGKLRDCNTHESLLEVCDDYNLNENEYFFDRHPGAFTSIL
NFYRTGKLHMMEEMCALSFGQELDYWGIDEIYLESCCQARYHQKKEQMNE
ELRREAETMRDGEGEEFDNTCCPEKRKKLWDLLEKPNSSVAAKILAIVSI
LFIVLSTIALSLNTLPELQENDEFGQPSDNRKLAHVEAVCIAWFTMEYLL
RFLSSPNKWKFFKGPLNVIDLLAILPYYVTIFLTESNKSVLQFQNVRRVV
QIFRIMRILRILKLARHSTGLQSLGFTLRRSYNELGLLILFLAMGIMIFS
SLVFFAEKDEDATKFTSIPASFWWATITMTTVGYGDIYPKTLLGKIVGGL
CCIAGVLVIALPIPIIVNNFSEFYKEQKRQEKAIKRREALERAKRNGSIV
SMNLKDAFARSMELIDVAVEKAGESANIKDSVDDNHLSPSRWKWARKALS
ETSSNKSYENKYQEVSQKDSHEQLNNTSSSPQHLSAQKLEMLYNEITKT
QTHSHPNPDCQEQPERPSAYEEEIEMEEVVCPQEQLAVAQTEVIVDMKST
SSIDSFTSCATDFTETERSPLPPPSASHLQMKFPTDLPGMDEHQRVRAPP
FLTLSRDKGPAAREAALDYAPIDITVNLDAGASHGPLQPDSASDSPKSSL
KGSNPLKSRSLKVNFQENRGSAPQTPPSTARPLPVTTADFPLTTPQHMST
ILLEESPPPGTETLPGADVSAHCQGPSKGLSPRVPKQKLFPFSSRERRSF
TEIDTGEDEDFLDLQRPRPDKQADPSPNCLADKPGEARDPLREEGCVGSS
SPQNTDHNCRQDIYQAVGEVKKDSSQEGYKMENHLFAPEIHSNPGDTGYC
PTRETSM In one example, the peptide is 12 amino acids in length and has the amino acid sequence MKSTSSIDSFTS (SEQ ID NO: 27).

In other embodiments, neuroprotective peptides are up to 20 amino acids in length and comprise no more than 5, no more than 4, no more than 3, no more than 2 or no more than 1 conservative amino acid substitution(s) relative to human, mouse or rat Kv2.2.

V. Administration of Neuroprotective Peptides

Methods of administering therapeutic proteins and peptides are known. In some embodiments of the disclosed methods, Kv2.2-derived neuroprotective peptides or fusion proteins, nucleic acids or vectors (or compositions thereof) are administered to a subject for the treatment of cerebral ischemia, stroke (such as ischemic stroke or hemorrhagic stroke), CNS trauma/injury, traumatic brain injury, a neurodegenerative disease, or any other condition associated with neuronal damage and/or neuronal cell death. When administering the neuroprotective peptides (or fusion proteins thereof), one must consider the appropriate target site based on the disease to be treated. If the site of action is the central nervous system, the protein must be able to cross the blood-brain barrier (BBB) or be delivered directly to the target site in the brain.

Methods of administering neurotrophic factors for the treatment of a variety of neurodegenerative diseases have been previously described (see, for example, Levy et al., *Biodrugs* 19(2):97-127, 2005; Gill et al., *Nat Med* 9:589-595, 2003; Nutt et al., *Neurology* 60:69-73, 2003; Olson et al., *J Neural Transm Park Dis Dement Sect* 4:79-95, 1992; Eriksdotter et al., *Dement Geriatr Cogn Disord* 9:246-257, 1998; Bradley, *Ann Neurol* 38:971, 1995; The BDNF Study Group Phase III, *Neurology* 52:1427-1433, 1999; Ochs et al., *Amyotroph Lateral Scler Other Motor Neuron Disord* 1:201-206, 2000; ALS CNTF Treatment Study Group, *Neurology* 46(5):1244-1249, 1996; Miller et al., *Neurology* 47:1329-1331, 1996; Miller et al., *Ann Neurol* 39:256-260, 1996; Lai et al., *Neurology* 49:1621-1630, 1997; Borasio et al., *Neurology* 51:583-586, 1998). Such methods can be utilized for administration of the neuroprotective peptides or fusion proteins described herein.

In some embodiments, the neuroprotective peptide, fusion protein, nucleic acid, or vector is administered intravenously. In other embodiments, the neuroprotective peptide, fusion protein, nucleic acid, or vector is administered by intraperitoneal injection.

In some embodiments, the neuroprotective peptide, fusion protein, nucleic acid or vector is administered by direct infusion into the brain, such as by intracerebroventricular (ICV) injection/infusion, intrastriatal injection, intranigral injection, intracerebral injection, infusion into the putamen, intrathecal infusion (such as by using an implanted pump) or by subcutaneous injection. Intranasal administration also leads to delivery to the CNS. Thus, in some examples, the neuroprotective peptide, fusion protein, nucleic acid or vector is administered intranasally.

In some embodiments, the neuroprotective peptide, fusion protein, nucleic acid or vector is administered about 120 minutes, about 90 minutes, about 60 minutes, about 30 minutes or about 15 minutes prior to reperfusion (such as thrombectomy). In some embodiments, the neuroprotective peptide, fusion protein, nucleic acid or vector is administered prior to reperfusion, during reperfusion and/or following reperfusion. In some examples, the subject is administered the neuroprotective peptide, fusion protein, nucleic acid or vector in multiple doses, such as 2, 3, 4 or 5 or more doses.

In some embodiments, neuroprotective peptides, fusion proteins, nucleic acids or vectors are administered using biodegradable microparticles (~1-100 μm) or nanoparticles (~50-1000 nm). Nanoparticles and microparticles (also known as nanospheres or microspheres) are drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nano/microparticles using processes well known in the art.

The nano/microparticles for use with the methods described herein can be any type of biocompatible particle, such as biodegradable particles, such as polymeric particles, including, but not limited to polyamide, polycarbonate, polyalkene, polyvinyl ethers, and cellulose ether nano/microparticles. In some embodiments, the particles are made of biocompatible and biodegradable materials. In some embodiments, the particles include, but are not limited to particles comprising poly(lactic acid) or poly(glycolic acid), or both poly(lactic acid) and poly(glycolic acid). In particular embodiments, the particles are poly(D,L-lactic-co-glycolic acid) (PLGA) particles.

Other biodegradable polymeric materials are contemplated for use with the methods described herein, such as poly(lactic acid) (PLA) and polyglycolide (PGA). Additional useful nano/microparticles include biodegradable poly(alkylcyanoacrylate) particles (Vauthier et al., *Adv. Drug Del. Rev.* 55: 519-48, 2003).

Various types of biodegradable and biocompatible nano/microparticles, methods of making such particles, including PLGA particles, and methods of encapsulating a variety of synthetic compounds, proteins and nucleic acids, have been described (see, for example, U.S. Publication No. 2007/0148074; U.S. Publication No. 20070092575; U.S. Patent Publication No. 2006/0246139; U.S. Pat. Nos. 5,753,234; 7,081,489; and PCT Publication No. WO/2006/052285, which are herein incorporated by reference). In addition, microsphere-mediated delivery of proteins to the central and peripheral nervous system has been described in, for example, US Patent Application Publication No. 2011/0217264, which is herein incorporated by reference.

The following examples are provided to illustrate certain particular features and/or embodiments. These examples should not be construed to limit the disclosure to the particular features or embodiments described.

EXAMPLES

Example 1

Materials and Methods

This example describes the materials and experimental procedures for the studies described in Example 2.

Study Design

The objective of the study was to define the critical region within the Kv2.2 CT that is responsible for Kv2.1 declustering and to develop a neuroprotective declustering therapeutic based on this sequence. For in vitro experiments utilizing neuronal cell culture for confocal imaging or toxicity studies, experiments were reproduced at least three times on three separate culture dates. For in vivo middle cerebral artery occlusion (MCAo) experiments, results of a small pilot study were utilized to power sample sizes.

Neuronal Cell Culture

In vitro experiments utilized primary cortical neuronal cultures prepared from embryonic day 16-17 Sprague-Dawley rats of either sex in a protocol described previously (McCord et al., *J Physiol* (*Lond*). 592: 3511-3521, 2014). Timed-pregnant rats (Charles River Laboratories, Wilmington, Mass.) were sacrificed by $CO_2$ inhalation. Embryonic cortices were dissociated with trypsin (0.6 mg/mL) and cells plated in sterile 6-well plates on poly-L-ornithine-coated glass coverslips at a density of 670,000 cells per well. Cytosine arabinoside (1-2 µM) was utilized to inhibit non-neuronal proliferation on day 14 in vitro (DIV); cultures were utilized at 21-25 DIV.

TAT-Linked Peptides

UniProt Consortium protein sequence database was used to align protein sequences. TAT (YGRKKRRQRRR; SEQ ID NO: 31)-linked peptides with 95.1%-99.8% purity analyzed by high performance liquid chromatography were generated by GenScript (Piscataway, N.J.) (Table 1). Clustering residues within the PRC domain of Kv2.1 (S587, S590, F591, and S593; rat sequence, Uniprot P15387; SEQ ID NO: 32), correspond to S583, S586, F587, and S589 in Lim, et al. (*Neuron*. 25: 385-397, 2000).

TABLE 1

TAT-linked peptides

| Peptide | AA Sequence | SEQ ID NO: | Relevant FIGS. |
|---|---|---|---|
| TAT-DP-2 | YGRKKRRQRRRSIDSFTS | 23 | FIGS. 2-6 |
| TAT-Sc-2 | YGRKKRRQRRRDFSSIST | 24 | FIGS. 2-6 |
| TAT-DP-2A | YGRKKRRQRRRAIDAFTA | 25 | FIG. 12 |
| TAT-DP-2D | YGRKKRRQRRRDIDDFTD | 26 | FIG. 12 |

Plasmid Constructs pCMV-DP-1 and pCMV-Sc-1 plasmids were generated by standard cloning into the multiple cloning sites of pCMV-IRES2-GFP (Clontech, Cat. #6029-1). The IRES2-GFP region of the parent plasmid was subsequently removed. Successful cloning was confirmed by sequencing. Table 2 lists all plasmids utilized in this study.

TABLE 2

Plasmid constructs

| Plasmid | Expressed Active Protein | Experimental Use | Relevant FIGS. |
|---|---|---|---|
| pcDNA3 vector | Empty vector | Experimental controls | FIGS. 1 and 2; FIGS. 8, 9, 11, and 12 |
| pCMV-DP-1 | DP-1 peptide | DP-1 expression in vitro | FIG. 1 |
| pCMV-Sc-1 | Sc-1 peptide | Sc-1 expression in vitro | FIG. 1 |
| pCMV-Kv2.2CT | Kv2.2 channel C-terminal peptide | Kv2.2 CT expression in vitro | FIG. 1 |
| pCMV-dTomato | dTomato red fluorescent protein | Visualization of neuronal cell bodies; experimental blinding | FIGS. 1 and 2; FIGS. 8, 9, 11, and 12 |
| pCMV-Kv2.1-GFP | GFP-tagged Kv2.1 channel | Visualization of Kv2.1 surface distribution | FIGS. 1 and 2; FIGS. 8, 9, 11, and 12 |

Transfection

Transfections were performed with Lipofectamine 2000 (L2K; Invitrogen, Carlsbad, Calif.). Cortical neuronal cultures on glass coverslips were placed into wells containing 500 µL of Dulbecco's minimum essential medium with 2% HyClone bovine serum (D2C; Thermo Fisher Scientific, Waltham, Mass.). A mixture of 1.5 µg of total cDNA and 2 µL of L2K was prepared in 100 µL of Opti-MEM I (Life Technologies Corp., Grand Island, N.Y.) for each well and added. Cultures were utilized 18-24 hours following transfection. cDNA amounts for each transfection experiment are described below for each figure. FIG. 1: 0.375 µg/well Kv2.1-GFP plasmid, 0.495 µg/well pcDNA3 vector plasmid, and 0.63 µg/well of either DP-1 or Sc-1, or Kv2.2 CT-expressing plasmid. FIGS. 2, 8, 9, 10, 12: 0.375 µg/well Kv2.1-GFP plasmid, 0.15 µg/well tdTomato plasmid (from Gerhart Ryffel; Addgene plasmid #30530), and 0.975 µg/well pcDNA3 vector plasmid.

Immunohistochemistry

Eight-week-old C57BL/6J male mice (28-30 g; Jackson, Bar Harbor, Me.) were administered IP injections of 6 nmol/g TAT-DP-2 (n=3) or TAT-Sc-2 peptide (n=3). Two hours post-injection, mice were anesthetized with 3% isoflurane (Henry Schein Animal Health, Dublin, Ohio) in a 3:1 $NO/O_2$ gas mixture. Fifty mL of ice-cold 1× sterile PBS was transcardially perfused (5-10 mL/min), immediately followed by 50 mL of 4% sterile paraformaldehyde (PFA; 5-10 mL/min). Brains were removed and placed in 4% PFA at 4° C. for 24 hours, then transferred to 30% sucrose in 1× PBS at 4° C. for 48-72 hours. Brains were embedded with TissueTek O.C.T. Compound (Sakura Finetek USA Inc., Torrence, Calif.) onto an SM 2010R Cyrosectioner (Leica Biosystems, Wetzlar, Germany), sectioned (30 µm) and stored.

Brain sections were rinsed in sterile 24-well plates in Tris-buffered saline (TBS) solution. Sections were then transferred to new wells containing 0.5% Triton X-100 and 10% normal goat serum (NGS) in TBS for 30 minutes at room temperature. Next, sections were again transferred to wells containing primary anti-Kv2.1 antibody (mouse monoclonal IgG; RRID AB_192761; UC Davis/NeuroMab Facility), diluted 1:200 in 0.3% Triton X-100 and 3% NGS in TBS for 24 hours at 4° C. Sections were washed in TBS and incubated with secondary anti-mouse IgG fluorescein isothiocyanate (FITC)-tagged antibody (goat monoclonal IgG; Cat. F0257; Sigma Aldrich; St. Louis, Mo.), diluted 1:500 in 0.3% Triton X-100 and 3% NGS in TBS for 1 hour at room temperature and then mounted.

Immunocytochemistry

The in vitro Kv2.1 immunofluorescence experiment (FIG. 10) was carried out in DIV 21-26 primary rat neuronal cultures, as described above. Each coverslip was treated with either TAT-DP-2 or TAT-Sc-2 in its individual well to reach a final concentration of 10 After 3 hours, coverslips were transferred to PBS and immediately fixed with 4% paraformaldehyde/4% sucrose for 15 minutes. Coverslips were rinsed with PBS 3 times and then permeabilized with 0.25% triton-X-100 for 15 minutes. Cells were rinsed with PBS 3 times and then blocked with 2% BSA/10% normal goat serum for 1 hour at room temperature. Neurons were stained with mouse anti-Kv2.1 antibody (1:250, clone K89/34, Abcam, RRID: AB_2750677) using the microdrop method at 4° C. overnight. Cells were rinsed in PBS 3 times and then stained with Alexa Fluor® 568 goat anti-mouse secondary antibody (1:500, Thermo Fisher Scientific, RRID: AB_2534072) for 1 hour at room temperature. Finally, cells were rinsed in PBS 3 times before mounting. Confocal Z-projections of well-isolated neurons were obtained for evaluation of Kv2.1 cluster density (described below). The experimenter was blinded to the treatment groups during image analysis.

Confocal Imaging and Kv2.1 Cluster Analysis

Figure 10A:
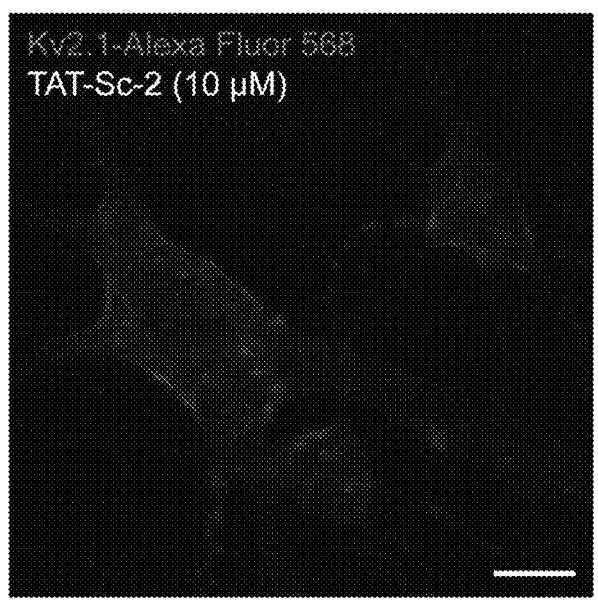
FIGS. 10A-10B: TAT-DP-2 induces dispersal of endogenous Kv2.1 channels in vitro.
Figure 10B:
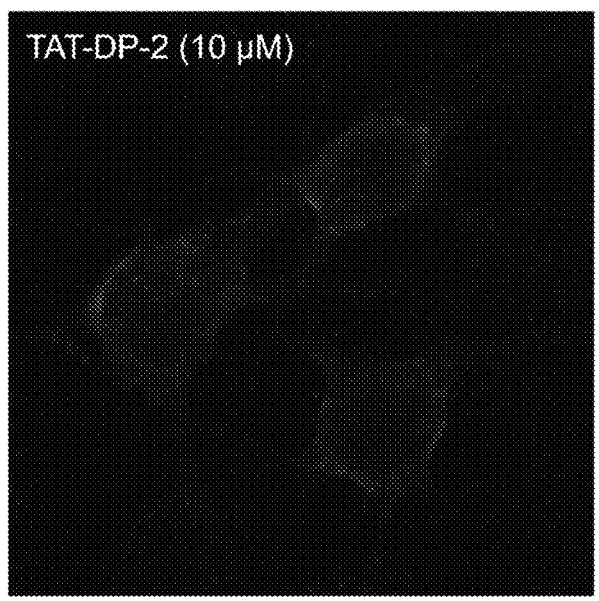
Figure 10B:
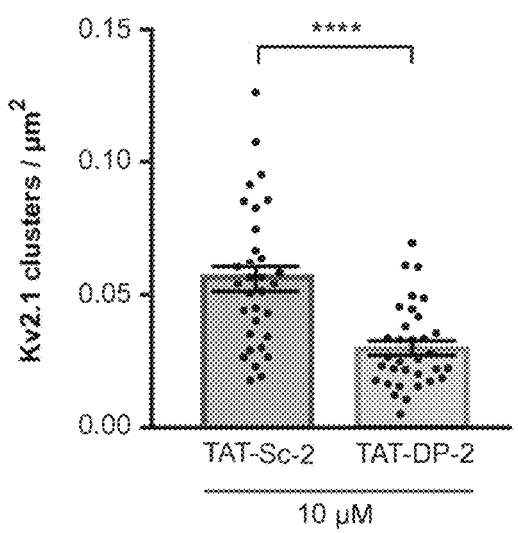

To analyze Kv2.1 distribution in live primary cortical neurons, cells were transfected with both a tdTomato construct and a GFP-tagged Kv2.1 construct (O'Connell, et al., *J Neurosci.* 26: 9609-9618, 2006) and imaged on a Nikon A1+ confocal microscope (Nikon, Tokyo, Japan). Cells were chosen at random by looking only at the tdTomato signal (561 nm), in order to avoid bias. At least three separate culture dates were used per experiment and three coverslips were transfected per condition each time. For these experiments, "n" refers to the total number of cells imaged. Five to 15 optical sections (0.5 μm) capturing the cell surface were obtained of single cells at 60× magnification (Schulien et al., *J Physiol (Lond)*. 594: 2647-2659, 2016), creating a maximum-intensity projection (MAX-IP) of Kv2.1-GFP distribution. To analyze Kv2.1 distribution in the cerebral cortex of fixed brain slices, 51-54 image fields were obtained at 60× magnification across 18 sections from three fixed mouse brains per treatment (total of 6 animals). Image fields were captured by first focusing on an area of superficial cortex closest to the cover glass. Next, 24 optical sections (0.5 μm) were obtained moving deeper into the tissue in order to produce a 12 μm maximum-intensity projection for analysis of Kv2.1 distribution. Laser power, HV (gain), offset, pinhole size, and all camera parameters were kept identical between all samples in a given experiment. Nikon Instruments Software Advanced Research (NIS-Elements AR) was utilized to analyze GFP-tagged Kv2.1 channel cluster distribution. For live images of transfected neurons, object count parameters were customized to define a Kv2.1 cluster as an area of high intensity GFP fluorescence (compared to background), measuring 0.05 μm$^2$ or larger (Schulien et al., *J Physiol (Lond)*. 594: 2647-2659, 2016). Kv2.1 cluster density was calculated by normalizing the number of Kv2.1 clusters counted to the somatic area of each neuron (#Kv2.1 clusters/μm$^2$). Due to high variability in GFP-Kv2.1 expression between individual neurons, intensity thresholding required cell-specific local-background subtraction. In each neuron analyzed, two populations of Kv2.1-GFP expression were first noted—(a) highly localized signals of clustered Kv2.1 channels, and (b) diffuse background staining that represents freely-dispersed, conducting Kv2.1 channels on the plasma membrane. A small region of interest (ROI) within region (b) was set as the background subtraction standard of the image, creating an optimal signal-to-noise ratio for clustered Kv2.1 channels. Finally, automated intensity-thresholding was set to identify Kv2.1 clusters as well-defined regions with a significantly higher Kv2.1-GFP signal than local background. This protocol was also adapted for analysis of cortical neurons immunostained with an anti-Kv2.1 antibody to visualize endogenous Kv2.1 distribution, except that Alexa Fluor® 568 fluorescence was correlated with Kv2.1 cluster localization (FIG. 10). For analysis of Kv2.1 channel cluster distribution in whole-field images of fixed cortical tissue, NIS-Elements AR object count parameters were applied to the entire image field, each of which contained approximately 60-80 cell bodies. Kv2.1 channel clusters were designated as areas of fluorescence with pixel intensity (AFU) between 2200-4095, that measured within three standard deviations previous empiric measurements of average Kv2.1 cluster area (0.41 μm$^2$-1.37 μm$^2$), as reported earlier (O'Connell, et al., *J Neurosci.* 26: 9609-9618, 2006).

Proximity Ligation Assay

Duolink proximity ligation assay (PLA) technology (Sigma-Aldrich, St. Louis, Mo.) was utilized to assess in situ protein-protein interaction between Kv2.1 and vesicle-associated molecular protein (VAMP)-associated protein A (VAPA). Primary cortical neurons on glass coverslips were treated in 24-well plates with vehicle (dH$_2$O), TAT-Sc-2 (10 μM), or TAT-DP-2 (10 μM) for 2 hours at 37° C./5% CO$_2$. Neurons were then rinsed with 2 mL ice-cold sterile PBS and then transferred to 1 mL 4% paraformaldehyde (PFA) in PBS for 20 minutes to fix. Coverslips were transferred to 1 mL 0.1 M glycine (in PBS) to quench fixation and rinsed three times in 1 mL PBS. Membrane permeabilization was accomplished with 1 mL 0.25% Triton X-100 (Sigma-Aldrich, St. Louis, Mo.) and non-specific binding was blocked with 10% bovine serum albumin (in PBS) for 30 minutes. Primary immunolabeling was accomplished by 18-24 hour exposure to rabbit anti-Kv2.1 polyclonal antibody (1:500 in 3% BSA; RRID AB_2040162; Alomone Labs, Jerusalem, Israel), mouse anti-VAPA monoclonal antibody (1:500 in 3% BSA; RRID AB_2722702; UC Davis/ NeuroMab Facility), and chicken anti-MAP2 polyclonal antibody (1:1000 in 3% BSA; RRID AB_5392; Abcam, Cambridge, Mass.) in 3% BSA (in PBS) at 4° C. under gentle agitation. Secondary immunolabeling of MAP2 staining was accomplished by incubation with a Cy5-tagged donkey anti-chicken antibody (1:500 in 3% BSA) for one hour. Coverslips were then rinsed four times for 5 minutes in PBS before beginning the PLA. Duo-link protocol was followed according to factory instruction with adaptation from (Söderberg et al., *Methods.* 45: 227-232, 2008). Briefly, fixed and immunocytochemically labeled neurons were first incubated with oligonucleotide-conjugated anti-mouse minus (1:5 in 3% BSA) and anti-rabbit plus (1:5 in 3% BSA) probes for 1 hour at 37° C., in order to probe for anti-VAPA and anti-Kv2.1 primary antibodies, respectively. Coverslips were then rinsed in Duolink PLA Wash Buffer A (WBA) two times for 5 minutes. Oligonucleotide ligation of plus and minus probes was accomplished by incubation with ligase (1:40) in Duolink PLA ligation solution (1:5 in dH$_2$O) for 45 minutes at 37° C., before coverslips were again rinsed in WBA two times for 2 minutes. Rolling-circle amplification (RCA) reaction and subsequence fluorescently-labeled oligonucleotide hybridization with this concatemeric product was accomplished by incubating coverslips with Duolink amplification orange (1:5 in dH$_2$O) and polymerase enzyme (1:40) for 100 minutes at 37° C. Finally, coverslips were washed in Duolink Wash Buffer B two times for 10 minutes, followed by a final wash in 0.01× WBB for 1 minute. Coverslips were then mounted onto glass slides with Duolink DAPI mounting media for confocal imaging.

PLA puncta were imaged on a Nikon A1+ confocal microscope (Nikon, Tokyo, Japan) with a 60× objective. Random neuronal somas were identified on each coverslip utilizing the Cy5 filter to visualize MAP2 staining. PLA puncta signals were then obtained by capturing 25 optical sections (0.5 μm) that constrained the entire Z-width of PLA-TRITC fluorescence as MAX-IP files. Laser power, HV (gain), offset, pinhole size, and all camera parameters were kept identical between all samples in four separate experiments. NIS-Elements AR object count feature was then utilized to analyze the quantity of PLA puncta per cell. To do this, cell somas and proximal dendrites were first selected as ROIs, using MAP2-positive staining to confirm analysis of neurons. As distinct local PLA puncta-TRITC auto-fluorescence (markedly different in appearance from PLA puncta) was noted, local background subtraction using a small ROI within this region was performed in a protocol similar to that described earlier (Glynn, et al., *Nat Protoc*. 1: 1287-1296, 2006). Next, PLA puncta were counted and measured by a semi-automated object count feature within NIS-Elements AR analysis program. Thresholding was set for each image by choosing well-defined, highly fluorescent PLA puncta compared to background fluorescence and setting inclusion thresholds based on these puncta. Object counts were verified by manual counting.

Electrophysiology

Whole-cell voltage-clamp currents from rat cortical neurons were obtained with Axopatch 200B amplifier using pClamp software (Molecular Devices, Sunnyvale, Calif.) using 3-5 MΩ electrodes. The extracellular solution contained (in mM): 2.0 $MgCl_2$, 2.5 KCl, 115 NaCl, 10 HEPES, 10 D-glucose, 1.0 $CaCl_2$, and 0.25 µM tetrodotoxin at pH 7.2. The electrode solution contained (in mM): 100 potassium gluconate, 1 MgCl, 10 KCl, 1 $CaCl_2$, 2 $MgCl_2$-ATP, 0.33 GTP, 11 EGTA, and 10 HEPES at pH 7.2. Series resistance was compensated (80%) and currents were digitized at 10 kHz and filtered at 2 kHz. Potassium currents were evoked with a series of 200 ms voltage steps from a holding potential of −80 to 80 mV in 10 mV increments. A 30 ms pre-pulse to +10 mV was used to inactivate A-type potassium currents. Delayed-rectifier currents were measured relative to baseline at 180 ms after the initiation of each voltage step. Currents were normalized to cell capacitance. Current density analyses were limited to the +30 mV voltage step to minimize voltage errors due to large whole-cell current amplitudes at higher holding potentials, which can be significant even after compensation for series resistance.

Cell Toxicity Assay

Cortical neurons were pre-treated with vehicle, TAT-DP-2 (3 µM), or TAT-Sc-2 (3 µM) for 2 hours in HEPES-buffered minimal essential media with 0.01% bovine serum albumin (MHB). Next, cells with the same peptide concentrations along with either vehicle or 60 µM DL-threo-β-benzyloxyaspartic acid (TBOA) for 6 hours. Each well was washed two times with either 0.5 mL of vehicle or 60 µM TBOA and neurons were incubated overnight. Twenty-four hours following initial TBOA treatment, media was collected for lactate dehydrogenase assays (Sigma Aldrich, St. Louis, Mo.). Relative toxicity was quantified by calculating the ratio of LDH concentration in TBOA-treated over non-TBOA-treated wells. In cell culture, LDH release measures neuronal cell death and is not specific to any one mechanism of cell demise.

Middle Cerebral Artery Occlusion (MCAo) Microsurgery

Mice were anesthetized with isoflurane and the common carotid artery was exposed. A single-use silicon-coated suture (MCAo suture #602256PK10; Doccol Corporation, Sharron, Mass.) was advanced 8-9 mm into the internal carotid artery, occluding the MCA. The suture was secured with 6-0 silk ligatures for 50 minutes, then removed. Twenty-four hours following cerebral reperfusion, mice were sacrificed and four 2-mm coronal brain sections were obtained from each animal. Sections were stained with 0.05% 2,3,5-triphenyltetrazolium chloride (TTC) in PBS for 30 minutes at room temperature. Brain sections were digitally scanned following staining and a blinded experimenter measured infarct ratios (infarct area/total section area) using NIH ImageJ software. Visual representation of this protocol is in FIG. 6B.

To analyze neurological deficits following MCA stroke, testing was performed by a blinded experimenter on additional cohorts, both at baseline (all initial scores were 0) and on post-stroke days 1, 2, 3, 5, 7, 10, 14, 21, 28, 35, and 42. An objective murine neurological score (Table 3) was assigned on each date, ranging from 0 (no neurological deficit) to 8 (stroke-related death) (Yeh et al., *J Neurosci*. 37: 5648-5658, 2017).

TABLE 3

Murine Neurological Score (MNS) criteria

| MNS | Objective Criterion |
|---|---|
| 0 | Mouse exhibits no neurologic deficit |
| 1 | Mouse exhibits right forelimb flexion when suspended by the tail; Failure to extend left forepaw fully when suspended by the tail |
| 2 | Mouse exhibits right shoulder adduction when suspended by the tail |
| 3 | Mouse exhibits reduced resistance to lateral push toward the right |
| 4 | Mouse exhibits spontaneous movement in all directions with circling to the right only if pulled by tail |
| 5 | Mouse circles or walks spontaneously to the right only |
| 6 | Mouse walks only when stimulated |
| 7 | Mouse exhibits no response to stimulation |
| 8 | Stroke-related death |

Peptide-Blot Array

Standard 9-fluorenylmethoxy carbonyl chemistry was used to synthesize peptides and spot them onto Celluspots nitrocellulose disks prederivatized with a polyethylene glycerol spacer (Intavis), using the Respep peptide synthesizer. The peptides were spotted on 20 membranes fitted on microscope glass slides (Intavis) using an Intavis MultiPep robot. For hybridization and immunoblotting of arrays, Celluspots slides were washed in TBST (50 mM Tris-HCl, pH 7.4, 150 mM NaCl, 0.1% Tween 20) for 10 minutes, 5% non-fat dry milk and then blocked for 1 hour at room temperature (RT) with gentle shaking in TBST containing 5% nonfat dry milk. Lysates from HEK293 cells transfected as before (Yeh et al., *J Neurosci*. 37: 5648-5658, 2017; Yeh et al., *Proc Natl Acad Sci USA*. 116: 15696-15607, 2019; Dustrude et al., *Proc Natl Acad Sci USA*. 113: E8443-E8452, 2016) with pEGFP-N1-VAPA; 1-242 (Addgene #18874) were made in 20 mM Tris, 50 mM NaCl, 2 mM $MgCl_2$, 1% Tergitol, 0.5% sodium deoxycholate, 0.1% sodium dodecyl sulfate with protease (Cat #B14002, Bimake), phosphatase (Cat #B15002, Bimake) inhibitor cocktails and 5 U/ml of universal nuclease (Cat #88702, Thermofisher) added extemporaneously. The concentration of lysates was measured by BCA (Cat #23227, Thermofisher) and peptide arrays were incubated with 1 mg/ml of total protein overnight at 4° C. (Yeh et al., *J Neurosci*. 37: 5648-5658, 2017; Yeh et al., *Proc Natl Acad Sci USA*. 116: 15696-15607, 2019; Moutal et al., *Pain*. 158: 2203-2221, 2017). Peptide arrays were washed 3 times for 5 minutes at RT with TBST and incubated with the primary antibody anti-VAPA (RRID AB_2722707; UC Davis/NIH NeuroMab Facility) for 2 hours at RT with gentle shaking in TBST, 5% BSA. After washing with TBST, the membranes were incubated in secondary antibody (IRDye® 800CW goat anti-mouse IgG secondary antibody; RRID AB_621842; Li-Cor) for 45 minutes, washed 3 times for 5 minutes in TBST, and visualized by infrared fluorescence (Li-Cor). Four independent peptide spot arrays were used in this study. Fluorescence intensity was analyzed with Image studio (Li-Cor).

Statistical Analyses

Data are presented as mean±SEM. All statistical analysis was performed in GraphPad Prism 7 (GraphPad, San Diego, Calif.) or BioVinci data analysis software. For comparison of two sample means, an unpaired two-tailed t-test was utilized for parametric data; Mann-Whitney tests were utilized for nonparametric data. For comparison of more than two sample means, a one-way ANOVA with Bonferroni's multiple comparison test (MCT) for relevant comparisons; Kruskal-Wallis tests with Dunn's MCT were utilized for nonparametric data. For behavioral studies, a two-way ANOVA was utilized to compare a peptide-treatment effect between the two sample cohorts.

Example 2

Kv2.2-Derived Neuroprotective Peptide Induces Declustering of Kv2.1 Channels

This example describes the identification of a seven amino acid sequence within the Kv2.2 CT responsible for mediating Kv2.1 cluster dispersal and further describes the development of an injectable, blood-brain-barrier-permeant, neuroprotective therapeutic peptide (TAT-DP-2) based on this sequence. It is shown that TAT-DP-2 provides robust neuroprotection in vitro. Additionally, the first evidence of targeted-disruption of Kv2.1 surface clusters as a neuroprotective strategy in vivo is provided by showing that TAT-DP-2 administration following ischemic stroke confers robust neuroprotection in mice. As evidence suggests that the endoplasmic reticulum vesicle-associated membrane protein-associated protein A (VAPA) recruits Kv2.1 to the clusters (Kirmiz, et al., *J Neurosci*. 38: 7562-7584, 2018; Johnson et al., *Proc Natl Acad Sci USA*. 115: E7331-E7340, 2018; Johnson, et al., *Channels (Austin)*. 13: 88-101, 2019), it is further demonstrated that DP-2 disrupts this interaction, without directly binding VAPA.

Identification and Characterization of a Kv2.1 Declustering Peptide

Figures 7A, 7B:
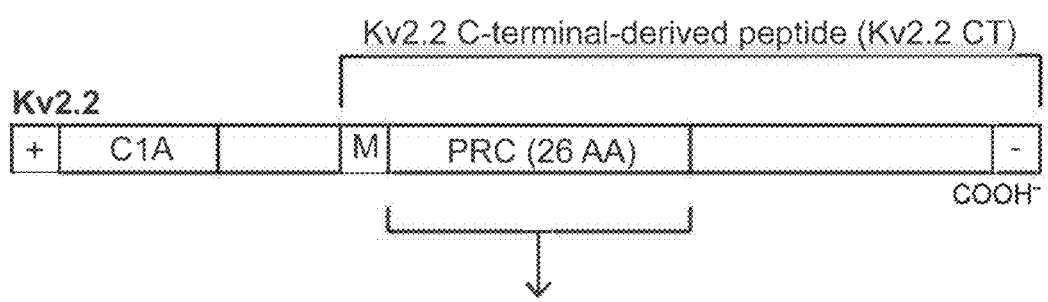
FIGS. 7A-7D: Synthesis strategy for declustering peptides.

First, the minimal sequence within Kv2.2 CT that mediates Kv2.1 declustering (Baver, et al., *Neuroscience*. 217: 56-66, 2012) and neuroprotection (Justice et al., *Neuroscience*. 354: 158-167, 2017) was defined. To accomplish this, the C-terminal (CT) domains of both Kv2.2 (FIG. 7A) and Kv2.1 were analyzed, focusing on the amino acid residues known to be critical for Kv2 channel surface cluster formation (Lim, et al., *Neuron*. 25: 385-397, 2000). Both Kv2.1 and Kv2.2 C-terminal sequences contain a highly homologous segment involved in cluster formation, known as the proximal restriction and clustering (PRC) domain (Lim, et al., *Neuron*. 25: 385-397, 2000) (FIG. 7B). Specifically, four critical residues exist within the PRC domain of Kv2.1 (S587, S590, F591, and S593; rat sequence, Uniprot P15387; SEQ ID NO: 32), that when point-mutated, abolish the ability for Kv2.1 to form clusters in neurons (Lim, et al., *Neuron*. 25: 385-397, 2000). A seven amino acid sequence that includes these four residues from Kv2.1 (aa 587-593; SIDSFIS, residues 587-593 of SEQ ID NO: 32), differs only by a single amino acid in the analogous segment of Kv2.2 CT (aa 602-608; SIDSFTS, residues 11-17 of SEQ ID NO: 29). These sequences are also conserved for both Kv2.1 and Kv2.2 channels in mouse (Uniprot Q03717 (SEQ ID NO: 39) and Uniprot A6H8H5 (SEQ ID NO: 40), respectively) and human (Uniprot Q14721 (SEQ ID NO: 41) and Uniprot Q92953 (SEQ ID NO: 42), respectively).

With this information, it was hypothesized that the region encompassing amino acids 602-608 within Kv2.2 CT was most likely to be responsible for disrupting Kv2.1 clusters, likely by outcompeting a "cluster targeting" sequence on existing channels that recruited them to the cluster microdomain. Indeed, Kv2.1 and Kv2.2 target to somatodendritic clusters via non-canonical two-phenylalanine in an acidic tract (FFAT) motif sequences, namely SFISCAT (SEQ ID NO: 33) and SFTSCAT (SEQ ID NO: 34) (Kirmiz, et al., *J Neurosci*. 38: 7562-7584, 2018; Johnson et al., *Proc Natl Acad Sci USA*. 115: E7331-E7340, 2018; Johnson, et al., *Channels (Austin)*. 13: 88-101, 2019), which overlap substantially with the proposed domain (FIG. 7B). These sequences interact with the ER-linker vesicle-associated membrane protein-associated proteins (VAPs) (Kirmiz, et al., *J Neurosci*. 38: 7562-7584, 2018; Johnson, et al., *Channels (Austin)*. 13: 88-101, 2019). As these sequences omit one residue strongly implicated in cluster formation (S602 in Kv2.2 and S587 in Kv2.1), a sequence that includes all four pro-clustering residues was evaluated (FIG. 7C), generating the declustering peptide, DP-2 (SIDSFTS; SEQ ID NO: 1), and its scrambled control, Sc-2 (DFSSIST; SEQ ID NO: 35).

Figure 1C:
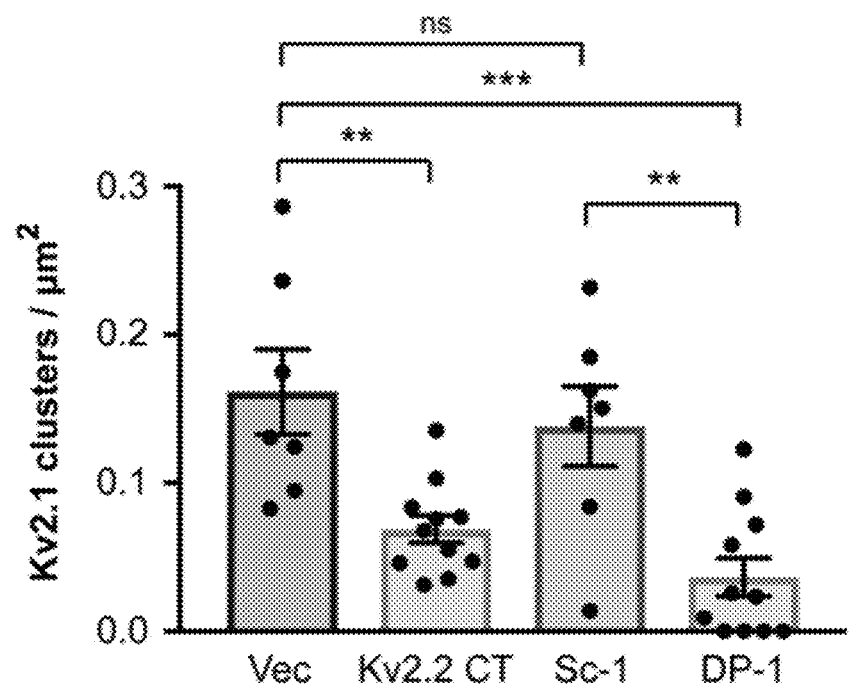
Figure 7C:
Figure 7C:
Figure 7D:
Figure 7D:

Plasmids encoding the DP-2 and Sc-2 sequences were generated for comparative purposes, as prior work had utilized a Kv2.2 CT-expressing vector to decluster Kv2.1 channels (O'Connell, et al., *Proc Natl Acad Sci USA*. 107: 12351-12356, 2010; Justice et al., *Neuroscience*. 354: 158-167, 2017). These expression vectors include the native upstream sequence containing the most proximal methionine to act as the start codon. When expressed, the putative declustering peptide (DP-1) and its scrambled control (Sc-1) are MKSTSSIDSFTS (SEQ ID NO: 27) and MKSTSDFS-SIST (SEQ ID NO: 28), respectively (FIGS. 7D and 1A). These were tested first for their declustering properties by transfecting primary cortical neurons with a GFP-tagged Kv2.1 construct, which produces somatodendritic Kv2.1 channel clusters similar, albeit not identical, to endogenous channels (O'Connell, et al., *J Neurosci*. 26: 9609-9618, 2006). Neurons were first co-transfected with either empty-vector (pcDNA3), Kv2.2 CT-expressing plasmid (pCMV-Kv2.2CT), DP-1-expressing plasmid (pCMV-DP-1), or Sc-1-expressing plasmid (pCMV-Sc-1). Twenty-four hours following transfection, Kv2.1 cluster densities were analyzed. When compared to empty vector-expressing or Sc-1-expressing neurons, it was found that both Kv2.2 CT and DP-1 expression similarly resulted in significant Kv2.1 cluster dispersal (FIGS. 1B and 1C). These results suggest that a short sequence within Kv2.2 CT, contained within the DP-1 peptide, is sufficient for dispersal of Kv2.1 surface clusters in vitro.

Figure 2A:
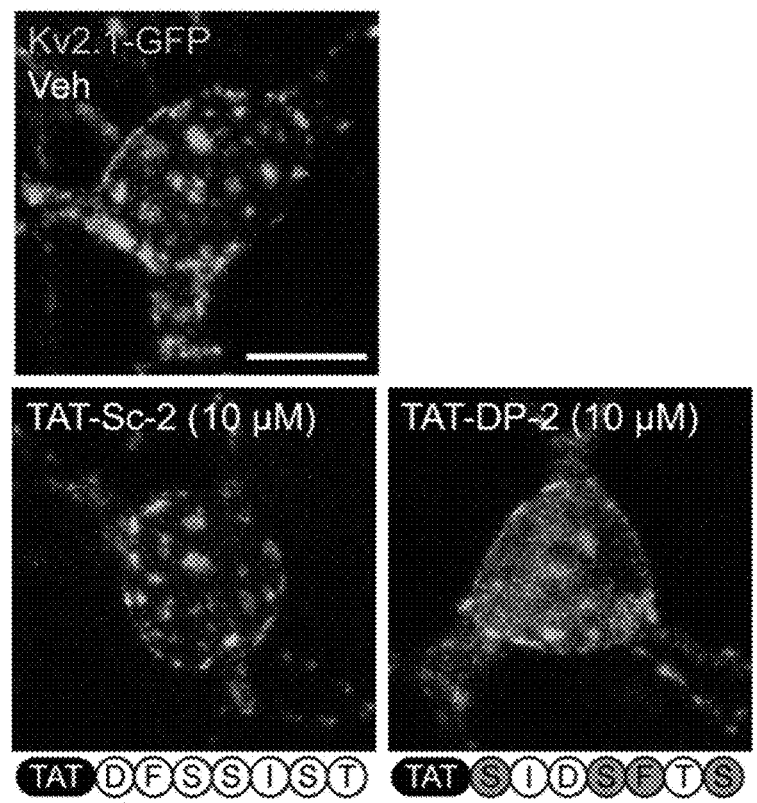
FIGS. 2A-2B: Treatment of cortical neurons with TAT-DP-2 induces Kv2.1 declustering.
Figure 2B:
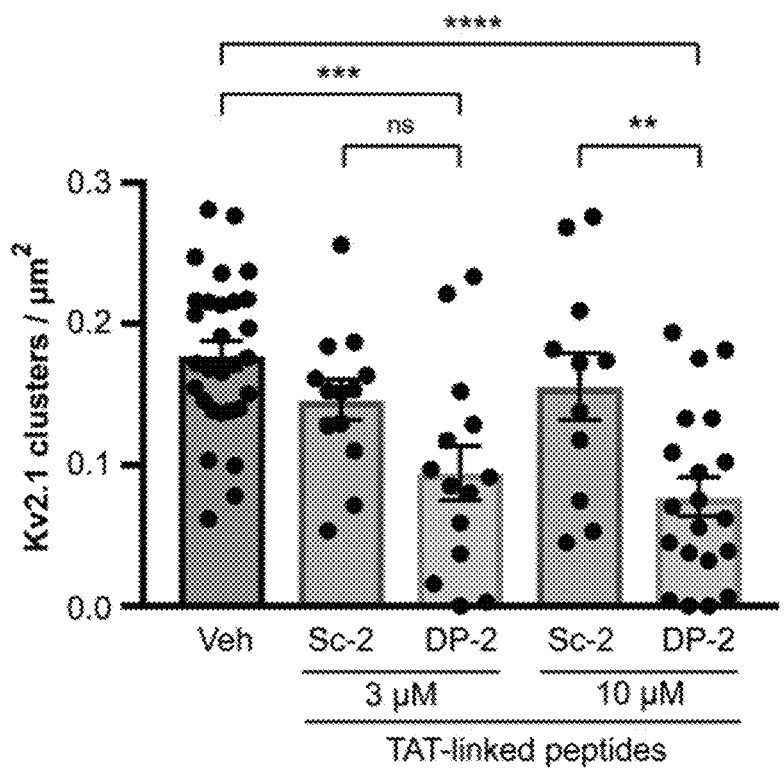
Figure 9:
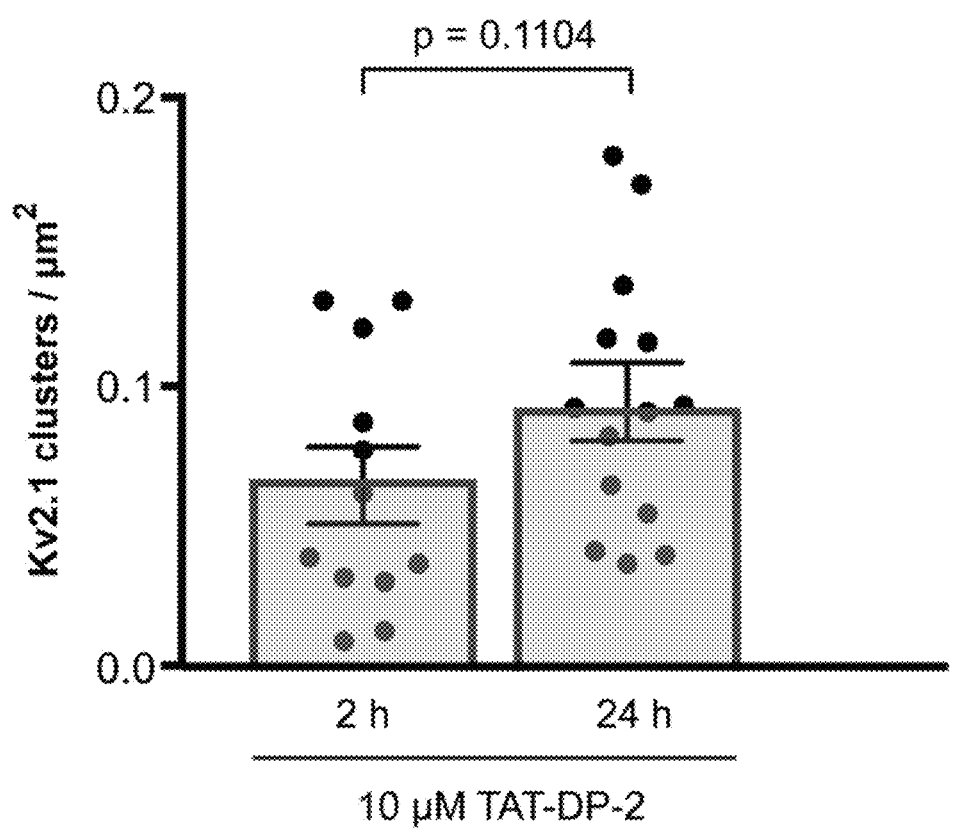
FIG. 9: Re-clustering of Kv2.1 24 hours following TAT-DP-2 treatment. Groups indicate time after initiation of TAT-DP-2 treatment. Following two-hour treatment, 10 µM TAT-DP-2 is removed from the culture through medium replacement. An appreciable trend of Kv2.1 re-clustering was observed at 24 hours. Bar graph represents mean Kv2.1 surface cluster density (#Kv2.1 clusters/µm$^2$ of neuronal soma), displayed as mean+/−SEM (2 h, 0.06±0.01, n=12; 24 h, 0.09±0.01, n=14). Analyzed via unpaired t-test (2 h vs. 24 h, $p=0.1104$).
Figure 11A:
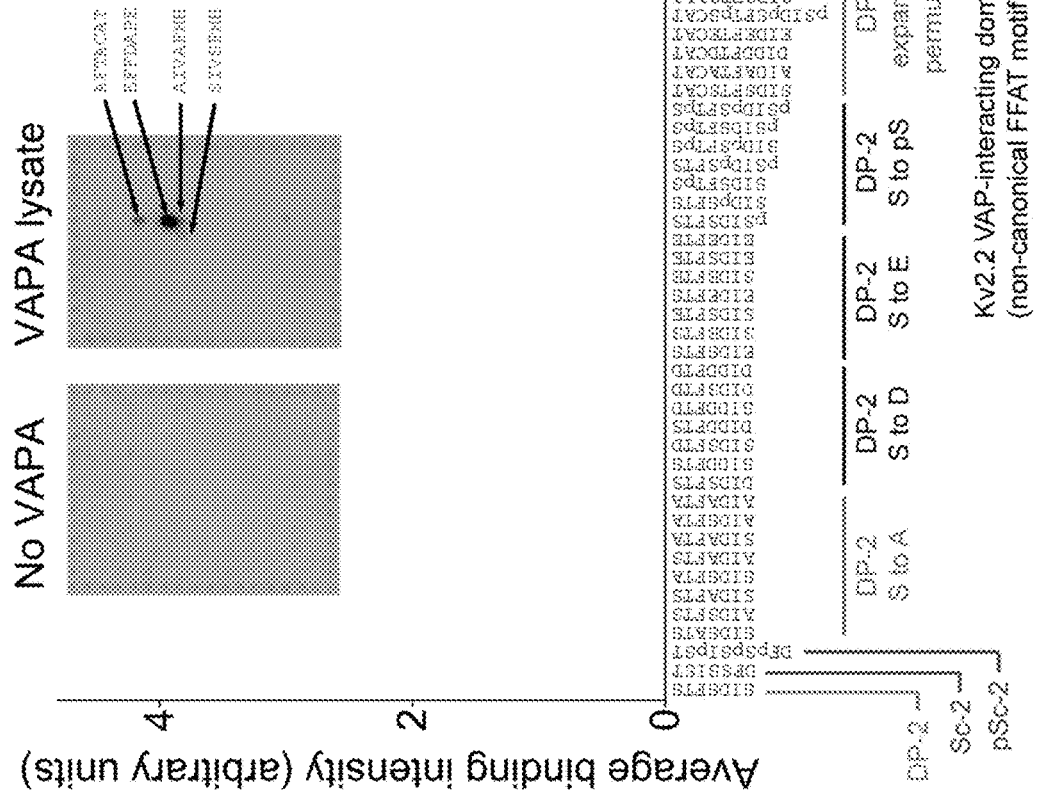
FIGS. 11A-11C: DP-2 does not bind VAPA in a cell-free peptide spot assay.
Figure 11B:
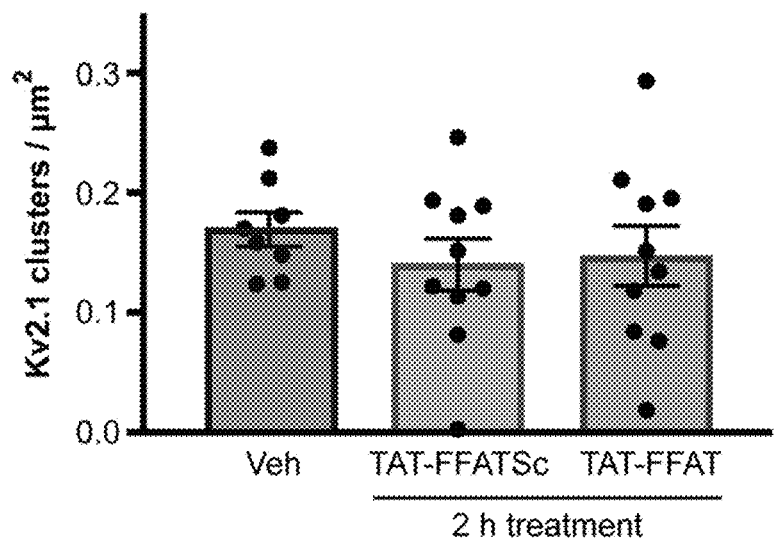
Figure 11C:
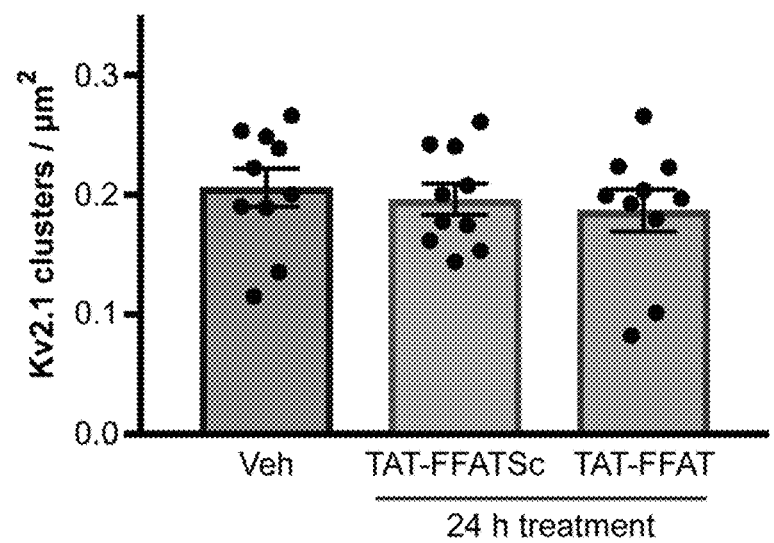

In order to test the hypothesis that SIDSFTS (DP-2; SEQ ID NO: 1) was the minimal sequence responsible for Kv2.1 declustering, a cell-permeant, TAT-linked derivative of DP-2 (TAT-DP-2) was generated, as well as a scramble control (TAT-Sc-2; FIG. 7C). TAT (transactivator of transcription: YGRKKRRQRRR, SEQ ID NO: 31), is a cell-penetrating peptide derived from HIV-1 (Schwarze, et al., *Science*. 285: 1569-1572, 1999). To assess the ability of TAT-DP-2 treatment to induce rapid dispersal of Kv2.1 clusters, cortical neurons were co-transfected with a GFP-tagged Kv2.1 construct. Twenty-four hours following transfection, neurons were treated with either TAT-DP-2, TAT-Sc-2, or vehicle for two hours. It was found that TAT-DP-2 (10 μM) induced a time-dependent (FIGS. 8A and 8B) dispersal of Kv2.1 surface clusters, with significant declustering observed at two hours when compared with either vehicle or TAT-Sc-2 (10 μM) treatment (FIGS. 2A and 2B). Lower concentrations of TAT-DP-2 (3 μM) induced significant dispersal of Kv2.1 surface clusters, but only when compared to vehicle-treated neurons. As such, it was hypothesized that TAT-DP-2 is an effective in vitro declustering tool at concentrations between 3-10 μM. Kv2.1 clusters appeared to remain dispersed up to 24 hours following initial treatment with TAT-DP-2, although to a lesser degree, indicating that this effect is likely reversible (FIG. 9). The ability of TAT-DP-2 to decluster endogenous Kv2.1 channels in cortical neurons in vitro was confirmed by immunocytochemistry (FIG. 10).
DP-2 Alone Does Not Bind to VAPA but Effectively Disrupts Kv2.1-VAPA Association Kv2.1 and Kv2.2 channels are recruited to ER-PM junctions via C-terminal PRC-mediated interaction with vesicle-associated membrane protein (VAMP)-associated protein A/B (VAPA/B) (Kirmiz, et al., *J Neurosci.* 38: 7562-7584, 2018; Johnson et al., *Proc Natl Acad Sci USA.* 115: E7331-E7340, 2018; Johnson, et al., *Channels (Austin).* 13: 88-101, 2019). This process occurs at non-canonical FFAT binding motifs within the PRC domains of Kv2.1 and Kv2.2 (FIG. 7B), which are recruited to the FFAT binding domain on VAPA/B (Kirmiz, et al., *J Neurosci.* 38: 7562-7584, 2018; Johnson et al., *Proc Natl Acad Sci USA.* 115: E7331-E7340, 2018; Johnson, et al., *Channels (Austin).* 13: 88-101, 2019). A peptide spot array assay (Brittain et al., *Nat Med.* 17: 822-829, 2011) was utilized to assess the ability of DP-2, along with many mutant variants of the peptide (see below; FIG. 11A), to bind VAPA in a cell-free assay. Despite the fact that non-canonical FFAT motifs SFISCAT (SEQ ID NO: 33) and SFTSCAT (SEQ ID NO: 34) are required for Kv2.1 and Kv2.2 interaction with VAP proteins, no binding between these peptides and VAPA was observed (FIG. 11A). Moreover, no binding between VAPA and DP-2 was observed. These data indicate that both the DP-2 sequence, as well as the non-canonical FFAT motifs located on Kv2.1 and Kv2.2, may not be sufficient for VAPA binding alone, at least in a cell-free environment. The assay was validated by observing strong VAPA binding to the positive control peptide (EFFDAPE; SEQ ID NO: 36), a canonical FFAT motif.

Given these results, further testing was conducting to determine whether a TAT-linked derivative of the canonical FFAT motif (TAT-FFAT; YGRKKRRQRRREFFDAPE, SEQ ID NO: 37) could disrupt Kv2.1 surface cluster formation. GFP-Kv2.1-transfected neurons were treated with TAT-FFAT (10 µM) or scramble control peptide TAT-FFATSc (YGRKKRRQRRRDEEFAP, SEQ ID NO: 38; 10 µM) for either two or 24 hours and analyzed for Kv2.1 cluster density. As TAT-FFAT treatment did not induce Kv2.1 cluster dispersal (FIGS. 11B and 11C) when compared with a scrambled sequence peptide, these results suggest that a more complex interaction between VAPA and Kv2.1 may be at play.

Selective serine phosphorylation of Kv2.1 within its PRC domain appears critical for its recruitment by VAP proteins, most notably S590 (S605 on Kv2.2) (Kirmiz, et al., *J Neurosci.* 38: 7562-7584, 2018; Johnson et al., *Proc Natl Acad Sci USA.* 115: E7331-E7340, 2018; Johnson, et al., *Channels (Austin).* 13: 88-101, 2019). Indeed, CD4-linked chimeras of Kv2.1 PRC domain peptides localize to VAPA proteins at the endoplasmic reticulum, an effect abolished by selective serine-to-alanine mutations within the PRC domain (Johnson, et al., *Channels (Austin).* 13: 88-101, 2019). Conversely, mutation of these same residues to aspartic acid restores CD4-linked PRC-VAPA interaction (Johnson, et al., *Channels (Austin).* 13: 88-101, 2019). Although these phosphorylation events had been proposed to render the PRC domain as containing non-canonical FFAT motifs (Kirmiz, et al., *J Neurosci.* 38: 7562-7584, 2018; Johnson et al., *Proc Natl Acad Sci USA.* 115: E7331-E7340, 2018; Johnson, et al., *Channels (Austin).* 13: 88-101, 2019), demonstrable binding to VAPA was not observed with these amino acid sequences in the peptide array. In fact, the pseudo-phosphorylated mutant DP-2 peptide sequences lacked VAPA binding capacity in the peptide spot array assay (FIG. 11A). Regardless of the observed lack of VAPA binding, a TAT-linked peptide containing serine to aspartate mutations (TAT-DP-2D: YGRKKRRQRRRDIDDFTD; SEQ ID NO: 26) effectively declustered Kv2.1-GFP aggregates in neurons, while the serine to alanine mutant (TAT-DP-2A: YGRKKRRQRRRAIDAFTA; SEQ ID NO: 25) did not (FIGS. 12A and 12B). Taken together, these results strongly indicate that TAT-DP-2-mediated Kv2.1 declustering relies on phosphorylation of serine residues, although this sequence alone is not sufficient to bind to VAPA (FIG. 11A), implicating a multifaceted architecture underlying the interaction between Kv2.1 and its associated ER binding partner.

Figure 3A:
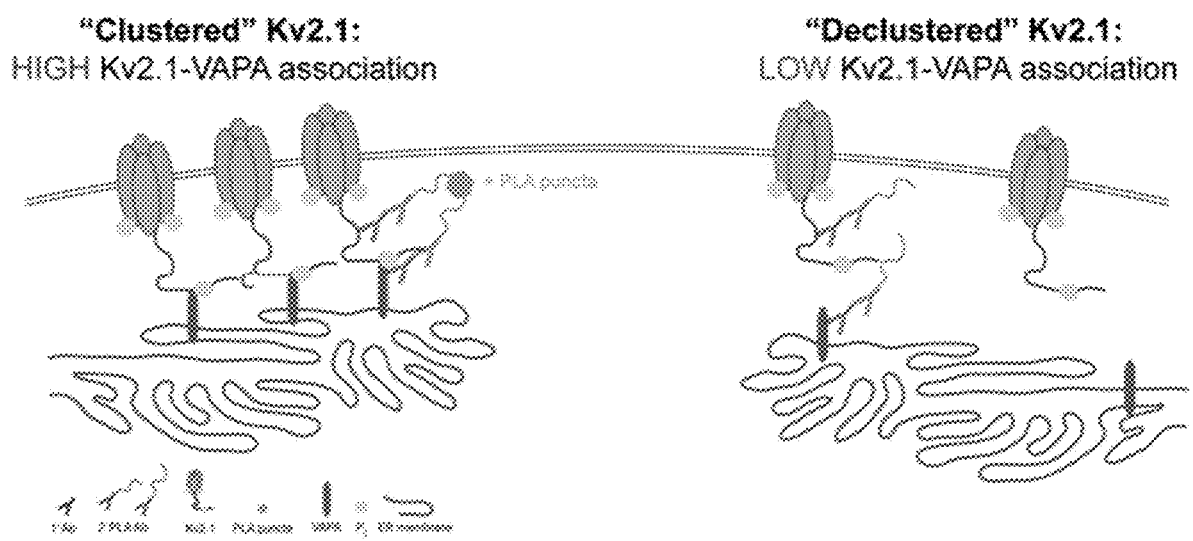
FIGS. 3A-3C: TAT-DP-2 displaces Kv2.1-VAPA association in cortical neurons.
Figure 3B:
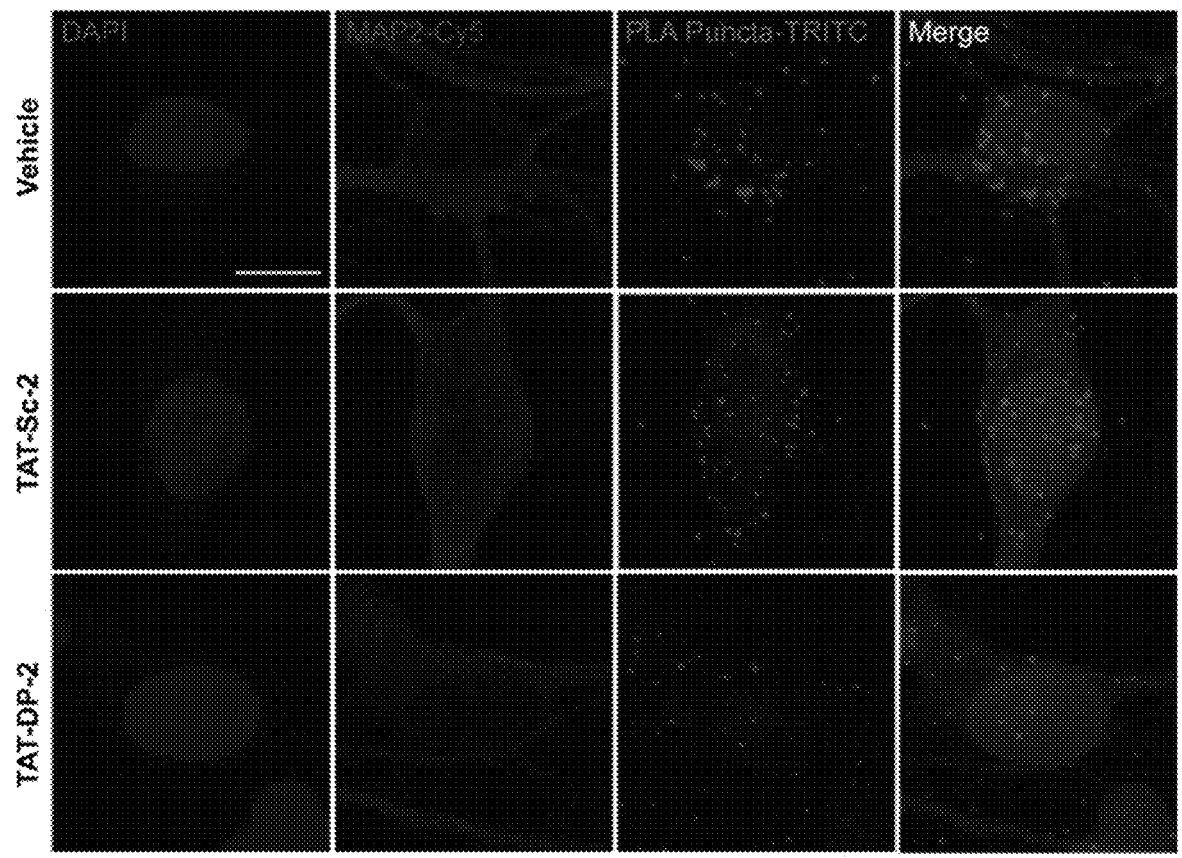
Figure 3C:
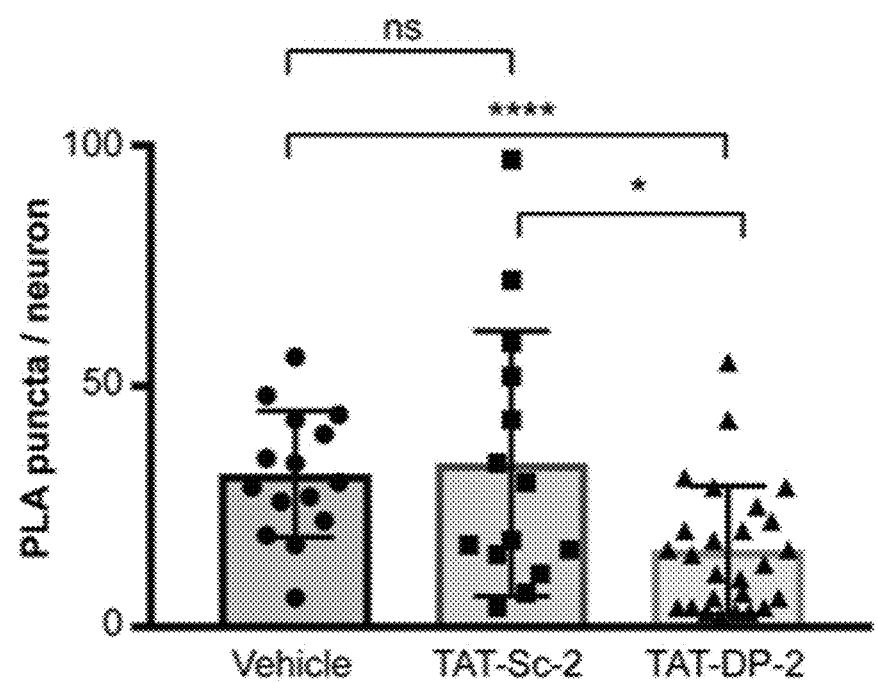

In spite of the lack of demonstrable direct binding between TAT-DP-2 and VAPA, it was evaluated whether TAT-DP-2 could still disrupt the Kv2.1-VAPA interaction in vitro, given its strong declustering effect. A proximity ligation assay (PLA; FIG. 3A), which allows for analysis of protein-protein association at distances less than 40 nm from each other (Söderberg et al., *Methods.* 45: 227-232, 2008), was utilized. Cortical neurons were treated with vehicle, TAT-Sc-2 (10 µM), or TAT-DP-2 (10 µM) for 2 hours. Following treatment, a PLA staining protocol was utilized that allowed for fluorescent labeling of Kv2.1-VAPA association, based on published methods (Söderberg et al., *Methods.* 45: 227-232, 2008). Robust fluorescent PLA puncta formation was observed in both vehicle and TAT-Sc-2-treated neurons (FIGS. 3B and 3C), indicating a high level of Kv2.1-VAPA association. In contrast, TAT-DP-2 exposure induced a significant reduction in PLA reactions (FIGS. 3B and 3C), demonstrating that this peptide alone could effectively disrupt Kv2.1-VAPA association, seemingly without directly binding to VAPA.

TAT-DP-2 Prevents Enhancement of Kv2.1-Mediated Pro-Apoptotic Potassium Currents and is Neuroprotective In Vitro The cell death-enabling loss of intracellular potassium in neurons can be experimentally monitored as a time-dependent enhancement in Kv2.1-mediated potassium currents under whole-cell voltage clamp conditions as new channels become incorporated into the plasma membrane (Pal, et al., *J Neurosci.* 23: 4798-4802, 2003; Pal, et al., *Cell Death Differ.* 13: 661-667, 2006; McLaughlin et al., *J Neurosci.* 21: 3303-3311, 2001). In order to evaluate whether TAT-DP-2-induced declustering could prevent the apoptotic enhancement of potassium currents in a manner akin to Kv2.2 CT overexpression (Justice et al., *Neuroscience.* 354: 158-167, 2017), cortical neurons were treated in vitro with either TAT-DP-2 (10 µM), TAT-Sc-2 (10 µM), or vehicle for two hours prior to a two-hour exposure to DL-threo-β-benzyloxyaspartic acid (TBOA; 60 µM) or vehicle. TBOA is a glutamate transporter inhibitor that produces a slow excitotoxic injury via prolonged NMDA receptor stimulation (Bonfoco, et al., *Proc Natl Acad Sci USA.* 92: 7162-7166, 1995). This induces a pronounced potassium current surge mediated by Kv2.1, culminating in delayed apoptotic cell death, mimicking the excitotoxic conditions present in the ischemic penumbra following stroke (Yeh et al., *J Neurosci.* 37: 5648-5658, 2017; Yeh et al., *Proc Natl Acad Sci USA.* 116: 15696-15607, 2019; Justice et al., *Neuroscience.* 354: 158-167, 2017; Bonfoco, et al., *Proc Natl Acad Sci USA.* 92: 7162-7166, 1995).

Figure 4A:
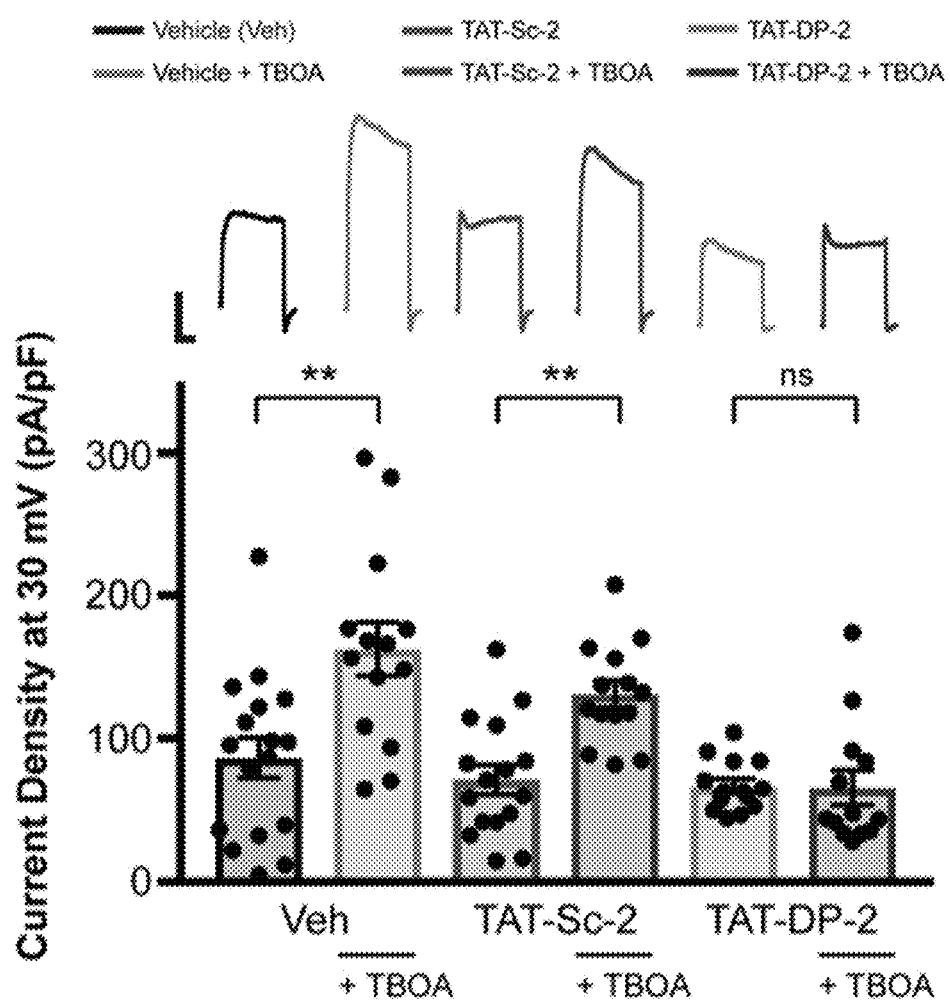
FIGS. 4A-4D: Treatment of cortical neurons with TAT-DP-2 blocks pro-apoptotic increases in Kv2.1-mediated potassium currents and is neuroprotective against apoptotic insults.
Figure 4B:
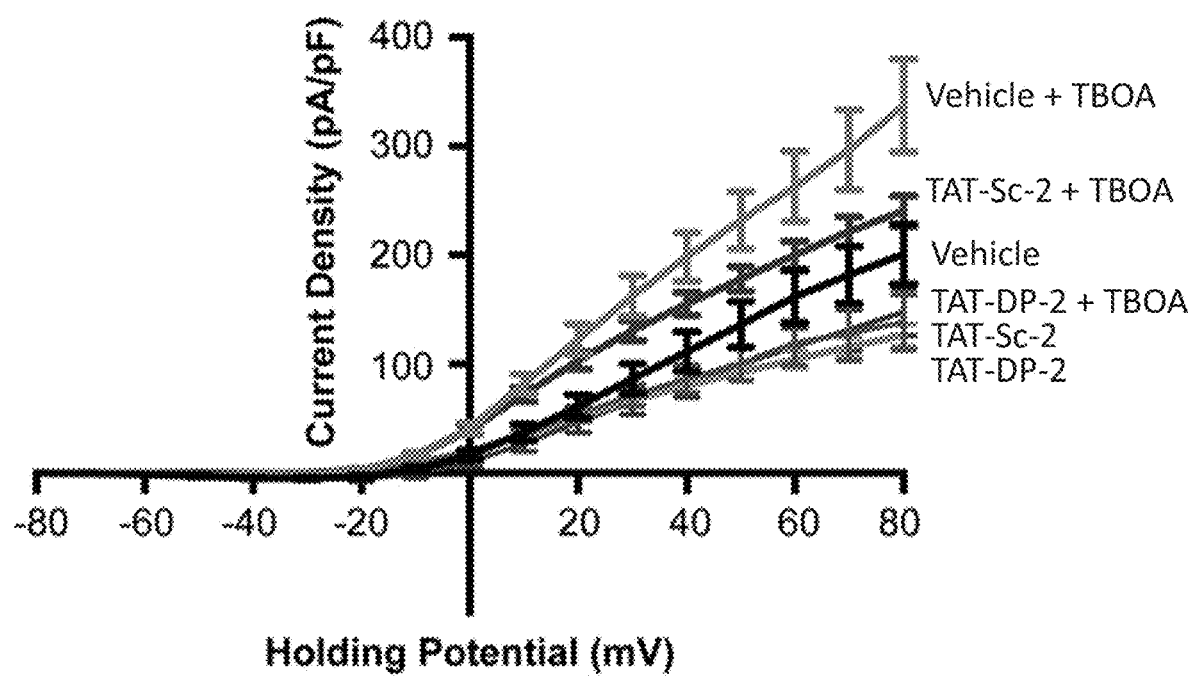
Figure 4C:
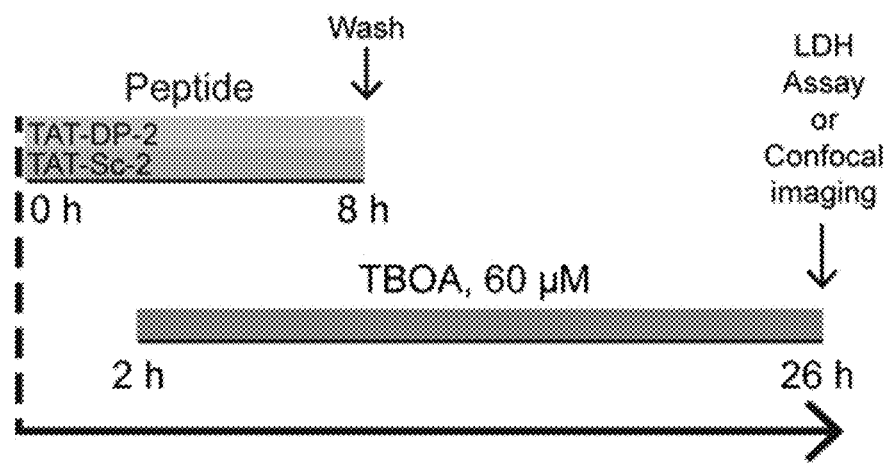

Delayed-rectifier potassium currents, which are primarily mediated by Kv2.1 in the preparation (Pal, et al., *J Neurosci.* 23: 4798-4802, 2003), were monitored three to five hours following TBOA exposure. Kv2.1 current densities were significantly increased in the vehicle/TBOA-treated cells when compared with the vehicle/vehicle-treated group (FIGS. 4A and 4B). An identical effect was also seen when comparing the TAT-Sc-2/vehicle-treated group with the TAT-Sc-2/TBOA-treated cells. Strikingly, treatment with TAT-DP-2 completely abolished TBOA-mediated enhancement of Kv2.1 current densities as no differences were noted between TAT-DP-2/vehicle-treated neurons and TAT-DP-2/TBOA-exposed cells. These results support the notion that DP-2-mediated Kv2.1 declustering can effectively prevent the apoptotic surge of potassium currents in neurons by disrupting their membrane-insertion platform. It is also noteworthy that baseline Kv2.1 current densities were unaffected by the peptide treatment, demonstrating that the injury-mediated insertion of Kv2.1 channels and the normal trafficking of the channel occur via distinct processes, as has been repeatedly experimentally ascertained in prior work (Pal, et al., *J Neurosci.* 23: 4798-4802, 2003; Pal, et al., *Cell Death Differ.* 13: 661-667, 2006; Yeh et al., *J Neurosci.* 37: 5648-5658, 2017).

Figure 4D:
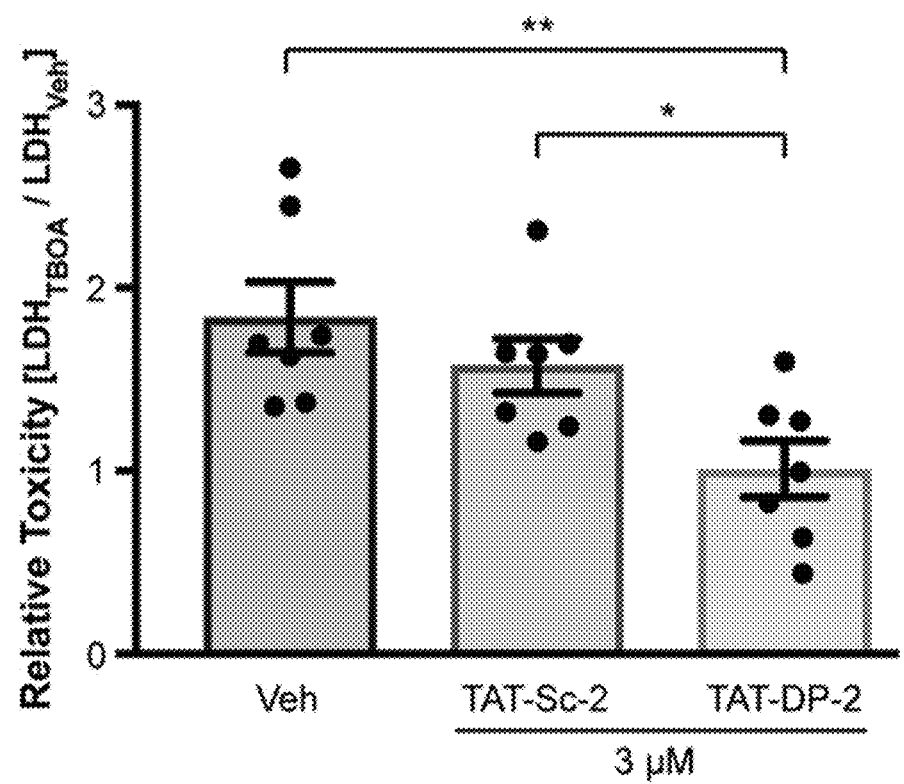
Figure 5A:
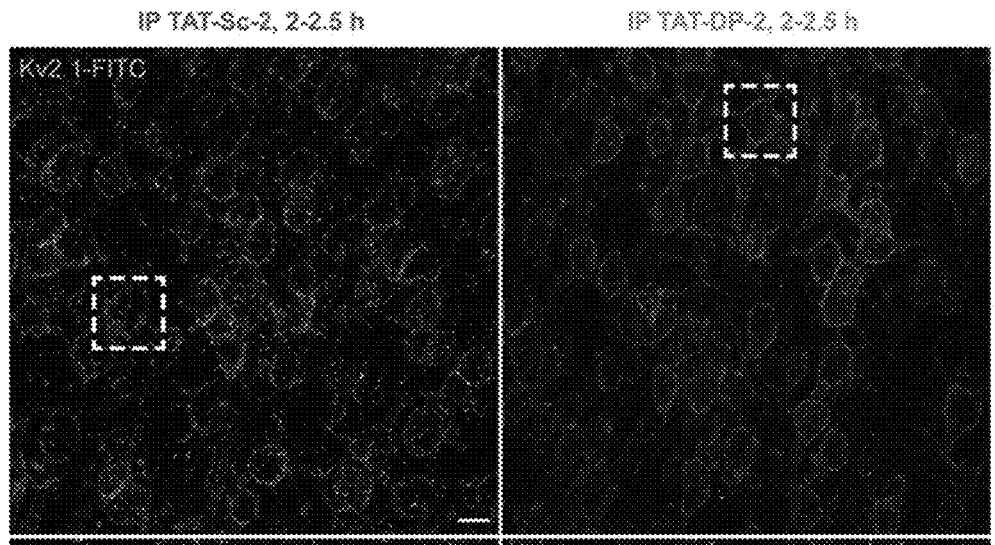
FIGS. 5A-5D: Intraperitoneal injection of TAT-linked DP-2 in mice induces rapid dispersal of Kv2.1 surface clusters.
Figure 5B:
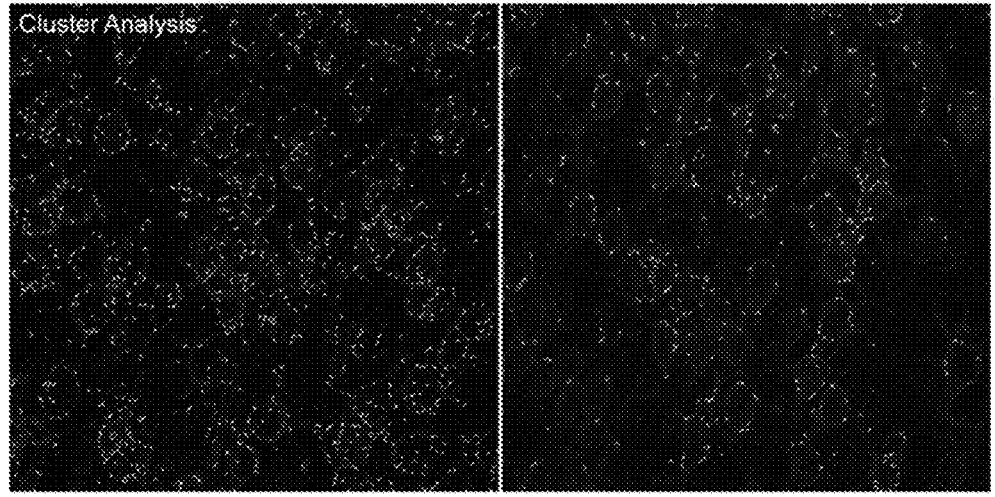
Figure 5C:
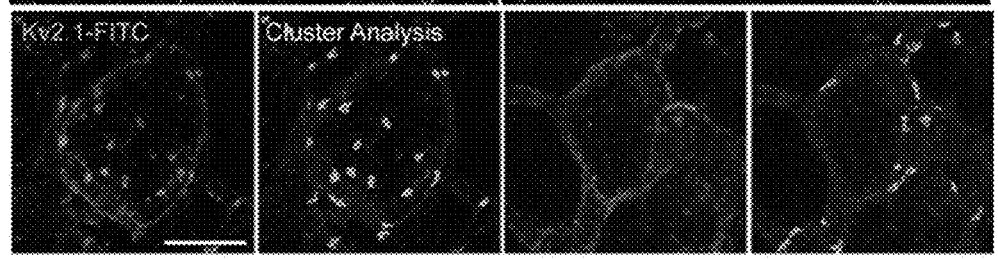
Figure 5D:
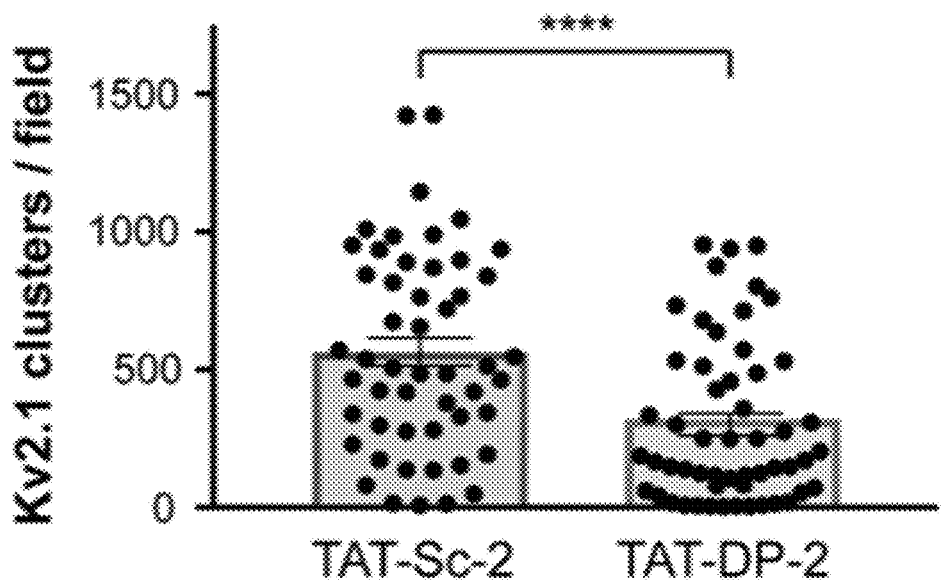

With evidence that TAT-DP-2-mediated declustering prevents enhancement of pro-apoptotic Kv2.1 potassium currents following injury, the neuroprotective actions of TAT-DP-2 in cortical neurons in vitro were next tested. Cells were exposed to either vehicle, TAT-DP-2 (3 µM), or TAT-Sc-2 (3 µM) for two hours prior to an overnight exposure to either vehicle or TBOA (60 µM). In addition to the pre-incubation period, peptides were present for the first four hours of the TBOA exposure (FIG. 4C), a period of time when current enhancement normally begins following initial injury (Pal, et al., *J Neurosci.* 23: 4798-4802, 2003; Pal, et al., *Cell Death Differ.* 13: 661-667, 2006). Neurotoxicity was assessed by the release of lactate dehydrogenase (LDH) into the culture medium, as described previously (Aras, et al., *Curr Protoc Neurosci.* 44: 7.18.1-7.18.15, 2008). Consistent with the observed inhibition of apoptotic potassium currents, TAT-DP-2, but not TAT-Sc-2, significantly attenuated TBOA-induced toxicity when compared to the scrambled peptide, measured as relative toxicity ratios ([LDH]$_{TBOA}$/[LDH]$_{Vehicle}$) (FIG. 4D). Based on these findings, the potential neuroprotective actions of TAT-DP-2 were evaluated in an in vivo model of ischemia-reperfusion injury, where a substantial contribution of Kv2.1-enabled neuronal cell death has been previously observed (Yeh et al., *J Neurosci.* 37: 5648-5658, 2017).

TAT-DP-2 Induces Rapid Dispersal of Kv2.1 Surface Clusters In Vivo and is Neuroprotective Following Cerebral Ischemia-Reperfusion Injury in Mice Previous studies have validated effective delivery of small TAT-linked peptides to the cerebral vasculature and brain parenchyma within several minutes following intraperitoneal injection (Yeh et al., *J Neurosci.* 37: 5648-5658, 2017). To determine whether TAT-DP-2 could decluster Kv2.1 channels in vivo, naïve young-adult male mice were injected with an intraperitoneal bolus of either TAT-DP-2 or TAT-Sc-2 (6 nmol/g). Two hours following injection, brain tissue was harvested for immunohistochemical staining of endogenous Kv2.1 channel distribution. It was found that Kv2.1 cluster density in layers ⅔ of the cerebral cortex was significantly diminished in animals injected with TAT-DP-2, when compared with TAT-Sc-2-injected animals (FIGS. 5A-5D), indicating effective TAT-DP-2-mediated Kv2.1 declustering in vivo.

The neuroprotective efficacy of TAT-DP-2 in vivo was next tested. A transient, unilateral middle cerebral artery occlusion (MCAo) mouse model of ischemic stroke was used, which produces a highly reproducible infarct lesion involving both the striatum and cortex ipsilateral to the occlusion (Uluc, et al., *J Vis Exp.* 48: 1978, 2011), with a significant Kv2.1-dependent cell death component (Yeh et al., *J Neurosci.* 37: 5648-5658, 2017). The experimental design for these studies (FIG. 6A) includes subjecting animals to 50 minutes of MCAo, followed by reperfusion. TAT-DP-2 was administered at one and six hours following the initiation of reperfusion (two hours post-vessel occlusion), as this temporal setup may recapitulate a realistic and translatable therapeutic treatment window for stroke patients undergoing thrombolytic or endovascular procedures (Hill et al., *The Lancet.* 395: 878-887, 2020). As pro-apoptotic Kv2.1 current enhancement likely occurs three to five hours following ischemic injury (Pal, et al., *J Neurosci.* 23: 4798-4802, 2003; Pal, et al., *Cell Death Differ.* 13: 661-667, 2006), the goal was also to capture this critical event, ensuring that Kv2.1 clusters acting as insertion platforms for new channels reaching the membrane were adequately disrupted.

Figure 6A:
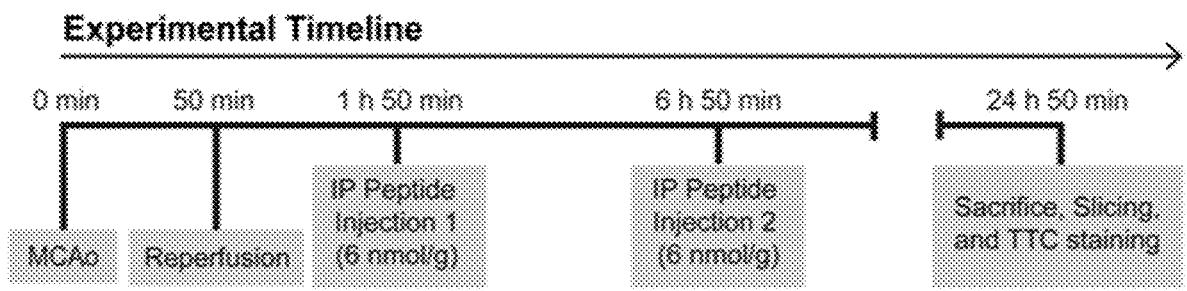
FIGS. 6A-6E: Intraperitoneal injection of mice with TAT-DP-2 following transient middle cerebral artery stroke reduces cerebral infarct volume.
Figure 6B:
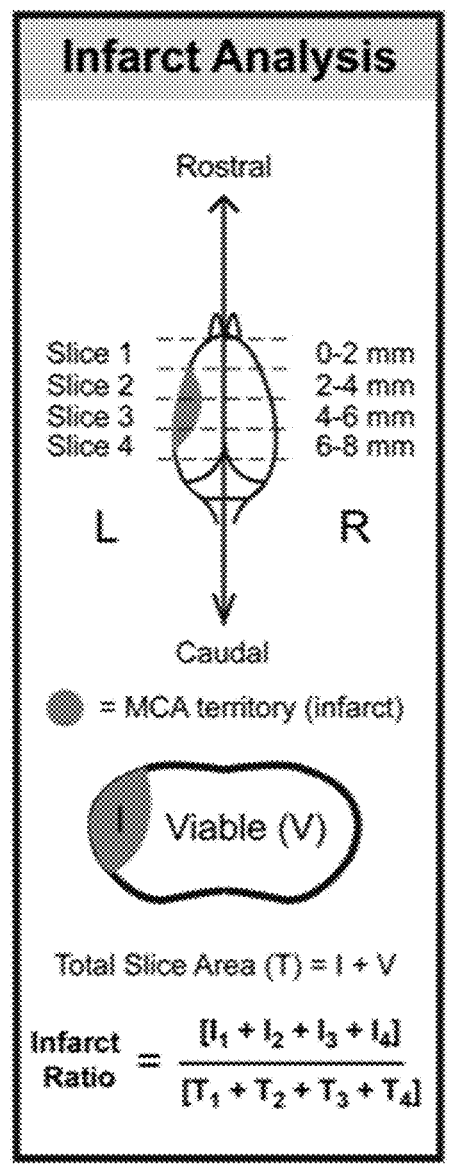
Figure 6C:
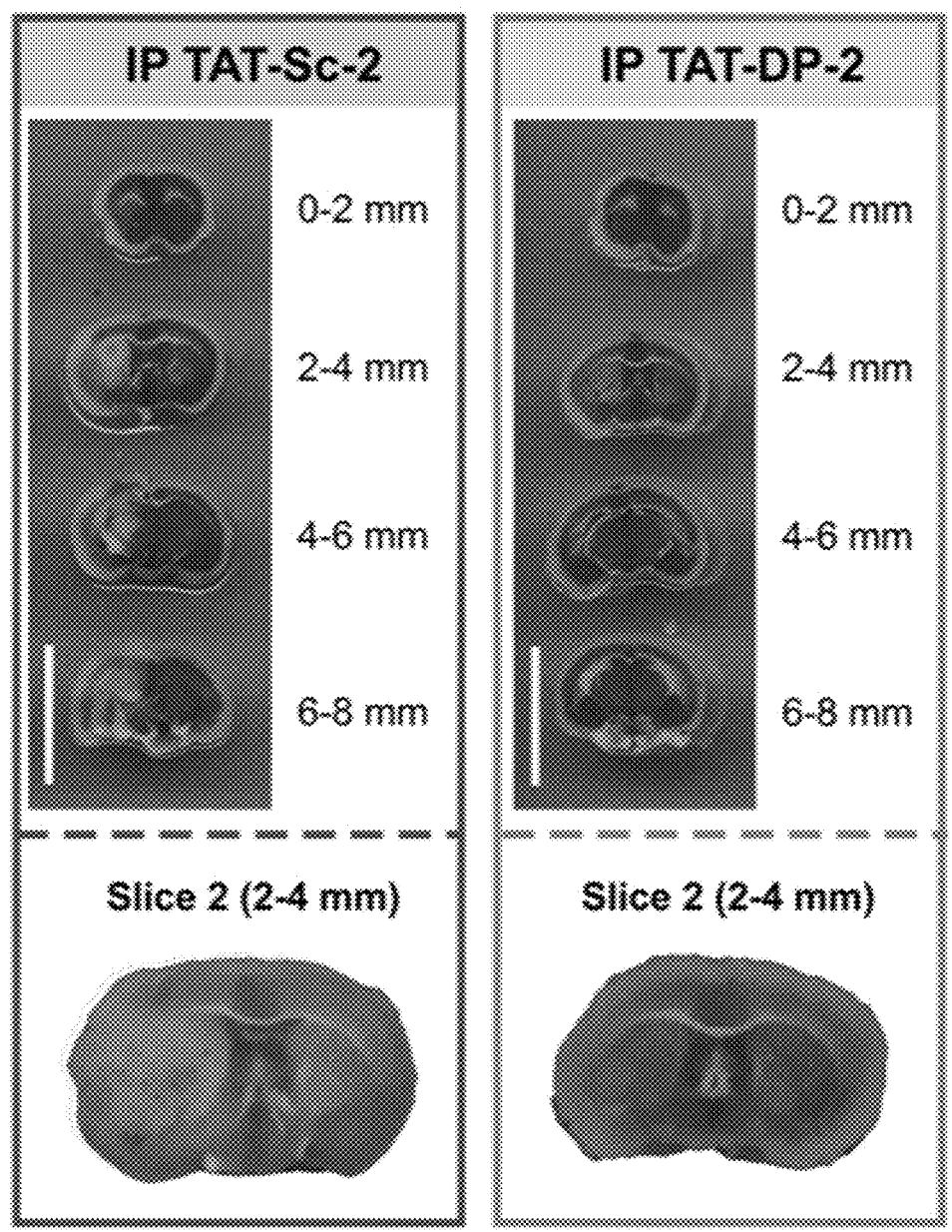
Figure 6D:
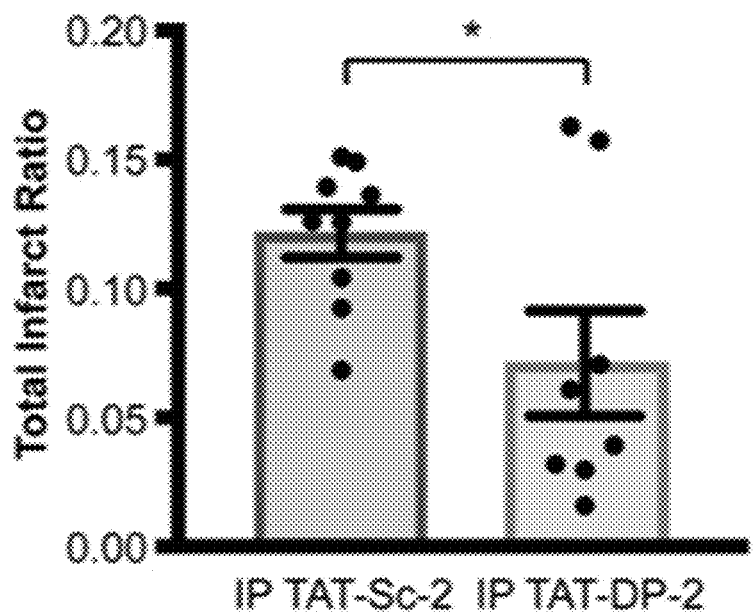
Figure 6E:
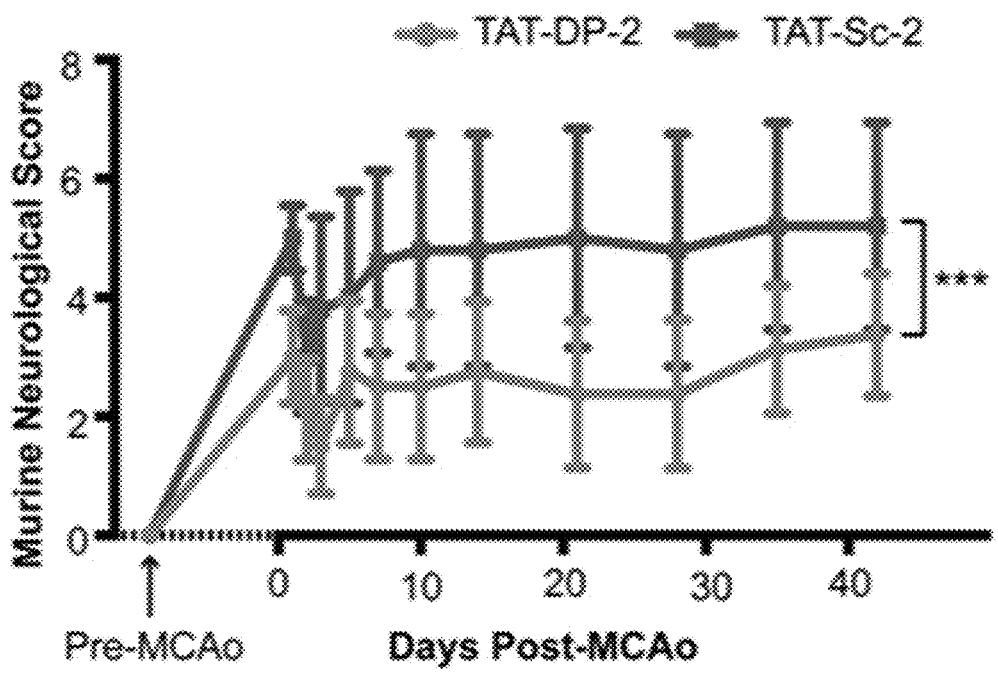

Twenty-four hours following cerebral reperfusion after MCAo, total infarct ratios were analyzed (FIG. 6B) in tetrazolium chloride-stained brain sections (FIGS. 6B and 6C). It was found that TAT-DP-2-treated mice exhibited a robust reduction in total cerebral infarct ratio compared to TAT-Sc-2-treated animals, consistent with effective TAT-DP-2-mediated neuroprotection previously observed in vitro (FIG. 6D). Preparation of peptides, MCAo surgery and injection, as well as infarct analysis were all randomized and performed blindly. A second cohort of mice was subjected to 50-minute MCAo, followed by TAT-DP-2 or TAT-Sc-2 injection at one and six-hours post-reperfusion (FIG. 6A). A different, blinded observer then analyzed each animal and assigned an objective murine neurological score (MNS; Table 3) to each mouse over a 42-day period. As the MNS is based solely on characteristic motor deficits developed following left MCAo, all animals initially scored zero on the scale. It was found that TAT-DP-2 treatment provided significant preservation of favorable neurological score when compared to scrambled control (FIG. 6E). As such, these data demonstrate a robust neuroprotective effect of TAT-DP-2 in vivo that not only reduces cerebral infarct lesion size, but also preserves long-term neurological function following cerebrovascular injury in a preclinical model of stroke.

Discussion

According to the World Health Organization, approximately 15 million people suffer from a stroke worldwide annually, with over five million dying and another five million suffering from permanent, serious disability. Current therapies for ischemic stroke are limited to rapid thrombolysis or endovascular thrombus removal in order to restore cerebral perfusion and prevent further brain infarction. This approach is a life-saving clinical procedure and positive outcomes have been reported with reperfusion delays of up to an astonishing 24 hours (Nogueira et al., *N Engl J Med.* 378: 708-718, 2018). This so-called "reperfusion-era" in stroke management has called for a re-evaluation of the optimal use of putative neuroprotective agents (Savitz, et al., *Stroke.* 48: 3413-3419, 2017), especially since restoration of blood flow following the infarction could contribute to reperfusion injury, exposing patients to oxidative stress capable of inducing secondary damage. As such, there is a critical need for the development of novel approaches to delayed neuroprotection which will supplement expedited cerebral reperfusion as a mainstay of therapy (Savitz, et al., *Stroke.* 48: 3413-3419, 2017). The studies disclosed herein targeted a key regulator of neuronal apoptosis within the ischemic penumbra: the Kv2.1 potassium channel. As Kv2.1-enabled cell death is likely delayed following the onset of injury (Pal, et al., *J Neurosci.* 23: 4798-4802, 2003; Pal, et al., *Cell Death Differ.* 13, 661-667, 2006; McLaughlin et al., *J Neurosci.* 21: 3303-3311, 2001), and occurs by a well-defined mechanism (FIGS. 13A and 13B), it offers an attractive therapeutic target for neuroprotection during the reperfusion and post-reperfusion period.

Following oxidative or nitrosative injury, free zinc displacement from metallothionein by reactive oxygen intermediate (ROI) species triggers dual phosphorylation of Kv2.1 channels by Src and p38, resulting in a calcium/CaMKII-dependent interaction between syntaxin and the proximal C-terminal domain of the channel (Pal, et al., *J Neurosci.* 23: 4798-4802, 2003; Pal, et al., *Cell Death Differ.* 13: 661-667, 2006; McCord et al., *J Physiol (Lond).* 592: 3511-3521, 2014; McLaughlin et al., *J Neurosci.* 21, 3303-3311, 2001; McCord, et al., *Proc Natl Acad Sci USA.* 110: 13988-13993, 2013; Redman, et al., *J Physiol (Lond).* 587: 4393-4404, 2009; Redman et al., *Proc Natl Acad Sci USA.* 104: 3568-3573, 2007). This process results in exocytotic insertion of pro-apoptotic Kv2.1 channels into the plasma membrane, likely at specialized Kv2.1 cluster domains that form ER-PM junctions (Johnson et al., *Proc Natl Acad Sci USA.* 115: E7331-E7340, 2018; Johnson, et al., *Channels (Austin).* 13: 88-101, 2019), and act as scaffolding sites for up to 85% of Kv2.1 channels that are trafficked to the membrane (Deutsch et al., *Mol Biol Cell.* 23: 2917-2929, 2012). Importantly, this population of pro-apoptotic Kv2.1 is distinct from the existing, freely dispersed population of physiologically active Kv2.1 that regulates neuronal excitability and neuronal firing rates in normal brain tissue, as these channels are de novo inserted in a delayed manner in response to injury (Pal, et al., *J Neurosci.* 23: 4798-4802, 2003; Pal, et al., *Cell Death Differ.* 13: 661-667, 2006; McCord et al., *J Physiol (Lond).* 592: 3511-3521, 2014; McLaughlin et al., *J Neurosci.* 21, 3303-3311, 2001; McCord, et al., *Proc Natl Acad Sci USA.* 110: 13988-13993, 2013; Redman, et al., *J Physiol (Lond).* 587: 4393-4404, 2009; Redman et al., *Proc Natl Acad Sci USA.* 104: 3568-3573, 2007). As such, this mechanism provides an attractive neuroprotective target whereby only injury-induced, pro-apoptotic Kv2.1 channel insertion is selectively blocked, while physiologically active channels remain unaffected. Thus, this strategy theoretically eliminates adverse effects on normal neuronal excitability seen with wide-spectrum potassium channel blockade in the context of neuroprotection.

Kv2.1 cluster biology is extremely complex and various other possible roles of Kv2.1 cluster dispersal in response to brain injury are likely. Indeed, there are data that suggest Kv2.1 clusters are juxtaposed to astrocyte processes expressing high levels of energy-dependent glutamate transporters (Misonou, et al., *J Neurosci.* 28: 8529-8538, 2008). Thus, metabolic impairment of astrocytes yields transporter failure and glutamate accumulation at these synapses, yielding transient Kv2.1 cluster dispersal, which potentially acts as a preemptive response to pending injury by an accompanying decrease in neuronal excitability (Misonou, et al., *J Neurosci.* 28: 8529-8538, 2008: Misonou et al., *Nat Neurosci.* 7: 711-718, 2004). However, while pro-apoptotic Kv2.1 channel insertion can be delayed by this innate response, physiologic Kv2.1 cluster dispersal is often transient and may recover in as little as two hours following stimuli removal (Misonou et al., *Nat Neurosci.* 7: 711-718, 2004). The disclosed treatment strategy may in fact enable prolongation of this preemptive neuroprotective response by TAT-DP-2-mediated declustering. Furthermore, recent evidence indicates that microglia also form somatic membrane contacts with cortical neurons at Kv2.1 cluster sites (Cserép et al., *Science.* 367: 528-537, 2020). Following stroke in mice, the area of these junctions increases significantly, accompanied by endogenous Kv2.1 channel cluster dispersal. Interestingly, inhibition of the P2Y12 receptor—thought to mediate these microglial-somatic contacts—following stroke leads to an increase in infarct damage. Thus, this study further implicates the Kv2.1 cluster domain as a critical player in the neuronal response to ischemic insult.

Previous preclinical studies have shown efficacious neuroprotection in vivo by targeting the Kv2.1-syntaxin interaction (FIG. 13B), which is the final step in pro-apoptotic Kv2.1 membrane insertion (Yeh et al., *J Neurosci.* 37: 5648-5658, 2017; Yeh et al., *Proc Natl Acad Sci USA.* 116: 15696-15607, 2019). The results in the present study target this process via a completely novel approach, namely, the elimination of the putative insertion sites for cell death trafficking of channels, the Kv2.1 membrane cluster domains. Given that this study reports a second, separate mechanism of effective Kv2.1-specific, targeted neuroprotection following ischemic injury, it is likely that further translational development of these strategies—or even their synergistic use—will lead to the development of a novel class of delayed, penumbral neuro-protectant drugs. Furthermore, as a multitude of neurodegenerative disorders may rely on apoptotic cell death for progression (Friedlander et al., *N Engl J Med.* 348: 1365-1375, 2003; Mattson et al., *Nat Rev Mol Cell Biol.* 1: 120-129, 2000), this strategy targets a highly-conserved mechanism with a novel approach that may even provide a generalizable class of anti-apoptotic drugs for disorders including Alzheimer's Disease and Parkinson's Disease.

Although proximity ligation assays clearly show that TAT-DP-2 treatment reduces the interaction between Kv2.1 and VAPA, a peptide spot array assay suggests that the active peptide fragment from DP-2 (SIDSFTS; SEQ ID NO: 1) does not bind to VAPA proteins directly, even when mutated into its pseudo-phosphorylated form. Furthermore, isolated non-canonical FFAT motifs found on both Kv2.1 and Kv2.2 also yielded no binding to VAPA proteins in peptide spot array studies, although recent work suggests this interaction may be critical for Kv2.1 cluster formation. In fact, mutation of the FFAT binding domain on VAPA abolishes the ability for Kv2.1 channels to form clusters in HEK cells in vitro (Kirmiz et al., *J Neurosci.* 38: 7562-7584, 2018; Johnson et al., *Proc Natl Acad Sci USA.* 115: E7331-E7340, 2018). One possible explanation for this inconsistency is simply that peptide spot array studies do not accurately allow for tertiary or quaternary protein structure formation that is required for interaction and binding. Further, a larger fragment of the C-terminal domain of Kv2.1 or Kv2.2 may be required for total VAPA binding and TAT-DP-2 might simply be outcompeting existing Kv2.1 channels by blocking a smaller portion of the FFAT binding domain located on VAPA proteins. It is also plausible that the actions of TAT-DP-2 require Kv2.1-VAPA association in the cellular cluster microdomain, while acellular experiments like the peptide spot array do not provide a sufficiently realistic spatial and electrostatic articulation between key proteins. Another possibility is that TAT-DP-2 may have a target sequence within Kv2.1 itself, and that, upon binding, does not allow the channel to bind VAPA via an allosteric mechanism. Understanding this biophysical association may prove invaluable for further development of additional neuroprotective peptides and small molecules that displace this interaction, as well as for optimization of the strategy described herein. However, the lack of Kv2.1 cluster dispersal following treatment with a TAT-linked canonical FFAT motif (FIGS. 11B and 11C) suggests that DP-2's declustering-inducing disruption of Kv2.1-VAPA association might occur via a unique mechanism, and thus could lack significant off-target actions on the broad array of VAP-binding proteins.

The steps required to translate these findings to clinical practice have a strong existing precedent as TAT-linked neuroprotective peptides targeting N-methyl-D-aspartate receptor-mediated production of nitric oxide have shown efficacy in phase II and III clinical trials (Hill et al., *The Lancet*. 395: 878-887, 2020; Hill et al., *Lancet Neurol*. 11: 942-950, 2012). With new data that enables the use of endovascular thrombectomy and reperfusion at late timepoints following stroke (Nogueira et al., *N Engl J Med*. 378: 708-718, 2018; Albers et al., *N Engl J Med*. 378: 708-718, 2018), the clinical utility of neuroprotective agents is increasing significantly.

In summary, it is demonstrated that targeted dispersal of Kv2.1 channel clusters both reduce infarct area and preserve neurological function following ischemic stroke in mice. Further, the mechanism of this neuroprotective effect is defined and proof-of-concept is provided for an injectable neuroprotective therapeutic. Utilizing a TAT-linked peptide based on the region of Kv2.2 CT that induces Kv2.1 cluster dispersal, Kv2.1 cluster dispersal and neuroprotection was demonstrated in vitro and in vivo. Importantly, improved neurological function in peptide-treated animals was observed for up to six weeks following an induced cerebral infarct. The disclosed data also present strong mechanistic evidence that disruption of Kv2.1-VAPA interaction by the tested peptide can account for the neuroprotective blockade of pro-apoptotic Kv2.1 potassium currents following injury (FIGS. 13A-13D). The results described herein strongly cement the notion that targeting Kv2.1-facilitated cell death is likely to yield effective, innovative, neuroprotective therapeutic drugs for patients suffering from ischemic stroke, and in future studies, many other neurodegenerative disorders where this channel has been implicated (Aizenman et al., *Front Aging Neurosci*. 6: 77, 2014; Wei et al., *Cell Death Dis*. 9: 820, 2018; Yu et al., *J Neurosci*. 36: 11084-11096, 2016).

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. An isolated or recombinant neuroprotective peptide, wherein the amino acid sequence of the peptide comprises:
   SEQ ID NO: 1, wherein the serine at position 1, 4 and/or 7 is replaced with aspartic acid;
   SEQ ID NO: 1, wherein the serine at position 1, 4 and/or 7 is replaced with glutamic acid; or
   SEQ ID NO: 1, wherein the serine at position 1, 4 and/or 7 is phosphorylated,
   wherein the peptide is no more than 20 amino acids in length.

2. The isolated or recombinant neuroprotective peptide of claim 1, wherein the peptide is no more than 15 amino acids in length.

3. The isolated or recombinant neuroprotective peptide of claim 1, wherein the peptide is no more than 10 amino acids in length.

4. The isolated or recombinant neuroprotective peptide of claim 1, wherein the amino acid sequence of the peptide comprises any one of SEQ ID NOs: 2-22.

5. The isolated or recombinant neuroprotective peptide of claim 1, wherein the amino acid sequence of the peptide consists of any one of SEQ ID NOs: 2-22.

6. A composition, comprising a pharmaceutically acceptable carrier and the neuroprotective peptide of claim 1.

7. An isolated nucleic acid molecule encoding the isolated or recombinant neuroprotective peptide of claim 1.

8. The isolated nucleic acid molecule of claim 7, operably linked to a heterologous promoter.

9. A vector comprising the isolated nucleic acid molecule of claim 7.

10. An isolated host cell comprising the nucleic acid molecule of claim 7.

11. A method of declustering delayed-rectifying voltage-gated potassium channel Kv2.1 in a cell, comprising contacting the cell with the isolated or recombinant neuroprotective peptide of claim 1 or SEQ ID NO: 1.

12. The method of claim 11, wherein the cell is a neuron.

13. A method of treating or inhibiting neuronal damage in a subject, comprising administering to the subject a therapeutically effective amount of the isolated or recombinant neuroprotective peptide of claim 1 or SEQ ID NO: 1, thereby treating or inhibiting neuronal damage in the subject.

14. The method of claim 13, wherein the subject is suffering from or has suffered from cerebral ischemia, stroke, traumatic brain injury, a neurodegenerative disease, cardiac arrest, or epilepsy.

15. The method of claim 13, comprising administering the peptide by intraperitoneal injection.

16. A method of treating ischemic stroke in a subject, comprising administering to the subject a therapeutically effective amount of the isolated or recombinant neuroprotective peptide of claim 1 or SEQ ID NO: 1, thereby treating ischemic stroke in the subject.

17. The method of claim 16, comprising administering the peptide by intraperitoneal injection.

18. A fusion protein, comprising a cell-penetrating peptide (CPP) and a neuroprotective peptide, wherein the amino acid sequence of the neuroprotective peptide comprises:
   SEQ ID NO: 1;
   SEQ ID NO: 1, wherein the serine at position 1, 4 and/or 7 is replaced with aspartic acid;
   SEQ ID NO: 1, wherein the serine at position 1, 4 and/or 7 is replaced with glutamic acid; or
   SEQ ID NO: 1, wherein the serine at position 1, 4 and/or 7 is phosphorylated,
   wherein the neuroprotective peptide is no more than 20 amino acids in length.

19. The fusion protein of claim 6, wherein the CPP comprises a transactivator of transcription (TAT) peptide comprising the amino acid sequence of SEQ ID NO: 31.

20. The fusion protein of claim 6, wherein the amino acid sequence of the fusion protein comprises or consists of SEQ ID NO: 23, SEQ ID NO: 25 or SEQ ID NO: 26.

* * * * *

SEQUENCE LISTING

```
<160> NUMBER OF SEQ ID NOS: 101

<210> SEQ ID NO 1
<211> LENGTH: 7
<212> TYPE: PRT
<213> ORGANISM: Artificial Sequence
<220> FEATURE:
<223> OTHER INFORMATION: synthetic amino acid

<400> SEQUENCE: 1

Ser Ile Asp Ser Phe Thr Ser
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic amino acid

<400> SEQUENCE: 2

Asp Ile Asp Ser Phe Thr Ser
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic amino acid

<400> SEQUENCE: 3

Ser Ile Asp Asp Phe Thr Ser
1               5

<210> SEQ ID NO 4
<211> LENGTH: 7
<212> TYPE: PRT
<213> ORGANISM: Artificial Sequence
<220> FEATURE:
```

```
<223> OTHER INFORMATION: synthetic amino acid

<400> SEQUENCE: 4

Ser Ile Asp Ser Phe Thr Asp
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic amino acid

<400> SEQUENCE: 5

Asp Ile Asp Asp Phe Thr Ser
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic amino acid

<400> SEQUENCE: 6

Ser Ile Asp Asp Phe Thr Asp
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic amino acid

<400> SEQUENCE: 7

Asp Ile Asp Ser Phe Thr Asp
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic amino acid

<400> SEQUENCE: 8

Asp Ile Asp Asp Phe Thr Asp
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic amino acid

<400> SEQUENCE: 9

Glu Ile Asp Ser Phe Thr Ser
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic amino acid
```

```
<400> SEQUENCE: 10

Ser Ile Asp Glu Phe Thr Ser
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic amino acid

<400> SEQUENCE: 11

Ser Ile Asp Ser Phe Thr Glu
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic amino acid

<400> SEQUENCE: 12

Glu Ile Asp Glu Phe Thr Ser
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic amino acid

<400> SEQUENCE: 13

Ser Ile Asp Glu Phe Thr Glu
1               5

<210> SEQ ID NO 14
<211> LENGTH: 7
<212> TYPE: PRT
<213> ORGANISM: Artificial Sequence
<220> FEATURE:
<223> OTHER INFORMATION: synthetic amino acid

<400> SEQUENCE: 14

Glu Ile Asp Ser Phe Thr Glu
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic amino acid

<400> SEQUENCE: 15

Glu Ile Asp Glu Phe Thr Glu
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic amino acid
<220> FEATURE:
```

```
<221> NAME/KEY: MISC_FEATURE
<222> LOCATION: (1)..(1)
<223> OTHER INFORMATION: phosphorylated serine

<400> SEQUENCE: 16

Ser Ile Asp Ser Phe Thr Ser
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (4)..(4)
<223> OTHER INFORMATION: phosphorylated serine

<400> SEQUENCE: 17

Ser Ile Asp Ser Phe Thr Ser
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (7)..(7)
<223> OTHER INFORMATION: phosphorylated serine

<400> SEQUENCE: 18

Ser Ile Asp Ser Phe Thr Ser
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 19

Ser Ile Asp Ser Phe Thr Ser
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (4)..(4)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine
```

```
<400> SEQUENCE: 20

Ser Ile Asp Ser Phe Thr Ser
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 21

Ser Ile Asp Ser Phe Thr Ser
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 22

Ser Ile Asp Ser Phe Thr Ser
1               5

<210> SEQ ID NO 23
<211> LENGTH: 18
<212> TYPE: PRT
<213> ORGANISM: Artificial Sequence
<220> FEATURE:
<223> OTHER INFORMATION: synthetic amino acid

<400> SEQUENCE: 23

Tyr Gly Arg Lys Lys Arg Arg Gln Arg Arg Ser Ile Asp Ser Phe
1               5                   10                  15

Thr Ser

<210> SEQ ID NO 24
<211> LENGTH: 18
<212> TYPE: PRT
<213> ORGANISM: Artificial Sequence
<220> FEATURE:
<223> OTHER INFORMATION: synthetic amino acid

<400> SEQUENCE: 24

Tyr Gly Arg Lys Lys Arg Arg Gln Arg Arg Asp Phe Ser Ser Ile
1               5                   10                  15
```

Ser Thr

<210> SEQ ID NO 25
<211> LENGTH: 18
<212> TYPE: PRT
<213> ORGANISM: Artificial Sequence
<220> FEATURE:
<223> OTHER INFORMATION: synthetic amino acid

<400> SEQUENCE: 25

Tyr Gly Arg Lys Lys Arg Arg Gln Arg Arg Arg Ala Ile Asp Ala Phe
1               5                   10                  15

Thr Ala

<210> SEQ ID NO 26
<211> LENGTH: 18
<212> TYPE: PRT
<213> ORGANISM: Artificial Sequence
<220> FEATURE:
<223> OTHER INFORMATION: synthetic amino acid

<400> SEQUENCE: 26

Tyr Gly Arg Lys Lys Arg Arg Gln Arg Arg Arg Asp Ile Asp Asp Phe
1               5                   10                  15

Thr Asp

<210> SEQ ID NO 27
<211> LENGTH: 12
<212> TYPE: PRT
<213> ORGANISM: Artificial Sequence
<220> FEATURE:
<223> OTHER INFORMATION: synthetic amino acid

<400> SEQUENCE: 27

Met Lys Ser Thr Ser Ser Ile Asp Ser Phe Thr Ser
1               5                   10

<210> SEQ ID NO 28
<211> LENGTH: 12
<212> TYPE: PRT
<213> ORGANISM: Artificial Sequence
<220> FEATURE:
<223> OTHER INFORMATION: synthetic amino acid

<400> SEQUENCE: 28

Met Lys Ser Thr Ser Asp Phe Ser Ser Ile Ser Thr
1               5                   10

<210> SEQ ID NO 29
<211> LENGTH: 26
<212> TYPE: PRT
<213> ORGANISM: Artificial Sequence
<220> FEATURE:
<223> OTHER INFORMATION: synthetic amino acid

<400> SEQUENCE: 29

Glu Val Ile Val Asp Met Lys Ser Thr Ser Ser Ile Asp Ser Phe Thr
1               5                   10                  15

Ser Cys Ala Thr Asp Phe Thr Glu Thr Glu
            20                  25

<210> SEQ ID NO 30
<211> LENGTH: 26
<212> TYPE: PRT

```
<213> ORGANISM: Artificial Sequence
<220> FEATURE:
<223> OTHER INFORMATION: synthetic amino acid

<400> SEQUENCE: 30

Glu Gly Val Ile Asp Met Arg Ser Met Ser Ser Ile Asp Ser Phe Ile
1               5                   10                  15

Ser Cys Ala Thr Asp Phe Pro Glu Ala Thr
            20                  25

<210> SEQ ID NO 31
<211> LENGTH: 11
<212> TYPE: PRT
<213> ORGANISM: Artificial Sequence
<220> FEATURE:
<223> OTHER INFORMATION: synthetic amino acid

<400> SEQUENCE: 31

Tyr Gly Arg Lys Lys Arg Arg Gln Arg Arg
1               5                   10

<210> SEQ ID NO 32
<211> LENGTH: 857
<212> TYPE: PRT
<213> ORGANISM: Rattus norvegicus

<400> SEQUENCE: 32

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
        35                  40                  45

Leu Asp Arg Leu Pro Arg Thr Arg Leu Gly Lys Leu Arg Asp Cys Asn
    50                  55                  60

Thr His Asp Ser Leu Leu Gln Val Cys Asp Asp Tyr Ser Leu Glu Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
            100                 105                 110

Leu Ser Phe Ser Gln Glu Leu Asp Tyr Trp Gly Ile Asp Glu Ile Tyr
        115                 120                 125

Leu Glu Ser Cys Cys Gln Ala Arg Tyr His Gln Lys Lys Glu Gln Met
    130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Ala Lys Ile Leu Ala
            180                 185                 190

Ile Ile Ser Ile Met Phe Ile Val Leu Ser Thr Ile Ala Leu Ser Leu
        195                 200                 205

Asn Thr Leu Pro Glu Leu Gln Ser Leu Asp Glu Phe Gly Gln Ser Thr
    210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
```

```
                245                 250                 255
Phe Phe Lys Gly Pro Leu Asn Ala Ile Asp Leu Leu Ala Ile Leu Pro
            260                 265                 270
Tyr Tyr Val Thr Ile Phe Leu Thr Glu Ser Asn Lys Ser Val Leu Gln
            275                 280                 285
Phe Gln Asn Val Arg Arg Val Gln Ile Phe Arg Ile Met Arg Ile
    290                 295                 300
Leu Arg Ile Leu Lys Leu Ala Arg His Ser Thr Gly Leu Gln Ser Leu
305                 310                 315                 320
Gly Phe Thr Leu Arg Arg Ser Tyr Asn Glu Leu Gly Leu Leu Ile Leu
                325                 330                 335
Phe Leu Ala Met Gly Ile Met Ile Phe Ser Ser Leu Val Phe Phe Ala
                340                 345                 350
Glu Lys Asp Glu Asp Asp Thr Lys Phe Lys Ser Ile Pro Ala Ser Phe
                355                 360                 365
Trp Trp Ala Thr Ile Thr Met Thr Thr Val Gly Tyr Gly Asp Ile Tyr
    370                 375                 380
Pro Lys Thr Leu Leu Gly Lys Ile Val Gly Gly Leu Cys Cys Ile Ala
385                 390                 395                 400
Gly Val Leu Val Ile Ala Leu Pro Ile Pro Ile Val Asn Asn Phe
                    405                 410                 415
Ser Glu Phe Tyr Lys Glu Gln Lys Arg Gln Glu Lys Ala Ile Lys Arg
                420                 425                 430
Arg Glu Ala Leu Glu Arg Ala Lys Arg Asn Gly Ser Ile Val Ser Met
                435                 440                 445
Asn Met Lys Asp Ala Phe Ala Arg Ser Ile Glu Met Met Asp Ile Val
            450                 455                 460
Val Glu Lys Asn Gly Glu Ser Ile Ala Lys Lys Asp Lys Val Gln Asp
465                 470                 475                 480
Asn His Leu Ser Pro Asn Lys Trp Lys Trp Thr Lys Arg Ala Leu Ser
                    485                 490                 495
Glu Thr Ser Ser Ser Lys Ser Phe Glu Thr Lys Glu Gln Gly Ser Pro
                500                 505                 510
Glu Lys Ala Arg Ser Ser Ser Pro Gln His Leu Asn Val Gln Gln
            515                 520                 525
Leu Glu Asp Met Tyr Ser Lys Met Ala Lys Thr Gln Ser Gln Pro Ile
            530                 535                 540
Leu Asn Thr Lys Glu Met Ala Pro Gln Ser Lys Pro Pro Glu Glu Leu
545                 550                 555                 560
Glu Met Ser Ser Met Pro Ser Pro Val Ala Pro Leu Pro Ala Arg Thr
                565                 570                 575
Glu Gly Val Ile Asp Met Arg Ser Met Ser Ser Ile Asp Ser Phe Ile
                580                 585                 590
Ser Cys Ala Thr Asp Phe Pro Glu Ala Thr Arg Phe Ser His Ser Pro
                595                 600                 605
Leu Ala Ser Leu Ser Ser Lys Ala Gly Ser Ser Thr Ala Pro Glu Val
                610                 615                 620
Gly Trp Arg Gly Ala Leu Gly Ala Ser Gly Gly Arg Leu Thr Glu Thr
625                 630                 635                 640
Asn Pro Ile Pro Glu Thr Ser Arg Ser Gly Phe Phe Val Glu Ser Pro
                    645                 650                 655
Arg Ser Ser Met Lys Thr Asn Asn Pro Leu Lys Leu Arg Ala Leu Lys
                660                 665                 670
```

-continued

```
Val Asn Phe Val Glu Gly Asp Pro Thr Pro Leu Leu Pro Ser Leu Gly
            675                 680                 685

Leu Tyr His Asp Pro Leu Arg Asn Arg Gly Gly Ala Ala Ala Ala Val
        690                 695                 700

Ala Gly Leu Glu Cys Ala Ser Leu Leu Asp Lys Pro Val Leu Ser Pro
705                 710                 715                 720

Glu Ser Ser Ile Tyr Thr Thr Ala Ser Ala Arg Thr Pro Arg Ser
                725                 730                 735

Pro Glu Lys His Thr Ala Ile Ala Phe Asn Phe Glu Ala Gly Val His
            740                 745                 750

His Tyr Ile Asp Thr Asp Thr Asp Asp Glu Gly Gln Leu Leu Tyr Ser
        755                 760                 765

Val Asp Ser Ser Pro Pro Lys Ser Leu His Gly Ser Thr Ser Pro Lys
770                 775                 780

Phe Ser Thr Gly Ala Arg Thr Glu Lys Asn His Phe Glu Ser Ser Pro
785                 790                 795                 800

Leu Pro Thr Ser Pro Lys Phe Leu Arg Pro Asn Cys Val Tyr Ser Ser
                805                 810                 815

Glu Gly Leu Thr Gly Lys Gly Pro Gly Ala Gln Glu Lys Cys Lys Leu
            820                 825                 830

Glu Asn His Thr Pro Pro Asp Val His Met Leu Pro Gly Gly Gly Ala
        835                 840                 845

His Gly Ser Thr Arg Asp Gln Ser Ile
    850                 855
```

```
<210> SEQ ID NO 33
<211> LENGTH: 7
<212> TYPE: PRT
<213> ORGANISM: Artificial Sequence
<220> FEATURE:
<223> OTHER INFORMATION: synthetic amino acid

<400> SEQUENCE: 33

Ser Phe Ile Ser Cys Ala Thr
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic amino acid

<400> SEQUENCE: 34

Ser Phe Thr Ser Cys Ala Thr
1               5

<210> SEQ ID NO 35
<211> LENGTH: 7
<212> TYPE: PRT
<213> ORGANISM: Artificial Sequence
<220> FEATURE:
<223> OTHER INFORMATION: synthetic amino acid

<400> SEQUENCE: 35

Asp Phe Ser Ser Ile Ser Thr
1               5

<210> SEQ ID NO 36
<211> LENGTH: 7
```

```
<212> TYPE: PRT
<213> ORGANISM: Artificial Sequence
<220> FEATURE:
<223> OTHER INFORMATION: synthetic amino acid

<400> SEQUENCE: 36

Glu Phe Phe Asp Ala Pro Glu
1               5

<210> SEQ ID NO 37
<211> LENGTH: 18
<212> TYPE: PRT
<213> ORGANISM: Artificial Sequence
<220> FEATURE:
<223> OTHER INFORMATION: synthetic amino acid

<400> SEQUENCE: 37

Tyr Gly Arg Lys Lys Arg Arg Gln Arg Arg Glu Phe Phe Asp Ala
1               5                   10                  15

Pro Glu

<210> SEQ ID NO 38
<211> LENGTH: 17
<212> TYPE: PRT
<213> ORGANISM: Artificial Sequence
<220> FEATURE:
<223> OTHER INFORMATION: synthetic amino acid

<400> SEQUENCE: 38

Tyr Gly Arg Lys Lys Arg Arg Gln Arg Arg Asp Glu Glu Phe Ala
1               5                   10                  15

Pro

<210> SEQ ID NO 39
<211> LENGTH: 857
<212> TYPE: PRT
<213> ORGANISM: Mus musculus

<400> SEQUENCE: 39

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
                20                  25                  30

Val Arg Leu Asn Val Gly Gly Leu Ala His Glu Val Leu Trp Arg Thr
            35                  40                  45

Leu Asp Arg Leu Pro Arg Thr Arg Leu Gly Lys Leu Arg Asp Cys Asn
        50                  55                  60

Thr His Asp Ser Leu Leu Gln Val Cys Asp Asp Tyr Ser Leu Glu Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
                100                 105                 110

Leu Ser Phe Ser Gln Glu Leu Asp Tyr Trp Gly Ile Asp Glu Ile Tyr
            115                 120                 125

Leu Glu Ser Cys Cys Gln Ala Arg Tyr His Gln Lys Lys Glu Gln Met
        130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
```

```
                 165                 170                 175
Asp Leu Leu Glu Lys Pro Asn Ser Ser Val Ala Ala Lys Ile Leu Ala
             180                 185                 190

Ile Ile Ser Ile Met Phe Ile Val Leu Ser Thr Ile Ala Leu Ser Leu
         195                 200                 205

Asn Thr Leu Pro Glu Leu Gln Ser Leu Asp Glu Phe Gly Gln Ser Thr
     210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
            260                 265                 270

Tyr Tyr Val Thr Ile Phe Leu Thr Glu Ser Asn Lys Ser Val Leu Gln
        275                 280                 285

Phe Gln Asn Val Arg Arg Val Val Gln Ile Phe Arg Ile Met Arg Ile
    290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

Phe Leu Ala Met Gly Ile Met Ile Phe Ser Ser Leu Val Phe Phe Ala
            340                 345                 350

Glu Lys Asp Glu Asp Thr Lys Phe Lys Ser Ile Pro Ala Ser Phe
        355                 360                 365

Trp Trp Ala Thr Ile Thr Met Thr Thr Val Gly Tyr Gly Asp Ile Tyr
    370                 375                 380

Pro Lys Thr Leu Leu Gly Lys Ile Val Gly Gly Leu Cys Cys Ile Ala
385                 390                 395                 400

Gly Val Leu Val Ile Ala Leu Pro Ile Pro Ile Ile Val Asn Asn Phe
                405                 410                 415

Ser Glu Phe Tyr Lys Glu Gln Lys Arg Gln Glu Lys Ala Ile Lys Arg
            420                 425                 430

Arg Glu Ala Leu Glu Arg Ala Lys Arg Asn Gly Ser Ile Val Ser Met
        435                 440                 445

Asn Met Lys Asp Ala Phe Ala Arg Ser Ile Glu Met Met Asp Ile Val
    450                 455                 460

Val Glu Lys Asn Gly Glu Gly Val Ala Lys Lys Asp Lys Val Gln Asp
465                 470                 475                 480

Asn His Leu Ser Pro Asn Lys Trp Lys Trp Thr Lys Arg Ala Leu Ser
                485                 490                 495

Glu Thr Ser Ser Ser Lys Ser Phe Glu Thr Lys Glu Gln Gly Ser Pro
            500                 505                 510

Glu Lys Ala Arg Ser Ser Ser Pro Gln His Leu Asn Val Gln Gln
        515                 520                 525

Leu Gln Asp Met Tyr Ser Lys Met Ala Lys Thr Gln Ser Gln Pro Ile
    530                 535                 540

Leu Asn Thr Lys Glu Met Ala Pro Gln Ser Gln Pro Gln Glu Glu Leu
545                 550                 555                 560

Glu Met Gly Ser Met Pro Ser Pro Val Ala Pro Leu Pro Thr Arg Thr
                565                 570                 575

Glu Gly Val Ile Asp Met Arg Ser Met Ser Ser Ile Asp Ser Phe Ile
            580                 585                 590
```

Ser Cys Ala Thr Asp Phe Pro Glu Ala Thr Arg Phe Ser His Ser Pro
        595                 600                 605

Leu Ala Ser Leu Ser Gly Lys Ser Gly Gly Ser Thr Ala Pro Glu Val
            610                 615                 620

Gly Trp Arg Gly Ala Leu Gly Ala Ser Gly Gly Arg Leu Met Glu Thr
625                 630                 635                 640

Asn Pro Ile Pro Glu Ala Ser Arg Ser Gly Phe Phe Val Glu Ser Pro
                645                 650                 655

Arg Ser Ser Met Lys Thr His Asn Pro Met Lys Leu Arg Ala Leu Lys
        660                 665                 670

Val Asn Phe Leu Glu Gly Asp Pro Thr Pro Leu Leu Pro Ala Leu Gly
            675                 680                 685

Leu Tyr His Asp Pro Leu Arg Asn Arg Gly Gly Ala Ala Ala Ala Val
        690                 695                 700

Ala Gly Leu Glu Cys Ala Ser Leu Leu Asp Lys Pro Val Leu Ser Pro
705                 710                 715                 720

Glu Ser Ser Ile Tyr Thr Thr Ala Ser Ala Arg Thr Pro Pro Arg Ser
                725                 730                 735

Pro Glu Lys His Thr Ala Ile Ala Phe Asn Phe Glu Ala Gly Val His
            740                 745                 750

Gln Tyr Ile Asp Thr Asp Thr Asp Asp Glu Gly Gln Leu Leu Tyr Ser
        755                 760                 765

Val Asp Ser Ser Pro Pro Lys Ser Leu His Gly Ser Thr Ser Pro Lys
        770                 775                 780

Phe Ser Leu Gly Ala Arg Thr Glu Lys Asn His Phe Glu Ser Ser Pro
785                 790                 795                 800

Leu Pro Thr Ser Pro Lys Phe Leu Arg Pro Asn Cys Val Tyr Ala Ser
                805                 810                 815

Glu Gly Leu Pro Gly Lys Gly Pro Gly Ala Gln Glu Lys Cys Lys Leu
            820                 825                 830

Glu Asn His Thr Ser Pro Asp Val His Met Leu Pro Gly Gly Gly Ala
        835                 840                 845

His Gly Ser Thr Arg Asp Gln Ser Ile
        850                 855

<210> SEQ ID NO 40
<211> LENGTH: 907
<212> TYPE: PRT
<213> ORGANISM: Mus musculus

<400> SEQUENCE: 40

Met Ala Glu Lys Ala Pro Pro Gly Leu Asn Arg Lys Thr Ser Arg Ser
1               5                   10                  15

Thr Leu Ser Leu Pro Pro Glu Pro Val Asp Ile Ile Arg Ser Lys Thr
            20                  25                  30

Cys Ser Arg Arg Val Lys Ile Asn Val Gly Gly Leu Asn His Glu Val
        35                  40                  45

Leu Trp Arg Thr Leu Asp Arg Leu Pro Arg Thr Arg Leu Gly Lys Leu
    50                  55                  60

Arg Asp Cys Asn Thr His Glu Ser Leu Leu Glu Val Cys Asp Asp Tyr
65                  70                  75                  80

Asn Leu Asn Glu Asn Glu Tyr Phe Phe Asp Arg His Pro Gly Ala Phe
                85                  90                  95

Thr Ser Ile Leu Asn Phe Tyr Arg Thr Gly Lys Leu His Met Met Glu

-continued

```
                100                 105                 110
    Glu Met Cys Ala Leu Ser Phe Gly Gln Glu Leu Asp Tyr Trp Gly Ile
                115                 120                 125
    Asp Glu Ile Tyr Leu Glu Ser Cys Cys Gln Ala Arg Tyr His Gln Lys
    130                 135                 140
    Lys Glu Gln Met Asn Glu Leu Arg Arg Glu Ala Glu Thr Met Arg
    145                 150                 155                 160
    Glu Arg Glu Gly Glu Glu Phe Asp Asn Thr Cys Cys Pro Glu Lys Arg
                165                 170                 175
    Lys Lys Leu Trp Asp Leu Leu Glu Lys Pro Asn Ser Ser Val Ala Ala
                180                 185                 190
    Lys Ile Leu Ala Ile Val Ser Ile Leu Phe Ile Val Leu Ser Thr Ile
                195                 200                 205
    Ala Leu Ser Leu Asn Thr Leu Pro Glu Leu Gln Glu Asn Asp Glu Phe
    210                 215                 220
    Gly Gln Pro Ser Asp Asn Arg Lys Leu Ala His Val Glu Ala Val Cys
    225                 230                 235                 240
    Ile Ala Trp Phe Thr Met Glu Tyr Leu Leu Arg Phe Leu Ser Ser Pro
                245                 250                 255
    Asn Lys Trp Lys Phe Phe Lys Gly Pro Leu Asn Val Ile Asp Leu Leu
                260                 265                 270
    Ala Ile Leu Pro Tyr Tyr Val Thr Ile Phe Leu Thr Glu Ser Asn Lys
                275                 280                 285
    Ser Val Leu Gln Phe Gln Asn Val Arg Arg Val Val Gln Ile Phe Arg
                290                 295                 300
    Ile Met Arg Ile Leu Arg Ile Leu Lys Leu Ala Arg His Ser Thr Gly
    305                 310                 315                 320
    Leu Gln Ser Leu Gly Phe Thr Leu Arg Arg Ser Tyr Asn Glu Leu Gly
                325                 330                 335
    Leu Leu Ile Leu Phe Leu Ala Met Gly Ile Met Ile Phe Ser Ser Leu
                340                 345                 350
    Val Phe Phe Ala Glu Lys Asp Glu Asp Ala Thr Lys Phe Thr Ser Ile
                355                 360                 365
    Pro Ala Ser Phe Trp Trp Ala Thr Ile Thr Met Thr Thr Val Gly Tyr
    370                 375                 380
    Gly Asp Ile Tyr Pro Lys Thr Leu Leu Gly Lys Ile Val Gly Gly Leu
    385                 390                 395                 400
    Cys Cys Ile Ala Gly Val Leu Val Ile Ala Leu Pro Ile Pro Ile Ile
                405                 410                 415
    Val Asn Asn Phe Ser Glu Phe Tyr Lys Glu Gln Lys Arg Gln Glu Lys
                420                 425                 430
    Ala Ile Lys Arg Arg Glu Ala Leu Glu Arg Ala Lys Arg Asn Gly Ser
                435                 440                 445
    Ile Val Ser Met Asn Leu Lys Asp Ala Phe Ala Arg Ser Met Glu Leu
                450                 455                 460
    Ile Asp Val Ala Val Glu Lys Ala Gly Glu Ser Ala Asn Thr Lys Asp
    465                 470                 475                 480
    Ser Val Asp Asp Asn His Leu Ser Pro Ser Arg Trp Lys Trp Ala Arg
                485                 490                 495
    Lys Ala Leu Ser Glu Thr Ser Ser Asn Lys Ser Tyr Glu Asn Lys Tyr
                500                 505                 510
    Gln Glu Val Ser Gln Asn Asp Ser His Glu His Leu Asn Asn Thr Ser
                515                 520                 525
```

Ser Ser Ser Pro Gln His Leu Ser Ala Gln Lys Leu Glu Met Leu Tyr
            530                 535                 540

Asn Glu Ile Thr Lys Thr Gln Pro His Ser His Pro Asn Pro Asp Cys
545                 550                 555                 560

Gln Glu Gln Pro Glu Arg Pro Cys Val Tyr Glu Glu Glu Ile Glu Met
                565                 570                 575

Glu Glu Val Ile Cys Pro Gln Glu Gln Leu Ala Val Ala Gln Thr Glu
            580                 585                 590

Val Ile Val Asp Met Lys Ser Thr Ser Ser Ile Asp Ser Phe Thr Ser
            595                 600                 605

Cys Ala Thr Asp Phe Thr Glu Thr Glu Arg Ser Pro Leu Pro Pro Pro
610                 615                 620

Ser Ala Ser His Leu Gln Met Lys Phe Pro Thr Asp Leu Pro Gly Thr
625                 630                 635                 640

Asp Glu His Gln Arg Ala Arg Ala Pro Pro Phe Leu Thr Leu Ser Arg
                645                 650                 655

Asp Lys Gly Pro Ala Ala Arg Glu Ala Ala Val Asp Tyr Ala Pro Ile
                660                 665                 670

Asp Ile Thr Val Asn Leu Asp Ala Gly Ala Ser His Gly Pro Leu Gln
            675                 680                 685

Pro Asp Ser Ala Ser Asp Ser Pro Lys Ser Ser Leu Lys Gly Ser Asn
690                 695                 700

Pro Leu Lys Ser Arg Ser Leu Lys Val Asn Phe Gln Glu Asn Arg Ala
705                 710                 715                 720

Ser Ala Pro Gln Thr Pro Pro Ser Thr Ala Arg Pro Leu Pro Val Thr
                725                 730                 735

Thr Ala Asp Phe Pro Leu Thr Thr Pro Gln His Met Ser Thr Ile Leu
            740                 745                 750

Leu Glu Glu Ala Leu Pro Gln Gly Gln Pro Pro Leu Leu Glu Ala Asp
            755                 760                 765

Asp Ser Ala His Cys Gln Gly Pro Ser Lys Gly Phe Ser Pro Arg Phe
770                 775                 780

Pro Lys Gln Lys Leu Phe Pro Phe Ser Ser Arg Glu Arg Ser Phe
785                 790                 795                 800

Thr Glu Ile Asp Thr Gly Glu Asp Glu Asp Phe Leu Asp Leu Gln Arg
                805                 810                 815

Ser Arg Pro Asp Lys Gln Ala Asp Pro Ser Pro Asn Cys Leu Ala Asp
                820                 825                 830

Lys Pro Gly Asp Ala Arg Asp Ser Leu Arg Glu Glu Cys Val Gly
835                 840                 845

Ser Ser Ser Pro Gln Asn Thr Asp His Asn Cys Arg Gln Asp Ile Tyr
850                 855                 860

Gln Ala Val Gly Glu Val Lys Lys Asp Ser Ser Gln Glu Gly Tyr Lys
865                 870                 875                 880

Met Glu Asn His Leu Phe Ala Pro Glu Ile His Ser Asn Pro Gly Asp
                885                 890                 895

Thr Gly His Cys Pro Thr Arg Glu Thr Ser Met
            900                 905

<210> SEQ ID NO 41
<211> LENGTH: 858
<212> TYPE: PRT
<213> ORGANISM: Homo sapiens

```
<400> SEQUENCE: 41

Met Pro Ala Gly Met Thr Lys His Gly Ser Arg Ser Thr Ser Ser Leu
1               5                   10                  15

Pro Pro Glu Pro Met Glu Ile Val Arg Ser Lys Ala Cys Ser Arg Arg
            20                  25                  30

Val Arg Leu Asn Val Gly Gly Leu Ala His Glu Val Leu Trp Arg Thr
            35                  40                  45

Leu Asp Arg Leu Pro Arg Thr Arg Leu Gly Lys Leu Arg Asp Cys Asn
        50                  55                  60

Thr His Asp Ser Leu Leu Glu Val Cys Asp Asp Tyr Ser Leu Asp Asp
65                  70                  75                  80

Asn Glu Tyr Phe Phe Asp Arg His Pro Gly Ala Phe Thr Ser Ile Leu
                85                  90                  95

Asn Phe Tyr Arg Thr Gly Arg Leu His Met Met Glu Glu Met Cys Ala
                100                 105                 110

Leu Ser Phe Ser Gln Glu Leu Asp Tyr Trp Gly Ile Asp Glu Ile Tyr
            115                 120                 125

Leu Glu Ser Cys Cys Gln Ala Arg Tyr His Gln Lys Lys Glu Gln Met
130                 135                 140

Asn Glu Glu Leu Lys Arg Glu Ala Glu Thr Leu Arg Glu Arg Glu Gly
145                 150                 155                 160

Glu Glu Phe Asp Asn Thr Cys Cys Ala Glu Lys Arg Lys Lys Leu Trp
                165                 170                 175

Asp Leu Leu Glu Lys Pro Asn Ser Ser Val Ala Ala Lys Ile Leu Ala
            180                 185                 190

Ile Ile Ser Ile Met Phe Ile Val Leu Ser Thr Ile Ala Leu Ser Leu
        195                 200                 205

Asn Thr Leu Pro Glu Leu Gln Ser Leu Asp Glu Phe Gly Gln Ser Thr
    210                 215                 220

Asp Asn Pro Gln Leu Ala His Val Glu Ala Val Cys Ile Ala Trp Phe
225                 230                 235                 240

Thr Met Glu Tyr Leu Leu Arg Phe Leu Ser Ser Pro Lys Lys Trp Lys
                245                 250                 255

Phe Phe Lys Gly Pro Leu Asn Ala Ile Asp Leu Leu Ala Ile Leu Pro
            260                 265                 270

Tyr Tyr Val Thr Ile Phe Leu Thr Glu Ser Asn Lys Ser Val Leu Gln
        275                 280                 285

Phe Gln Asn Val Arg Arg Val Val Gln Ile Phe Arg Ile Met Arg Ile
290                 295                 300

Leu Arg Ile Leu Lys Leu Ala Arg His Ser Thr Gly Leu Gln Ser Leu
305                 310                 315                 320

Gly Phe Thr Leu Arg Arg Ser Tyr Asn Glu Leu Gly Leu Leu Ile Leu
                325                 330                 335

Phe Leu Ala Met Gly Ile Met Ile Phe Ser Ser Leu Val Phe Phe Ala
            340                 345                 350

Glu Lys Asp Glu Asp Asp Thr Lys Phe Lys Ser Ile Pro Ala Ser Phe
        355                 360                 365

Trp Trp Ala Thr Ile Thr Met Thr Thr Val Gly Tyr Gly Asp Ile Tyr
    370                 375                 380

Pro Lys Thr Leu Leu Gly Lys Ile Val Gly Gly Leu Cys Cys Ile Ala
385                 390                 395                 400

Gly Val Leu Val Ile Ala Leu Pro Ile Pro Ile Ile Val Asn Asn Phe
                405                 410                 415
```

```
Ser Glu Phe Tyr Lys Glu Gln Lys Arg Gln Glu Lys Ala Ile Lys Arg
            420                 425                 430

Arg Glu Ala Leu Glu Arg Ala Lys Arg Asn Gly Ser Ile Val Ser Met
            435                 440                 445

Asn Met Lys Asp Ala Phe Ala Arg Ser Ile Glu Met Met Asp Ile Val
450                 455                 460

Val Glu Lys Asn Gly Glu Asn Met Gly Lys Lys Asp Lys Val Gln Asp
465                 470                 475                 480

Asn His Leu Ser Pro Asn Lys Trp Lys Trp Thr Lys Arg Thr Leu Ser
                485                 490                 495

Glu Thr Ser Ser Ser Lys Ser Phe Glu Thr Lys Glu Gln Gly Ser Pro
            500                 505                 510

Glu Lys Ala Arg Ser Ser Ser Pro Gln His Leu Asn Val Gln Gln
            515                 520                 525

Leu Glu Asp Met Tyr Asn Lys Met Ala Lys Thr Gln Ser Gln Pro Ile
            530                 535                 540

Leu Asn Thr Lys Glu Ser Ala Ala Gln Ser Lys Pro Lys Glu Glu Leu
545                 550                 555                 560

Glu Met Glu Ser Ile Pro Ser Pro Val Ala Pro Leu Pro Thr Arg Thr
                565                 570                 575

Glu Gly Val Ile Asp Met Arg Ser Met Ser Ser Ile Asp Ser Phe Ile
            580                 585                 590

Ser Cys Ala Thr Asp Phe Pro Glu Ala Thr Arg Phe Ser His Ser Pro
            595                 600                 605

Leu Thr Ser Leu Pro Ser Lys Thr Gly Gly Ser Thr Ala Pro Glu Val
            610                 615                 620

Gly Trp Arg Gly Ala Leu Gly Ala Ser Gly Gly Arg Phe Val Glu Ala
625                 630                 635                 640

Asn Pro Ser Pro Asp Ala Ser Gln His Ser Ser Phe Phe Ile Glu Ser
                645                 650                 655

Pro Lys Ser Ser Met Lys Thr Asn Asn Pro Leu Lys Leu Arg Ala Leu
            660                 665                 670

Lys Val Asn Phe Met Glu Gly Asp Pro Ser Pro Leu Leu Pro Val Leu
            675                 680                 685

Gly Met Tyr His Asp Pro Leu Arg Asn Arg Gly Ser Ala Ala Ala Ala
            690                 695                 700

Val Ala Gly Leu Glu Cys Ala Thr Leu Leu Asp Lys Ala Val Leu Ser
705                 710                 715                 720

Pro Glu Ser Ser Ile Tyr Thr Thr Ala Ser Ala Lys Thr Pro Pro Arg
                725                 730                 735

Ser Pro Glu Lys His Thr Ala Ile Ala Phe Asn Phe Glu Ala Gly Val
            740                 745                 750

His Gln Tyr Ile Asp Ala Asp Thr Asp Asp Glu Gly Gln Leu Leu Tyr
            755                 760                 765

Ser Val Asp Ser Ser Pro Pro Lys Ser Leu Pro Gly Ser Thr Ser Pro
770                 775                 780

Lys Phe Ser Thr Gly Thr Arg Ser Glu Lys Asn His Phe Glu Ser Ser
785                 790                 795                 800

Pro Leu Pro Thr Ser Pro Lys Phe Leu Arg Gln Asn Cys Ile Tyr Ser
                805                 810                 815

Thr Glu Ala Leu Thr Gly Lys Gly Pro Ser Gly Gln Glu Lys Cys Lys
            820                 825                 830
```

```
Leu Glu Asn His Ile Ser Pro Asp Val Arg Val Leu Pro Gly Gly Gly
            835                 840                 845

Ala His Gly Ser Thr Arg Asp Gln Ser Ile
    850                 855

<210> SEQ ID NO 42
<211> LENGTH: 911
<212> TYPE: PRT
<213> ORGANISM: Homo sapiens

<400> SEQUENCE: 42

Met Ala Glu Lys Ala Pro Pro Gly Leu Asn Arg Lys Thr Ser Arg Ser
1               5                   10                  15

Thr Leu Ser Leu Pro Pro Glu Pro Val Asp Ile Ile Arg Ser Lys Thr
            20                  25                  30

Cys Ser Arg Arg Val Lys Ile Asn Val Gly Gly Leu Asn His Glu Val
        35                  40                  45

Leu Trp Arg Thr Leu Asp Arg Leu Pro Arg Thr Arg Leu Gly Lys Leu
    50                  55                  60

Arg Asp Cys Asn Thr His Glu Ser Leu Leu Glu Val Cys Asp Asp Tyr
65                  70                  75                  80

Asn Leu Asn Glu Asn Glu Tyr Phe Phe Asp Arg His Pro Gly Ala Phe
                85                  90                  95

Thr Ser Ile Leu Asn Phe Tyr Arg Thr Gly Lys Leu His Met Met Glu
            100                 105                 110

Glu Met Cys Ala Leu Ser Phe Gly Gln Glu Leu Asp Tyr Trp Gly Ile
        115                 120                 125

Asp Glu Ile Tyr Leu Glu Ser Cys Cys Gln Ala Arg Tyr His Gln Lys
130                 135                 140

Lys Glu Gln Met Asn Glu Glu Leu Arg Arg Glu Ala Glu Thr Met Arg
145                 150                 155                 160

Glu Arg Glu Gly Glu Glu Phe Asp Asn Thr Cys Cys Pro Asp Lys Arg
                165                 170                 175

Lys Lys Leu Trp Asp Leu Leu Glu Lys Pro Asn Ser Ser Val Ala Ala
            180                 185                 190

Lys Ile Leu Ala Ile Val Ser Ile Leu Phe Ile Val Leu Ser Thr Ile
        195                 200                 205

Ala Leu Ser Leu Asn Thr Leu Pro Glu Leu Gln Glu Thr Asp Glu Phe
210                 215                 220

Gly Gln Leu Asn Asp Asn Arg Gln Leu Ala His Val Glu Ala Val Cys
225                 230                 235                 240

Ile Ala Trp Phe Thr Met Glu Tyr Leu Leu Arg Phe Leu Ser Ser Pro
                245                 250                 255

Asn Lys Trp Lys Phe Phe Lys Gly Pro Leu Asn Val Ile Asp Leu Leu
            260                 265                 270

Ala Ile Leu Pro Tyr Tyr Val Thr Ile Phe Leu Thr Glu Ser Asn Lys
        275                 280                 285

Ser Val Leu Gln Phe Gln Asn Val Arg Arg Val Val Gln Ile Phe Arg
290                 295                 300

Ile Met Arg Ile Leu Arg Ile Leu Lys Leu Ala Arg His Ser Thr Gly
305                 310                 315                 320

Leu Gln Ser Leu Gly Phe Thr Leu Arg Arg Ser Tyr Asn Glu Leu Gly
                325                 330                 335

Leu Leu Ile Leu Phe Leu Ala Met Gly Ile Met Ile Phe Ser Ser Leu
            340                 345                 350
```

-continued

Val Phe Phe Ala Glu Lys Asp Glu Asp Ala Thr Lys Phe Thr Ser Ile
          355                 360                 365

Pro Ala Ser Phe Trp Trp Ala Thr Ile Thr Met Thr Thr Val Gly Tyr
    370                 375                 380

Gly Asp Ile Tyr Pro Lys Thr Leu Leu Gly Lys Ile Val Gly Gly Leu
385                 390                 395                 400

Cys Cys Ile Ala Gly Val Leu Val Ile Ala Leu Pro Ile Pro Ile Ile
                405                 410                 415

Val Asn Asn Phe Ser Glu Phe Tyr Lys Glu Gln Lys Arg Gln Glu Lys
            420                 425                 430

Ala Ile Lys Arg Arg Glu Ala Leu Glu Arg Ala Lys Arg Asn Gly Ser
            435                 440                 445

Ile Val Ser Met Asn Leu Lys Asp Ala Phe Ala Arg Ser Met Glu Leu
        450                 455                 460

Ile Asp Val Ala Val Glu Lys Ala Gly Glu Ser Ala Asn Thr Lys Asp
465                 470                 475                 480

Ser Ala Asp Asp Asn His Leu Ser Pro Ser Arg Trp Lys Trp Ala Arg
                485                 490                 495

Lys Ala Leu Ser Glu Thr Ser Ser Asn Lys Ser Phe Glu Asn Lys Tyr
            500                 505                 510

Gln Glu Val Ser Gln Lys Asp Ser His Glu Gln Leu Asn Asn Thr Ser
        515                 520                 525

Ser Ser Ser Pro Gln His Leu Ser Ala Gln Lys Leu Glu Met Leu Tyr
    530                 535                 540

Asn Glu Ile Thr Lys Thr Gln Pro His Ser Pro Asn Pro Asp Cys
545                 550                 555                 560

Gln Glu Lys Pro Glu Arg Pro Ser Ala Tyr Glu Glu Glu Ile Glu Met
                565                 570                 575

Glu Glu Val Val Cys Pro Gln Glu Gln Leu Ala Val Ala Gln Thr Glu
            580                 585                 590

Val Ile Val Asp Met Lys Ser Thr Ser Ser Ile Asp Ser Phe Thr Ser
        595                 600                 605

Cys Ala Thr Asp Phe Thr Glu Thr Glu Arg Ser Pro Leu Pro Pro Pro
610                 615                 620

Ser Ala Ser His Leu Gln Met Lys Phe Pro Thr Asp Leu Pro Gly Thr
625                 630                 635                 640

Glu Glu His Gln Arg Ala Arg Gly Pro Pro Phe Leu Thr Leu Ser Arg
                645                 650                 655

Glu Lys Gly Pro Ala Ala Arg Asp Gly Thr Leu Glu Tyr Ala Pro Val
            660                 665                 670

Asp Ile Thr Val Asn Leu Asp Ala Ser Gly Ser Gln Cys Gly Leu His
        675                 680                 685

Ser Pro Leu Gln Ser Asp Asn Ala Thr Asp Ser Pro Lys Ser Ser Leu
    690                 695                 700

Lys Gly Ser Asn Pro Leu Lys Ser Arg Ser Leu Lys Val Asn Phe Lys
705                 710                 715                 720

Glu Asn Arg Gly Ser Ala Pro Gln Thr Pro Ser Thr Ala Arg Pro
                725                 730                 735

Leu Pro Val Thr Thr Ala Asp Phe Ser Leu Thr Thr Pro Gln His Ile
            740                 745                 750

Ser Thr Ile Leu Leu Glu Glu Thr Pro Ser Gln Gly Asp Arg Pro Leu
        755                 760                 765

```
Leu Gly Thr Glu Val Ser Ala Pro Cys Gln Gly Pro Ser Lys Gly Leu
        770                 775                 780
Ser Pro Arg Phe Pro Lys Gln Lys Leu Phe Pro Phe Ser Ser Arg Glu
785                 790                 795                 800
Arg Arg Ser Phe Thr Glu Ile Asp Thr Gly Asp Asp Glu Asp Phe Leu
                805                 810                 815
Glu Leu Pro Gly Ala Arg Glu Glu Lys Gln Val Asp Ser Ser Pro Asn
            820                 825                 830
Cys Phe Ala Asp Lys Pro Ser Asp Gly Arg Asp Pro Leu Arg Glu Glu
        835                 840                 845
Gly Ser Val Gly Ser Ser Pro Gln Asp Thr Gly His Asn Cys Arg
    850                 855                 860
Gln Asp Ile Tyr His Ala Val Ser Glu Val Lys Lys Asp Ser Ser Gln
865                 870                 875                 880
Glu Gly Cys Lys Met Glu Asn His Leu Phe Ala Pro Glu Ile His Ser
                885                 890                 895
Asn Pro Gly Asp Thr Gly Tyr Cys Pro Thr Arg Glu Thr Ser Met
            900                 905                 910

<210> SEQ ID NO 43
<211> LENGTH: 907
<212> TYPE: PRT
<213> ORGANISM: Rattus norvegicus

<400> SEQUENCE: 43

Met Ala Glu Lys Ala Pro Pro Gly Leu Asn Arg Lys Thr Ser Arg Ser
1               5                   10                  15
Thr Leu Ser Leu Pro Pro Glu Pro Val Asp Ile Ile Arg Ser Lys Thr
                20                  25                  30
Cys Ser Arg Arg Val Lys Ile Asn Val Gly Gly Leu Asn His Glu Val
            35                  40                  45
Leu Trp Arg Thr Leu Asp Arg Leu Pro Arg Thr Arg Leu Gly Lys Leu
        50                  55                  60
Arg Asp Cys Asn Thr His Glu Ser Leu Leu Glu Val Cys Asp Asp Tyr
65                  70                  75                  80
Asn Leu Asn Glu Asn Glu Tyr Phe Phe Asp Arg His Pro Gly Ala Phe
                85                  90                  95
Thr Ser Ile Leu Asn Phe Tyr Arg Thr Gly Lys Leu His Met Met Glu
            100                 105                 110
Glu Met Cys Ala Leu Ser Phe Gly Gln Glu Leu Asp Tyr Trp Gly Ile
        115                 120                 125
Asp Glu Ile Tyr Leu Glu Ser Cys Cys Gln Ala Arg Tyr His Gln Lys
        130                 135                 140
Lys Glu Gln Met Asn Glu Glu Leu Arg Arg Glu Ala Glu Thr Met Arg
145                 150                 155                 160
Asp Gly Glu Gly Glu Glu Phe Asp Asn Thr Cys Cys Pro Glu Lys Arg
                165                 170                 175
Lys Lys Leu Trp Asp Leu Leu Glu Lys Pro Asn Ser Ser Val Ala Ala
            180                 185                 190
Lys Ile Leu Ala Ile Val Ser Ile Leu Phe Ile Val Leu Ser Thr Ile
        195                 200                 205
Ala Leu Ser Leu Asn Thr Leu Pro Glu Leu Gln Glu Asn Asp Glu Phe
    210                 215                 220
Gly Gln Pro Ser Asp Asn Arg Lys Leu Ala His Val Glu Ala Val Cys
225                 230                 235                 240
```

-continued

```
Ile Ala Trp Phe Thr Met Glu Tyr Leu Leu Arg Phe Leu Ser Ser Pro
            245                 250                 255

Asn Lys Trp Lys Phe Lys Gly Pro Leu Asn Val Ile Asp Leu Leu
            260                 265                 270

Ala Ile Leu Pro Tyr Tyr Val Thr Ile Phe Leu Thr Glu Ser Asn Lys
            275                 280                 285

Ser Val Leu Gln Phe Gln Asn Val Arg Arg Val Gln Ile Phe Arg
            290                 295                 300

Ile Met Arg Ile Leu Arg Ile Leu Lys Leu Ala Arg His Ser Thr Gly
305                 310                 315                 320

Leu Gln Ser Leu Gly Phe Thr Leu Arg Arg Ser Tyr Asn Glu Leu Gly
                    325                 330                 335

Leu Leu Ile Leu Phe Leu Ala Met Gly Ile Met Ile Phe Ser Ser Leu
                    340                 345                 350

Val Phe Phe Ala Glu Lys Asp Glu Asp Ala Thr Lys Phe Thr Ser Ile
                    355                 360                 365

Pro Ala Ser Phe Trp Trp Ala Thr Ile Thr Met Thr Thr Val Gly Tyr
            370                 375                 380

Gly Asp Ile Tyr Pro Lys Thr Leu Leu Gly Lys Ile Val Gly Gly Leu
385                 390                 395                 400

Cys Cys Ile Ala Gly Val Leu Val Ile Ala Leu Pro Ile Pro Ile Ile
                    405                 410                 415

Val Asn Asn Phe Ser Glu Phe Tyr Lys Glu Gln Lys Arg Gln Glu Lys
                    420                 425                 430

Ala Ile Lys Arg Arg Glu Ala Leu Glu Arg Ala Lys Arg Asn Gly Ser
            435                 440                 445

Ile Val Ser Met Asn Leu Lys Asp Ala Phe Ala Arg Ser Met Glu Leu
            450                 455                 460

Ile Asp Val Ala Val Glu Lys Ala Gly Glu Ser Ala Asn Ile Lys Asp
465                 470                 475                 480

Ser Val Asp Asp Asn His Leu Ser Pro Ser Arg Trp Lys Trp Ala Arg
                    485                 490                 495

Lys Ala Leu Ser Glu Thr Ser Ser Asn Lys Ser Tyr Glu Asn Lys Tyr
                    500                 505                 510

Gln Glu Val Ser Gln Lys Asp Ser His Glu Gln Leu Asn Asn Thr Ser
                    515                 520                 525

Ser Ser Ser Pro Gln His Leu Ser Ala Gln Lys Leu Glu Met Leu Tyr
530                 535                 540

Asn Glu Ile Thr Lys Thr Gln Thr His Ser His Pro Asn Pro Asp Cys
545                 550                 555                 560

Gln Glu Gln Pro Glu Arg Pro Ser Ala Tyr Glu Glu Glu Ile Glu Met
                    565                 570                 575

Glu Glu Val Val Cys Pro Gln Glu Gln Leu Ala Val Ala Gln Thr Glu
                    580                 585                 590

Val Ile Val Asp Met Lys Ser Thr Ser Ser Ile Asp Ser Phe Thr Ser
            595                 600                 605

Cys Ala Thr Asp Phe Thr Glu Thr Glu Arg Ser Pro Leu Pro Pro
610                 615                 620

Ser Ala Ser His Leu Gln Met Lys Phe Pro Thr Asp Leu Pro Gly Met
625                 630                 635                 640

Asp Glu His Gln Arg Val Arg Ala Pro Pro Phe Leu Thr Leu Ser Arg
                    645                 650                 655
```

```
Asp Lys Gly Pro Ala Ala Arg Glu Ala Ala Leu Asp Tyr Ala Pro Ile
            660                 665                 670

Asp Ile Thr Val Asn Leu Asp Ala Gly Ala Ser His Gly Pro Leu Gln
        675                 680                 685

Pro Asp Ser Ala Ser Asp Ser Pro Lys Ser Ser Leu Lys Gly Ser Asn
    690                 695                 700

Pro Leu Lys Ser Arg Ser Leu Lys Val Asn Phe Gln Glu Asn Arg Gly
705                 710                 715                 720

Ser Ala Pro Gln Thr Pro Pro Ser Thr Ala Arg Pro Leu Pro Val Thr
                725                 730                 735

Thr Ala Asp Phe Pro Leu Thr Thr Pro Gln His Met Ser Thr Ile Leu
            740                 745                 750

Leu Glu Glu Ser Pro Pro Pro Gly Thr Glu Thr Leu Pro Gly Ala Asp
        755                 760                 765

Val Ser Ala His Cys Gln Gly Pro Ser Lys Gly Leu Ser Pro Arg Val
    770                 775                 780

Pro Lys Gln Lys Leu Phe Pro Phe Ser Ser Arg Glu Arg Arg Ser Phe
785                 790                 795                 800

Thr Glu Ile Asp Thr Gly Glu Asp Glu Asp Phe Leu Asp Leu Gln Arg
                805                 810                 815

Pro Arg Pro Asp Lys Gln Ala Asp Pro Ser Pro Asn Cys Leu Ala Asp
            820                 825                 830

Lys Pro Gly Glu Ala Arg Asp Pro Leu Arg Glu Glu Gly Cys Val Gly
        835                 840                 845

Ser Ser Ser Pro Gln Asn Thr Asp His Asn Cys Arg Gln Asp Ile Tyr
    850                 855                 860

Gln Ala Val Gly Glu Val Lys Lys Asp Ser Ser Gln Glu Gly Tyr Lys
865                 870                 875                 880

Met Glu Asn His Leu Phe Ala Pro Glu Ile His Ser Asn Pro Gly Asp
                885                 890                 895

Thr Gly Tyr Cys Pro Thr Arg Glu Thr Ser Met
            900                 905

<210> SEQ ID NO 44
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (3)..(4)
<223> OTHER INFORMATION: phosphorylated serine
<220> FEATURE:
<221> NAME/KEY: MISC_FEATURE
<222> LOCATION: (6)..(6)
<223> OTHER INFORMATION: phosphorylated serine

<400> SEQUENCE: 44

Asp Phe Ser Ser Ile Ser Thr
1               5

<210> SEQ ID NO 45
<211> LENGTH: 7
<212> TYPE: PRT
<213> ORGANISM: Artificial Sequence
<220> FEATURE:
<223> OTHER INFORMATION: synthetic amino acid

<400> SEQUENCE: 45
```

Ser Ile Asp Ser Ala Thr Ser
1               5

<210> SEQ ID NO 46
<211> LENGTH: 7
<212> TYPE: PRT
<213> ORGANISM: Artificial Sequence
<220> FEATURE:
<223> OTHER INFORMATION: synthetic amino acid

<400> SEQUENCE: 46

Ala Ile Asp Ser Phe Thr Ser
1               5

<210> SEQ ID NO 47
<211> LENGTH: 7
<212> TYPE: PRT
<213> ORGANISM: Artificial Sequence
<220> FEATURE:
<223> OTHER INFORMATION: synthetic amino acid

<400> SEQUENCE: 47

Ser Ile Asp Ala Phe Thr Ser
1               5

<210> SEQ ID NO 48
<211> LENGTH: 8
<212> TYPE: PRT
<213> ORGANISM: Artificial Sequence
<220> FEATURE:
<223> OTHER INFORMATION: synthetic amino acid

<400> SEQUENCE: 48

Ser Ile Asp Ala Ser Phe Thr Ala
1               5

<210> SEQ ID NO 49
<211> LENGTH: 7
<212> TYPE: PRT
<213> ORGANISM: Artificial Sequence
<220> FEATURE:
<223> OTHER INFORMATION: synthetic amino acid

<400> SEQUENCE: 49

Ala Ile Asp Ala Phe Thr Ser
1               5

<210> SEQ ID NO 50
<211> LENGTH: 7
<212> TYPE: PRT
<213> ORGANISM: Artificial Sequence
<220> FEATURE:
<223> OTHER INFORMATION: synthetic amino acid

<400> SEQUENCE: 50

Ser Ile Asp Ala Phe Thr Ala
1               5

<210> SEQ ID NO 51
<211> LENGTH: 7
<212> TYPE: PRT
<213> ORGANISM: Artificial Sequence
<220> FEATURE:
<223> OTHER INFORMATION: synthetic amino acid

<400> SEQUENCE: 51

Ala Ile Asp Ser Phe Thr Ala

```
1               5

<210> SEQ ID NO 52
<211> LENGTH: 7
<212> TYPE: PRT
<213> ORGANISM: Artificial Sequence
<220> FEATURE:
<223> OTHER INFORMATION: synthetic amino acid

<400> SEQUENCE: 52

Ala Ile Asp Ala Phe Thr Ala
1               5

<210> SEQ ID NO 53
<211> LENGTH: 10
<212> TYPE: PRT
<213> ORGANISM: Artificial Sequence
<220> FEATURE:
<223> OTHER INFORMATION: synthetic amino acid

<400> SEQUENCE: 53

Ser Ile Asp Ser Phe Thr Ser Cys Ala Thr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic amino acid

<400> SEQUENCE: 54

Ala Ile Asp Ala Phe Thr Ala Cys Ala Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: synthetic amino acid

<400> SEQUENCE: 55

Asp Ile Asp Asp Phe Thr Asp Cys Ala Thr
1               5                   10

<210> SEQ ID NO 56
<211> LENGTH: 10
<212> TYPE: PRT
<213> ORGANISM: Artificial Sequence
<220> FEATURE:
<223> OTHER INFORMATION: synthetic amino acid

<400> SEQUENCE: 56

Glu Ile Asp Glu Phe Thr Glu Cys Ala Thr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
```

```
<221> NAME/KEY: MISC_FEATURE
<222> LOCATION: (4)..(4)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 57

Ser Ile Asp Ser Phe Thr Ser Cys Ala Thr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic amino acid

<400> SEQUENCE: 58

Ser Ile Asp Ser Phe Thr Ser Ala Ala Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: synthetic amino acid

<400> SEQUENCE: 59

Ala Ile Asp Ala Phe Thr Ala Ala Ala Ala
1               5                   10

<210> SEQ ID NO 60
<211> LENGTH: 10
<212> TYPE: PRT
<213> ORGANISM: Artificial Sequence
<220> FEATURE:
<223> OTHER INFORMATION: synthetic amino acid

<400> SEQUENCE: 60

Asp Ile Asp Asp Phe Thr Asp Ala Ala Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: synthetic amino acid

<400> SEQUENCE: 61

Glu Ile Asp Glu Phe Thr Glu Ala Ala Ala
1               5                   10

<210> SEQ ID NO 62
<211> LENGTH: 10
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
```

```
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 62

Ser Ile Asp Ser Phe Thr Ser Ala Ala Ala
1               5                   10

<210> SEQ ID NO 63
<211> LENGTH: 7
<212> TYPE: PRT
<213> ORGANISM: Artificial Sequence
<220> FEATURE:
<223> OTHER INFORMATION: synthetic amino acid

<400> SEQUENCE: 63

Ala Phe Thr Ala Cys Ala Thr
1               5

<210> SEQ ID NO 64
<211> LENGTH: 7
<212> TYPE: PRT
<213> ORGANISM: Artificial Sequence
<220> FEATURE:
<223> OTHER INFORMATION: synthetic amino acid

<400> SEQUENCE: 64

Asp Phe Thr Asp Cys Ala Thr
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic amino acid

<400> SEQUENCE: 65

Glu Phe Thr Glu Cys Ala Thr
1               5

<210> SEQ ID NO 66
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 66

Ser Phe Thr Ser Cys Ala Thr
1               5

<210> SEQ ID NO 67
<211> LENGTH: 7
<212> TYPE: PRT
<213> ORGANISM: Artificial Sequence
<220> FEATURE:
<223> OTHER INFORMATION: synthetic amino acid
```

```
<400> SEQUENCE: 67

Ser Phe Thr Ser Ala Ala Ala
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic amino acid

<400> SEQUENCE: 68

Ala Phe Thr Ala Ala Ala Ala
1               5

<210> SEQ ID NO 69
<211> LENGTH: 7
<212> TYPE: PRT
<213> ORGANISM: Artificial Sequence
<220> FEATURE:
<223> OTHER INFORMATION: synthetic amino acid

<400> SEQUENCE: 69

Asp Phe Thr Asp Ala Ala Ala
1               5

<210> SEQ ID NO 70
<211> LENGTH: 7
<212> TYPE: PRT
<213> ORGANISM: Artificial Sequence
<220> FEATURE:
<223> OTHER INFORMATION: synthetic amino acid

<400> SEQUENCE: 70

Glu Phe Thr Glu Ala Ala Ala
1               5

<210> SEQ ID NO 71
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 71

Ser Phe Thr Ser Ala Ala Ala
1               5

<210> SEQ ID NO 72
<211> LENGTH: 4
<212> TYPE: PRT
<213> ORGANISM: Artificial Sequence
<220> FEATURE:
<223> OTHER INFORMATION: synthetic amino acid

<400> SEQUENCE: 72

Ser Phe Thr Ser
1
```

```
<210> SEQ ID NO 73
<211> LENGTH: 4
<212> TYPE: PRT
<213> ORGANISM: Artificial Sequence
<220> FEATURE:
<223> OTHER INFORMATION: synthetic amino acid

<400> SEQUENCE: 73

Ala Phe Thr Ala
1

<210> SEQ ID NO 74
<211> LENGTH: 4
<212> TYPE: PRT
<213> ORGANISM: Artificial Sequence
<220> FEATURE:
<223> OTHER INFORMATION: synthetic amino acid

<400> SEQUENCE: 74

Asp Phe Thr Asp
1

<210> SEQ ID NO 75
<211> LENGTH: 4
<212> TYPE: PRT
<213> ORGANISM: Artificial Sequence
<220> FEATURE:
<223> OTHER INFORMATION: synthetic amino acid

<400> SEQUENCE: 75

Glu Phe Thr Glu
1

<210> SEQ ID NO 76
<211> LENGTH: 4
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 76

Ser Phe Thr Ser
1

<210> SEQ ID NO 77
<211> LENGTH: 4
<212> TYPE: PRT
<213> ORGANISM: Artificial Sequence
<220> FEATURE:
<223> OTHER INFORMATION: synthetic amino acid

<400> SEQUENCE: 77

Ser Ile Asp Ser
1

<210> SEQ ID NO 78
<211> LENGTH: 4
<212> TYPE: PRT
<213> ORGANISM: Artificial Sequence
<220> FEATURE:
<223> OTHER INFORMATION: synthetic amino acid
```

<400> SEQUENCE: 78

Ala Ile Asp Ala
1

<210> SEQ ID NO 79
<211> LENGTH: 4
<212> TYPE: PRT
<213> ORGANISM: Artificial Sequence
<220> FEATURE:
<223> OTHER INFORMATION: synthetic amino acid

<400> SEQUENCE: 79

Asp Ile Asp Asp
1

<210> SEQ ID NO 80
<211> LENGTH: 4
<212> TYPE: PRT
<213> ORGANISM: Artificial Sequence
<220> FEATURE:
<223> OTHER INFORMATION: synthetic amino acid

<400> SEQUENCE: 80

Glu Ile Asp Glu
1

<210> SEQ ID NO 81
<211> LENGTH: 4
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 81

Ser Ile Asp Ser
1

<210> SEQ ID NO 82
<211> LENGTH: 4
<212> TYPE: PRT
<213> ORGANISM: Artificial Sequence
<220> FEATURE:
<223> OTHER INFORMATION: synthetic amino acid

<400> SEQUENCE: 82

Ile Asp Ser Phe
1

<210> SEQ ID NO 83
<211> LENGTH: 4
<212> TYPE: PRT
<213> ORGANISM: Artificial Sequence
<220> FEATURE:
<223> OTHER INFORMATION: synthetic amino acid

<400> SEQUENCE: 83

Ile Asp Ala Phe
1

```
<210> SEQ ID NO 84
<211> LENGTH: 4
<212> TYPE: PRT
<213> ORGANISM: Artificial Sequence
<220> FEATURE:
<223> OTHER INFORMATION: synthetic amino acid

<400> SEQUENCE: 84

Ile Asp Asp Phe
1

<210> SEQ ID NO 85
<211> LENGTH: 4
<212> TYPE: PRT
<213> ORGANISM: Artificial Sequence
<220> FEATURE:
<223> OTHER INFORMATION: synthetic amino acid

<400> SEQUENCE: 85

Ile Asp Glu Phe
1

<210> SEQ ID NO 86
<211> LENGTH: 4
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (3)..(3)
<223> OTHER INFORMATION: phosphorylated serine

<400> SEQUENCE: 86

Ile Asp Ser Phe
1

<210> SEQ ID NO 87
<211> LENGTH: 7
<212> TYPE: PRT
<213> ORGANISM: Artificial Sequence
<220> FEATURE:
<223> OTHER INFORMATION: synthetic amino acid

<400> SEQUENCE: 87

Ser Ile Val Ser Phe His Ser
1               5

<210> SEQ ID NO 88
<211> LENGTH: 7
<212> TYPE: PRT
<213> ORGANISM: Artificial Sequence
<220> FEATURE:
<223> OTHER INFORMATION: synthetic amino acid

<400> SEQUENCE: 88

Ala Ile Val Ala Phe His Ala
1               5

<210> SEQ ID NO 89
<211> LENGTH: 7
<212> TYPE: PRT
<213> ORGANISM: Artificial Sequence
<220> FEATURE:
<223> OTHER INFORMATION: synthetic amino acid

<400> SEQUENCE: 89
```

Asp Ile Val Asp Phe His Asp
1               5

<210> SEQ ID NO 90
<211> LENGTH: 7
<212> TYPE: PRT
<213> ORGANISM: Artificial Sequence
<220> FEATURE:
<223> OTHER INFORMATION: synthetic amino acid

<400> SEQUENCE: 90

Glu Ile Val Glu Phe His Glu
1               5

<210> SEQ ID NO 91
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 91

Ser Ile Val Ser Phe His Ser
1               5

<210> SEQ ID NO 92
<211> LENGTH: 7
<212> TYPE: PRT
<213> ORGANISM: Artificial Sequence
<220> FEATURE:
<223> OTHER INFORMATION: synthetic amino acid

<400> SEQUENCE: 92

Ser Ile Asp Ser Phe Ile Ser
1               5

<210> SEQ ID NO 93
<211> LENGTH: 7
<212> TYPE: PRT
<213> ORGANISM: Artificial Sequence
<220> FEATURE:
<223> OTHER INFORMATION: synthetic amino acid

<400> SEQUENCE: 93

Ala Ile Asp Ala Phe Ile Ala
1               5

<210> SEQ ID NO 94
<211> LENGTH: 7
<212> TYPE: PRT
<213> ORGANISM: Artificial Sequence
<220> FEATURE:
<223> OTHER INFORMATION: synthetic amino acid

<400> SEQUENCE: 94

Asp Ile Asp Asp Phe Ile Asp
1               5

```
<210> SEQ ID NO 95
<211> LENGTH: 7
<212> TYPE: PRT
<213> ORGANISM: Artificial Sequence
<220> FEATURE:
<223> OTHER INFORMATION: synthetic amino acid

<400> SEQUENCE: 95

Glu Ile Asp Glu Phe Ile Glu
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine
<220> FEATURE:
<221> NAME/KEY: MISC_FEATURE
<222> LOCATION: (7)..(7)
<223> OTHER INFORMATION: phosphorylated serine

<400> SEQUENCE: 96

Ser Ile Asp Ser Phe Ile Ser
1               5

<210> SEQ ID NO 97
<211> LENGTH: 7
<212> TYPE: PRT
<213> ORGANISM: Artificial Sequence
<220> FEATURE:
<223> OTHER INFORMATION: synthetic amino acid

<400> SEQUENCE: 97

Ser Ile Val Ser Phe His His
1               5

<210> SEQ ID NO 98
<211> LENGTH: 7
<212> TYPE: PRT
<213> ORGANISM: Artificial Sequence
<220> FEATURE:
<223> OTHER INFORMATION: synthetic amino acid

<400> SEQUENCE: 98

Ala Ile Val Ala Phe His His
1               5

<210> SEQ ID NO 99
<211> LENGTH: 7
<212> TYPE: PRT
<213> ORGANISM: Artificial Sequence
<220> FEATURE:
<223> OTHER INFORMATION: synthetic amino acid

<400> SEQUENCE: 99

Asp Ile Val Asp Phe His His
1               5
```

```
<210> SEQ ID NO 100
<211> LENGTH: 7
<212> TYPE: PRT
<213> ORGANISM: Artificial Sequence
<220> FEATURE:
<223> OTHER INFORMATION: synthetic amino acid

<400> SEQUENCE: 100

Glu Ile Val Glu Phe His His
1               5

<210> SEQ ID NO 101
<211> LENGTH: 7
<212> TYPE: PRT
<213> ORGANISM: Artificial Sequence
<220> FEATURE:
<223> OTHER INFORMATION: synthetic amino acid
<220> FEATURE:
<221> NAME/KEY: MISC_FEATURE
<222> LOCATION: (1)..(1)
<223> OTHER INFORMATION: phosphorylated serine
<220> FEATURE:
<221> NAME/KEY: MISC_FEATURE
<222> LOCATION: (4)..(4)
<223> OTHER INFORMATION: phosphorylated serine

<400> SEQUENCE: 101

Ser Ile Val Ser Phe His His
1               5
```